United States Patent
Li et al.

(10) Patent No.: US 6,638,952 B1
(45) Date of Patent: *Oct. 28, 2003

(54) AROMATIC SULFONYL ALPHA-CYCLOAMINO HYDROXAMIC ACID COMPOUNDS

(75) Inventors: Hui Li, Vernon Hills, IL (US); Daniel P. Becker, Glenview, IL (US); Clara I. Villamil, Glenview, IL (US); Terri L. Boehm, Ballwin, MO (US); Daniel P. Getman, Chesterfield, MO (US); Joseph J. McDonald, Ballwin, MO (US); Gary A. DeCrescenzo, St. Charles, MO (US)

(73) Assignee: Pharmacia Corporation, Skokie, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/254,530

(22) PCT Filed: Mar. 4, 1998

(86) PCT No.: PCT/US98/04273

§ 371 (c)(1),
(2), (4) Date: Dec. 23, 1999

(87) PCT Pub. No.: WO98/39315

PCT Pub. Date: Sep. 11, 1998

Related U.S. Application Data

(60) Provisional application No. 60/035,182, filed on Mar. 4, 1997.

(51) Int. Cl.[7] ..................... A61K 31/445; C07D 211/22
(52) U.S. Cl. ......................................... 514/330; 546/221
(58) Field of Search ........................... 514/330; 546/221

(56) References Cited

U.S. PATENT DOCUMENTS

| | | | |
|---|---|---|---|
| 4,595,700 A | | 6/1986 | Donald et al. ............... 514/616 |
| 5,932,595 A | * | 8/1999 | Bender et al. ............... 514/317 |
| 6,172,057 B1 | * | 1/2001 | Venkatesan ............ 514/212.01 |
| 2001/0014688 A1 | * | 8/2001 | Barta ........................ 514/318 |

FOREIGN PATENT DOCUMENTS

| | | | | |
|---|---|---|---|---|
| EP | 780386 | * | 6/1997 | |
| EP | 0 780 386 | | 6/1997 | |
| WO | WO 90/05719 | | 5/1990 | |
| WO | WO 93/20047 | | 10/1993 | |
| WO | WO 94/02466 | | 2/1994 | |
| WO | WO 94/24140 | | 10/1994 | |
| WO | WO 95/09841 | | 4/1995 | |
| WO | WO 95/12389 | | 5/1995 | |
| WO | WO95/13289 | | 5/1995 | ........... C07K/5/062 |
| WO | WO 95/29892 | | 11/1995 | |
| WO | WO 96/00214 | | 1/1996 | ......... C07D/213/42 |
| WO | WO 96/06074 | | 2/1996 | |
| WO | WO 96/11209 | | 4/1996 | |
| WO | WO 97/20824 | | 6/1997 | |
| WO | WO 97/24117 | | 7/1997 | |
| WO | WO 97/49679 | | 12/1997 | |
| WO | 98/37877 | * | 9/1998 | |
| WO | WO 98/39315 | | 9/1998 | ......... C07D/309/08 |
| WO | WO 99/25687 | | 5/1999 | ......... C07D/211/66 |
| WO | WO 00/50396 | | 8/2000 | ......... C07D/211/66 |

OTHER PUBLICATIONS

Bender et al. "Preparation of arylthioalkanoates ... " CA 127:135724 (1997) structure delineation of relevant compounds.*
U.S. patent application Ser. No. 09/554,082, Barta et al., filed Jul. 31, 2000.
U.S. patent application Ser. No. 09/989,943, Barta et al., filed Nov. 21, 2001.
U.S. patent application Ser. No. 09/554,082, Barta et al., filed Jul. 31, 2000.
U.S. patent application Ser. No. 09/570,731, Barta et al., filed May 12, 2000.
U.S. patent application Ser. No. 09/311,837, Barta et al., filed May 14, 1999.
U.S. patent application Ser. No. 09/954,451, Barta et al., filed Sep. 17, 2001.
U.S. patent application Ser. No. 09/191,129, Barta et al., filed Nov. 13, 1998.
U.S. patent application Ser. No. 10/142,737, Barta et al., filed May 10, 2002.
Becker et al., α*Alkyl–α–amino–β–sulphone Hydroxamates as Potent MMP Inhibitors that Spare MMP–1*, Bioorganic & Medicinal Chemistry Letters 11 (2001) 2723–2725.
Schwartz et al., *Progr. Med. Chem.*, 29:271–334 (1992).
Rasmussen et al., *Pharmacol. Ther.*, 75(1): 69–75 (1997).
Denis et al., *Invest. New Drugs*, 15(3): 175–185 (1997).
Gearing et al., *Nature* 376, 555–557 (1994).
McGeehan et al., *Naturen* 376, 558–561 (1994).
Mitchell et al., *J. Clin. Invest.*, 97:761–768 (1996).
Reboul et al., *J. Clin. Invest.*, 97:2011–2019 (1996).
*A Model of Angiogenesis in the Mouse Cornea*; Kenyon,BM, et al., Investigative Ophthalmology & Visual Science, Jul. 1996, vol. 37, No. 8.
Knight et al., FEBS Lett. 296(3):263 (1992).

* cited by examiner

*Primary Examiner*—Ceila Chang
(74) *Attorney, Agent, or Firm*—Julie Chappell; Philip B. Polster, II; Ed Gamson, Welsh & Katz, LTD

(57) ABSTRACT

An aromatic sulfonyl alpha-cycloamino hydroxamic acid compound that inter alia inhibits matrix metalloprotease activity is disclosed as are a treatment process that comprises administering a contemplated aromatic sulfonyl alpha-cycloamino hydroxamic acid compound in a MMP enzyme-inhibiting effective amount to a host having a condition associated with pathological matrix metalloprotease activity.

24 Claims, No Drawings

US 6,638,952 B1

AROMATIC SULFONYL ALPHA-CYCLOAMINO HYDROXAMIC ACID COMPOUNDS

This application claims the benefit of provisional application Ser. No. 60/035,182 filed Mar. 4, 1997.

TECHNICAL FIELD

This invention is directed to proteinase (protease) inhibitors, and more particularly to aromatic sulfonyl alpha-cycloamino hydroxamic acid compounds that, inter alia, inhibit the activity of matrix metalloproteinases, compositions of those inhibitors, intermediates for the syntheses of those compounds, processes for the preparation of the compounds and processes for treating pathological conditions associated with pathological matrix metalloproteinase activity.

BACKGROUND OF THE INVENTION

Connective tissue, extracellular matrix constituents and basement membranes are required components of all mammals. These components are the biological materials that provide rigidity, differentiation, attachments and, in some cases, elasticity to biological systems including human beings and other mammals. Connective tissues components include, for example, collagen, elastin, proteoglycans, fibronectin and laminin. These biochemicals make up, or are components of structures, such as skin, bone, teeth, tendon, cartilage, basement membrane, blood vessels, cornea and vitreous humor.

Under normal conditions, connective tissue turnover and/or repair processes are controlled and in equilibrium. The loss of this balance for whatever reason is involved in a number of disease states. Inhibition of the enzymes responsible loss of equilibrium provides a control mechanism for this tissue decomposition and, therefore, a treatment for these diseases.

Degradation of connective tissue or connective tissue components is carried out by the action of proteinase enzymes released from resident tissue cells and/or invading inflammatory or tumor cells. A major class of enzymes involved in this function are the zinc metalloproteinases (metalloproteases, or MMPs).

The metalloprotease enzymes are divided into classes with some members having several different names in common use. Examples are: collagenase I (MMP-1, fibroblast collagenase; EC 3.4.24.3); collagenase II (MMP-8, neutrophil collagenase; EC 3.4.24.34), collagenase III (MMP-13), stromelysin 1 (MMP-3; EC 3.4.24.17), stromelysin 2 (MMP-10; EC 3.4.24.22), proteoglycanase, matrilysin (MMP-7), gelatinase A (MMP-2, 72 kDa gelatinase, basement membrane collagenase; EC 3.4.24.24), gelatinase B (MMP-9, 92 kDa gelatinase; EC 3.4.24.35), stromelysin 3 (MMP-11), metalloelastase (MMP-12, HME, human macrophage elastase) and membrane MMP (MMP-14). MMP is an abbreviation or acronym representing the term Matrix Metalloprotease with the attached numerals providing differentiation between specific members of the MMP group.

The uncontrolled breakdown of connective tissue by metalloproteases is a feature of many pathological conditions. Examples include rheumatoid arthritis, osteoarthritis, septic arthritis; multiple sclerosis; corneal, epidermal or gastric ulceration; tumor metastasis, invasion or angiogenesis; periodontal disease; proteinuria; Alzheimer's Disease; coronary thrombosis and bone disease. Defective injury repair processes can also occur. This can produce improper wound healing leading to weak repairs, adhesions and scarring. These latter defects can lead to disfigurement and/or permanent disabilities as with post-surgical adhesions.

Matrix metalloproteases are also involved in the biosynthesis of tumor necrosis factor (TNF) and inhibition of the production or action of TNF and related compounds is an important clinical disease treatment mechanism. TNF-α, for example, is a cytokine that at present is thought to be produced initially as a 28 kD cell-associated molecule. It is released as an active, 17 kD form that can mediate a large number of deleterious effects in vitro and in vivo. For example, TNF can cause and/or contribute to the effects of inflammation, rheumatoid arthritis, autoimmune disease, multiple sclerosis, graft rejection, fibrotic disease, cancer, infectious diseases, malaria, mycobacterial infection, meningitis, fever, psoriasis, cardiovascular/pulmonary effects such as post-ischemic reperfusion injury, congestive heart failure, hemorrhage, coagulation, hyperoxic alveolar injury, radiation damage and acute phase responses like those seen with infections and sepsis and during shock such as septic shock and hemodynamic shock. Chronic release of active TNF can cause cachexia and anorexia. TNF can be lethal.

TNF-α convertase is a metalloproteinase involved in the formation of active TNF-α. Inhibition of TNF-α convertase inhibits production of active TNF-α. Compounds that inhibit both MMPs activity have been disclosed in WIPO International Publication Nos. WO 94/24140, WO 94/02466 and WO 97/20824. There remains a need for effective MMP and TNF-α convertase inhibiting agents. Compounds that inhibit MMPs such as collagenase, stromelysin and gelatinase have been shown to inhibit the release of TNF (Gearing et al. *Nature* 376, 555–557 (1994), McGeehan et al., *Nature* 376, 558–561 (1994)).

MMPs are involved in other biochemical processes in mammals as well. Included is the control of ovulation, post-partum uterine involution, possibly implantation, cleavage of APP (β-Amyloid Precursor Protein) to the amyloid plaque and inactivation of $\alpha_1$-protease inhibitor ($\alpha_1$-PI). Inhibition of these metalloproteases permits the control of fertility and the treatment or prevention of Alzheimers Disease. In addition, increasing and maintaining the levels of an endogenous or administered serine protease inhibitor drug or biochemical such as $\alpha_1$-PI supports the treatment and prevention of diseases such as emphysema, pulmonary diseases, inflammatory diseases and diseases of aging such as loss of skin or organ stretch and resiliency.

Inhibition of selected MMPs can also be desirable in other instances. Treatment of cancer and/or inhibition of metastasis and/or inhibition of angiogenesis are examples of approaches to the treatment of diseases wherein the selective inhibition of stromelysin (MMP-3), gelatinase (MMP-2), gelatinase B (MMP-9) or collagenase III (MMP-13) are the relatively most important enzyme or enzymes to inhibit especially when compared with collagenase I (MMP-1). A drug that does not inhibit collagenase I can have a superior therapeutic profile. Osteoarthritis, another prevalent disease wherein it is believed that cartilage degradation in inflamed joints is at least partially caused by MMP-13 released from cells such as stimulated chrondrocytes, may be best treated by administration of drugs one of whose modes of action is inhibition of MMP-13. See, for example, Mitchell et al., *J. Clin. Invest.*, 97:761–768 (1996) and Reboul et al., *J. Clin. Invest.*, 97:2011–2019 (1996).

Inhibitors of metalloproteases are known. Examples include natural biochemicals such as tissue inhibitor of metalloproteinase (TIMP), $\alpha_2$-macroglobulin and their analogs or derivatives. These are high molecular weight protein molecules that form inactive complexes with metalloproteases. A number of smaller peptide-like compounds that inhibit metalloproteases have been described. Mercaptoamide peptidyl derivatives have shown ACE inhibition in vitro and in vivo. Angiotensin converting enzyme (ACE) aids in the production of angiotensin II, a potent pressor substance in mammals and inhibition of this enzyme leads to the lowering of blood pressure.

Thiol group-containing amide or peptidyl amide-based metalloprotease (MMP) inhibitors are known as is shown in, for example, WO95/12389, WO96/11209 and U.S. Pat. No. 4,595,700. Hydroxamate group-containing MMP inhibitors are disclosed in a number of published patent applications such as WO 95/29892, WO 97/24117, WO 97/49679 and EP 0 780 386 that disclose carbon back-boned compounds, and WO 90/05719, WO 93/20047, WO 95/09841 and WO 96/06074 that disclose hydroxamates that have a peptidyl back-bones or peptidomimetic back-bones, as does the article by Schwartz et al., *Progr. Med. Chem.*, 29:271–334 (1992) and those of Rasmussen et al., *Pharmacol. Ther.*, 75(1): 69–75 (1997) and Denis et al., *Invest. New Drugs*, 15(3): 175–185 (1997).

One possible problem associated with known MMP inhibitors is that such compounds often exhibit the same or similar inhibitory effects against each of the MMP enzymes. For example, the peptidomimetic hydroxamate known as batimastat is reported to exhibit $IC_{50}$ values of about 1 to about 20 nanomolar (nM) against each of MMP-1, MMP-2, MMP-3, MMP-7, and MMP-9. Marimastat, another peptidomimetic hydroxamate was reported to be another broad-spectrum MMP inhibitor with an enzyme inhibitory spectrum very similar to batimastat, except that marimastat exhibited an $IC_{50}$ value against MMP-3 of 230 nM. Rasmussen et al., *Pharmacol. Ther.*, 75(1): 69–75 (1997).

Meta analysis of data from Phase I/II studies using marimastat in patients with advanced, rapidly progressive, treatment-refractory solid tumor cancers (colorectal, pancreatic, ovarian, prostate) indicated a dose-related reduction in the rise of cancer-specific antigens used as surrogate markers for biological activity. Although marimastat exhibited some measure of efficacy via these markers, toxic side effects were noted. The most common drug-related toxicity of marimastat in those clinical trials was musculoskeletal pain and stiffness, often commencing in the small joints in the hands, spreading to the arms and shoulder. A short dosing holiday of 1–3 weeks followed by dosage reduction permits treatment to continue. Rasmussen et al., *Pharmacol. Ther.*, 75(1): 69–75 (1997). It is thought that the lack of specificity of inhibitory effect among the MMPs may be the cause of that effect.

In view of the importance of hydroxamate MMP inhibitor compounds in the treatment of several diseases and the lack of enzyme specificity exhibited by two of the more potent drugs now in clinical trials, it would be a great benefit if hydroxamates of greater enzyme specificity could be found. This would be particularly the case if the hydroxamate inhibitors exhibited strong inhibitory activity against one or more of MMP-2, MMP-9 or MMP-13 that are associated with several pathological conditions, while at the same time exhibiting limited inhibition of MMP-1, an enzyme that is relatively ubiquitous and known to participate in a number of homeostatic processes. The disclosure that follows describes one family of hydroxamate MMP inhibitors that exhibit those desirable activities.

BRIEF SUMMARY OF THE INVENTION

The present invention is directed to a family of molecules that among other properties inhibit matrix metalloprotease (MMP) activity, and particularly inhibit the activity of one or more of MMP-2, MMP-9, or MMP-13, while generally exhibiting little activity against MMP-1, as well as to a process for treating a mammal having a condition associated with pathological activity.

Briefly, one embodiment of the present invention is directed to an aromatic sulfonyl alpha-cycloamino hydroxamic acid compound that can act as a matrix metalloprotease enzyme inhibitor. That compound corresponds in structure to Formula I.

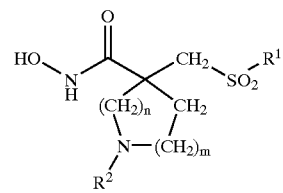

wherein m is zero, 1, 2 or 3;

n is zero, 1, or 2, and the sum of m plus n is 1, 2 or 3;

$R^2$ is hydrido, $C_1$–$C_8$ hydrocarbyl, $C_1$–$C_6$ hydrocarbyloxycarbonyl $C_1$–$C_4$ hydrocarbyl, aryl $C_1$–$C_4$ hydrocarbyl, heteroaryl $C_1$–$C_4$ hydrocarbyl, aryloxy $C_1$–$C_4$ hydrocarbyl, or heteroaryloxy $C_1$–$C_4$ hydrocarbyl. $R^2$ is preferably hydrido, $C_3$–$C_6$ cyclohydrocarbyl, t-butoxycarbonyl, phenethyl, 2-propynyl, or 3-methoxybenzyl.

$R^1$ is a substituent containing a 5- or 6-membered cyclohydrocarbyl, heterocyclo, aryl or heteroaryl radical bonded directly to the depicted $SO_2$-group and having a length greater than about that of a hexyl group and less than about that of an eicosyl group. $R^1$ defines a three-dimensional volume, when rotated about an axis drawn through the $SO_2$-bonded 1-position and the 4-position of a 6-membered ring radical or drawn through the $SO_2$-bonded 1-position and the center of 3,4-bond of a 5-membered ring radical, whose widest dimension in a direction transverse to the axis of rotation is about that of one furanyl ring to about that of two phenyl rings.

$R^1$ preferably contains a single aromatic or heteroaromatic ring that is itself substituted with another substituent, $R^3$. $R^1$ most preferably contains a phenyl ring, Ph, that itself has a substituent, $R^3$, at the 4-position. $R^3$ is preferably a phenyl, a phenoxy, a phenylazo, a thiophenoxy, an anilino, a benzamido, a nicotinamido, an isonicotinamido, a picolinamido or a phenylureido group that can itself be substituted at the meta- or para-position or both by a single atom or a substituent containing a longest chain of up to eight atoms, excluding hydrogen.

Particularly preferred compounds correspond in structure to Formulas II and IV, below, wherein $R^1$ and $R^2$ are as before described.

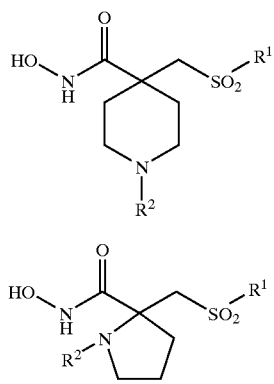

Most preferably, a contemplated compound contains an $R^1$ substituent that is $PhR^3$, wherein Ph is phenyl, $R^3$ is bonded at the 4-position and is substituent having a chain length of 3 to about 14 carbon atoms such as a hydrocarbyl or hydrocarbyloxy group [e.g., $C_3$–$C_{14}$ hydrocarbyl or —O—$C_2$–$C_{14}$ hydrocarbyl], a phenyl group, a phenoxy group, a thiophenoxy group, an anilino group, a phenylazo group, an phenylureido group, a benzamido group, a nicotinamido group, an isonicotinamido group, or a picolinamido group.

A process for treating a host mammal having a condition associated with pathological matrix metalloprotease activity is also contemplated. That process comprises administering a compound described hereinbefore in an enzyme-inhibiting effective amount to a mammalian host having such a condition. The use of repeated administrations is particularly contemplated.

Among the several benefits and advantages of the present invention are the provision of compounds and compositions effective as inhibitors of matrix metalloproteinase activity, and the provision of such compounds and compositions that are effective for the inhibition of metalloproteinases implicated in diseases and disorders involving uncontrolled breakdown of connective tissue.

More particularly, a benefit of this invention is the provision of a compound and composition effective for inhibiting metalloproteinases, particularly MMP-13 and/or MMP-2, associated with pathological conditions such as, for example, rheumatoid arthritis, osteoarthritis, or septic arthritis; corneal, epidermal or gastric ulceration; tumor metastasis, invasion or angiogenesis; periodontal disease; proteinuria; multiple sclerosis Alzheimer's Disease, coronary thrombosis and bone disease.

An advantage of the invention is the provision of a method for preparing such compositions. Another benefit is the provision of a method for treating a pathological condition associated with abnormal matrix metalloproteinase activity.

Another advantage of the invention is the provision of compounds, compositions and methods effective for treating such pathological conditions by selective inhibition of a metalloproteinase such as MMP-13 and MMP-2 associated with such conditions with minimal side effects resulting from inhibition of other proteinases such as MMP-1, whose activity is necessary or desirable for normal body function.

Still further benefits and advantages of the invention will be apparent to the skilled worker from the disclosure that follows.

DETAILED DESCRIPTION OF PREFERRED EMBODIMENT

In accordance with the present invention, it has been found that certain aromatic sulfonyl alpha-cycloamino hydroxamic acids (hydroxamates) are effective for inhibition of matrix metalloproteinases ("MMPs") believed to be associated with uncontrolled or otherwise pathological breakdown of connective tissue. In particular, it has been found that these certain aromatic sulfonyl alpha-cycloamino hydroxamic acids are effective for inhibition of collagenase III (MMP-13) and also gelatinase A (MMP-2), which can be particularly destructive to tissue if present or generated in abnormal quantities or concentrations, and thus exhibit a pathological activity. Moreover, it has been discovered that many of these aromatic sulfonyl alpha-cycloamino hydroxamic acids are selective in the inhibition of MMP-13, as well as other MMPs associated with diseased conditions without excessive inhibition of other collagenases essential to normal bodily function such as tissue turnover and repair. More particularly, it has been found that particularly preferred the aromatic sulfonyl alpha-cycloamino hydroxamic acids are particularly active in inhibiting of MMP-13 and MMP-2, while having a limited or minimal effect on MMP-1. This point is discussed in detail hereinafter and is illustrated in the Inhibition Table (Table 13) hereinafter.

One embodiment of the present invention is directed to an aromatic sulfonyl alpha-cycloamino hydroxamic acid compound that can act as a matrix metalloprotease enzyme inhibitor. That compound corresponds in structure to Formula I.

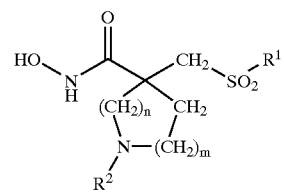

wherein m is zero, 1, 2 or 3;

n is zero, 1, or 2, and the sum of m plus n is 1, 2 or 3;

$R^2$ is hydrido, $C_1$–$C_8$ hydrocarbyl, $C_1$–$C_6$ hydrocarbyloxycarbonyl $C_1$–$C_4$ hydrocarbyl, aryl $C_1$–$C_4$ hydrocarbyl, heteroaryl $C_1$–$C_4$ hydrocarbyl, aryloxy $C_1$–$C_4$ hydrocarbyl, or heteroaryloxy $C_1$–$C_4$ hydrocarbyl. $R^2$ is preferably hydrido, $C_3$–$C_6$ cyclohydrocarbyl, t-butoxycarbonyl, phenethyl, 2-propynyl, or 3-methoxybenzyl; and $R^1$ is a substituent containing a 5- or 6-membered cyclohydrocarbyl, heterocyclo, aryl or heteroaryl radical bonded directly to the depicted $SO_2$-group and having a length equivalent to a length that is greater than about that of a fully extended hexyl group and less than about that of a fully extended eicosyl group, said $R^1$ defining a three-dimensional volume, when rotated about an axis drawn through the $SO_2$-bonded 1-position and the 4-position of a 6-membered ring radical or drawn through the $SO_2$-bonded 1-position and the center of 3,4-bond of a 5-membered ring radical, whose widest dimension in a direction transverse to the axis of rotation is about that of one furanyl ring to about that of two phenyl rings.

As noted above, an $R^1$ substituent contains a 5- or 6-membered cyclohydrocarbyl, heterocyclo, aryl or heteroaryl radical bonded directly to the depicted $SO_2$-group. An $R^1$ substituent also has length, width and substitution requirements that are discussed in detail below. It is noted here, however, that a single-ringed or fused ring cyclohydrocarbyl, heterocyclo, aryl or heteroaryl radical is not itself long enough to fulfill the length requirement. As such, that cyclohydrocarbyl, heterocyclo, aryl or heteroaryl radical must itself be substituted.

Exemplary 5- or 6-membered cyclohydrocarbyl, heterocyclo, aryl or heteroaryl radicals that can constitute a portion of a $R^1$ substituent and are themselves substituted as discussed herein include phenyl, 2-, 3-, or 4-pyridyl, 2-naththyl, 2-pyrazinyl, 2- or 5-pyrimidinyl, 2- or 3-benzo (b)thienyl, 8-purinyl, 2- or 3-furyl, 2- or 3-pyrrolyl, 2-imidazolyl, cyclopentyl, cyclohexyl, 2- or 3-piperidinyl, 2- or 3-morpholinyl, 2- or 3-tetrahydropyranyl, 2-imidazolidinyl, 2- or 3-pyrazolidinyl and the like. A phenyl radical is particularly preferred and is used illustratively herein.

When examined along its longest chain of atoms, an $R^1$ substituent, including its own substituent when present, has a total length that is greater than the corresponding length of a fully extended saturated chain of six carbon atoms (a hexyl group); i.e., a length of a heptyl chain or longer, and a length that is less than that of a fully extended saturated chain of about 20 carbons (an eicosyl group). Preferably, that length is equivalent to the length of a fully extended saturated chain of about 8 to about 18 carbon atoms, even though many more atoms may be present in ring structures or substituents. This length requirement is discussed further below.

Looked at more generally, and aside from specific moieties from which it is constructed, an $R^1$ substituent (radical, group or moiety) has a length equivalent to that of a fully extended heptyl group or greater. Such an $R^1$ substituent also has a length that is equivalent to less than that of a fully extended eicosyl group. That is to say that a $R^1$ is a substituent having a length greater than that of a saturated six carbon chain and shorter than that of a saturated twenty carbon chain, and more preferably, a length greater than that of an octyl group and less than that of a palmityl group. The radical chain lengths are measured along the longest linear atom chain in the radical, following the skeletal atoms of a ring where necessary. Each atom in the chain, e.g. carbon, oxygen or nitrogen, is presumed to be carbon for ease in calculation.

Such lengths can be readily determined by using published bond angles, bond lengths and atomic radii, as needed, to draw and measure a chain, or by building models using commercially available kits whose bond angles, lengths and atomic radii are in accord with accepted, published values. Radical (substituent) lengths can also be determined somewhat less exactly by presuming, as is done here, that all atoms have bond lengths of saturated carbon, that unsaturated and aromatic bonds have the same lengths as saturated bonds and that bond angles for unsaturated bonds are the same as those for saturated bonds, although the above-mentioned modes of measurement are preferred. For example, a 4-phenyl or 4-pyridyl group has a length of a four carbon chain, as does a propoxy group, whereas a biphenyl group has a length of about an eight carbon chain using a contemplated measurement mode.

In addition, an $R^1$ substituent, when rotated about an axis drawn through the $SO_2$-bonded 1-position and the 4-position of a 6-membered ring radical or the $SO_2$-bonded 1-position and through the 3,4 bond of a 5-membered ring radical defines a three-dimensional volume whose widest dimension has the width equivalent to from about one furanyl ring to about the width of two phenyl rings in a direction transverse to that axis of rotation.

When utilizing this width or volume criterion, a fused ring system such as a naphthyl or purinyl radical is considered to be a 6- or 5-membered ring that is substituted at appropriate positions numbered from the $SO_2$-linkage that is deemed to be at the 1-position as discussed before. Thus, a 2-naphthyl substituent or an 8-purinyl substituent is an appropriately sized $R^1$ radical as to width when examined using the above rotational width criterion. On the other hand, a 1-naphthyl group or a 7- or 9-purinyl group is too large upon rotation and is excluded.

As a consequence of these length and width requirements, $R^1$ substituents such as 4-(phenyl)phenyl [biphenyl], 4-(4'-methoxyphenyl)phenyl, 4-(phenoxy)phenyl, 4-(thiophenyl) phenyl [4-(phenylthio)phenyl], 4-(phenylazo)phenyl, 4-(phenylureido)phenyl, 4-(anilino)phenyl, 4-(nicotinamido)phenyl, 4-(isonicotinamido)phenyl, 4-(picolinamido)phenyl and 4-(benzamido)phenyl are among particularly preferred $R^1$ substituents, with 4-(phenoxy)phenyl and 4-(thiophenyl)phenyl being most preferred.

An $SO_2$-linked cyclohydrocarbyl, heterocyclo, aryl or heteroaryl radical is a 5- or 6-membered single-ring that is itself substituted with one other substituent, $R^3$. The $SO_2$-linked single-ringed cyclohydrocarbyl, heterocyclo, aryl or heteroaryl radical is $R^3$-substituted at its own 4-position when a 6-membered ring and at its own 3-position when a 5-membered ring. The cyclohydrocarbyl, heterocyclo, aryl or heteroaryl radical to which $R^3$ is bonded is preferably a phenyl group, so that $R^1$ is preferably $PhR^3$ in which $R^3$ is bonded at the 4-position of the $SO_2$-linked phenyl (Ph) radical, and in which $R^3$ can itself be optionally substituted as is discussed hereinafter. Substitution at the 2-position of a $SO_2$-linked cyclohydrocarbyl, heterocyclo, aryl or heteroaryl radical appears to greatly lessen inhibitory potency toward MMP enzymes, and is absent from a contemplated compound.

A contemplated $R^3$ substituent can be a single-ringed cyclohydrocarbyl, heterocyclo, aryl or heteroaryl group or another substituent having a chain length of 3 to about 14 carbon atoms such as a hydrocarbyl or hydrocarbyloxy group [e.g., $C_3$–$C_{14}$ hydrocarbyl or O—$C_2$–$C_{14}$ hydrocarbyl], a phenyl group, a phenoxy group [—$OC_6H_5$], a thiophenoxy group [phenylsulfanyl; —$SC_6H_5$], an anilino group [—$NHC_6H_5$], a phenylazo group [—$N_2C_6H_5$], a phenylureido group [aniline carbonylamino; —NHC(O)NH—$C_6H_5$], a benzamido group [—NHC(O)$C_6H_5$], a nicotinamido group [3-NHC(O)$C_5H_4N$], an isonicotinamido group [4-NHC(O)$C_5H_4N$], or a picolinamido group [2-NHC(O) $C_5H_4N$]. As noted before in conjunction with the discussion of $R^1$, most preferred $R^3$ substituents are phenoxy and thiophenoxy groups that are preferably themselves free of substitution. Additionally contemplated $R^3$ substituent groups include a heterocyclo, heterocyclohydrocarbyl, arylheterocyclohydrocarbyl, arylhydrocarbyl, heteroarylhydrocarbyl, heteroarylheterocyclohydrocarbyl, arylhydrocarbyloxyhydrocarbyl, aryloxyhydrocarbyl, hydrocarboylhydrocarbyl, arylhydrocarboylhydrocarbyl, arylcarbonylhydrocarbyl, arylazoaryl, arylhydrazinoaryl, hydrocarbylthiohydrocarbyl, hydrocarbylthioaryl, arylthiohydrocarbyl, heteroarylthiohydrocarbyl, hydrocarbylthioarylhydrocarbyl, arylhydrocarbylthiohydrocarbyl, arylhydrocarbylthioaryl, arylhydrocarbylamino, heteroarylhydrocarbylamino, or a heteroarylthio group.

A contemplated $R^3$ substituent can itself also be substituted with one or more substituent radicals at the meta- or para-position or both of a six-membered ring with a single atom or a substituent containing a longest chain of up to ten atoms, excluding hydrogen. Exemplary substituent radicals include a halo, hydrocarbyl, hydrocarbyloxy, nitro, cyano, perfluorohydrocarbyl, trifluoromethylhydrocarbyl, hydroxy, mercapto, hydroxycarbonyl, aryloxy, arylthio, arylamino, arylhydrocarbyl, aryl, heteroaryloxy, heteroarylthio, heteroarylamino, heteroarylhydrocarbyl, hydrocarbyloxycarbonylhydrocarbyl, heterocyclooxy, hydroxycarbonylhydrocarbyl, heterocyclothio, heterocycloamino, cyclohydrocarbyloxy, cyclohydrocarbylthio, cyclohydrocarbylamino, heteroarylhydrocarbyloxy, heteroarylhydrocarbylthio, heteroarylhydrocarbylamino, arylhydrocarbyloxy, arylhydrocarbylthio, arylhydrocarbylamino, heterocyclic, heteroaryl, hydroxycarbonylhydrocarbyloxy, alkoxycarbonylalkoxy, hydrocarbyloyl, arylcarbonyl, arylhydrocarbyloyl, hydrocarboyloxy, arylhydrocarboyloxy, hydroxyhydrocarbyl, hydroxyhydrocarbyloxy, hydrocarbylthio, hydrocarbyloxyhydrocarbylthio, hydrocarbyloxycarbonyl, hydroxycarbonylhydrocarbyloxy, hydrocarbyloxycarbonylhydrocarbyl, hydrocarbylhydroxycarbonylhydrocarbylthio, hydrocarbyloxycarbonylhydrocarbyloxy, hydrocarbyloxycarbonylhydrocarbylthio, amino, hydrocarbylcarbonylamino, arylcarbonylamino, cyclohydrocarbylcarbonylamino, heterocyclohydrocarbylcarbonylamino, arylhydrocarbylcarbonylamino, heteroarylcarbonylamino, heteroarylhydrocarbylcarbonylamino, heterocyclohydrocarbyloxy, hydrocarbylsulfonylamino, arylsulfonylamino, arylhydrocarbylsulfonylamino, heteroarylsulfonylamino, heteroarylhydrocarbylsulfonylamino, cyclohydrocarbylsulfonylamino, heterocyclohydrocarbylsulfonylamino and N-monosubstituted or N,N-disubstituted aminohydrocarbyl group wherein the substituent(s) on the nitrogen are selected from the group consisting of hydrocarbyl, aryl, arylhydrocarbyl, cyclohydrocarbyl, arylhydrocarbyloxycarbonyl, hydrocarbyloxycarbonyl, and hydrocarboyl, or wherein the nitrogen and two substituents attached thereto form a 5- to 8-membered heterocyclic or heteroaryl ring group.

Thus, initial studies indicate that so long as the length, substitution and width (volume upon rotation) requirements of an $SO_2$-linked $R^1$ substituent discussed herein are met, an $R^1$ substituent can be extremely varied.

A particularly preferred $R^3$ substituent of an $SO_2$-linked Ph group is a single-ringed aryl or heteroaryl, phenoxy, thiophenoxy, phenylazo, phenylureido, nicotinamido, isonicotinamido, picolinamido, anilino or benzamido group that is unsubstituted or is itself substituted (optionally substituted) at the para-position when a 6-membered ring or the 3-position when a 5-membered ring. Here, single atoms such as halogen moieties or substituents that contain one to a chain of about ten atoms other than hydrogen such as $C_1-C_{10}$ hydrocarbyl, $C_1-C_9$ hydrocarbyloxy or carboxyethyl groups can be used.

Exemplary particularly preferred substituted $PhR^3$ (particularly preferred substituted $R^1$) substituents include biphenyl, 4-phenoxyphenyl, 4-thiophenoxyphenyl, 4-benzamidophenyl, 4-phenylureido, 4-anilinophenyl, 4-nicotinamido, 4-isonicotinamido, and 4-picolinamido. Exemplary particularly preferred $R^3$ groups contain a 6-membered aromatic ring and include a phenyl group, a phenoxy group, a thiophenoxy group, a phenylazo group, a phenylureido group, an anilino group, a nicotinamido group, an isonicotinamido group, a picolinamido group and a benzamido group.

More specifically, a particularly preferred sulfonyl butanhydroxamate compound has an $R^3$ substituent that is a phenyl group, a phenoxy group, a thiophenoxy group, a phenylazo group, a phenylureido group, an anilino group, a nicotinamido group, an isonicotinamido group, a picolinamido group or a benzamido group that is itself optionally substituted at its own meta or para-position or both with a moiety that is selected from the group consisting of a halogen, a $C_1-C_9$ hydrocarbyloxy (—O—$C_1-C_9$ hydrocarbyl) group, a $C_1-C_{10}$ hydrocarbyl group, a di-$C_1-C_9$ hydrocarbylamino [—N($C_1-C_9$ hydrocarbyl)($C_1-C_9$ hydrocarbyl)] group, a carboxyl $C_1-C_8$ hydrocarbyl ($C_1-C_8$ hydrocarbyl-$CO_2H$) group, a $C_1-C_4$ hydrocarbyloxy carbonyl $C_1-C_4$ hydrocarbyl [$C_1-C_4$ hydrocarbyl-O—(CO)—$C_1-C_4$ hydrocarbyl] group, a $C_1-C_4$ hydrocarbyloxycarbonyl $C_1-C_4$ hydrocarbyl [$C_1-C_4$ hydrocarbyl (CO)—O—$C_1-C_4$ hydrocarbyl] group and a $C_1-C_8$ hydrocarbyl carboxamido [—NH(CO)—$C_1-C_8$ hydrocarbyl] group, or is substituted at the meta- and para-positions by two methyl groups or by a $C_1-C_2$ alkylenedioxy group such as a methylenedioxy group.

Inasmuch as a contemplated $SO_2$-linked cyclohydrocarbyl, heterocyclo, aryl or heteroaryl radical is itself preferably substituted with a 6-membered aromatic ring, two nomenclature systems are used together herein for ease in understanding substituent positions. The first system uses position numbers for the ring directly bonded to the $SO_2$-group, whereas the second system uses ortho, meta or para for the position of one or more substituents of a 6-membered ring bonded to a $SO_2$-linked cyclohydrocarbyl, heterocyclo, aryl or heteroaryl radical. When an $R^3$ substituent is other than a 6-membered ring, substituent positions are numbered from the position of linkage to the aromatic or heteroaromatic ring. Formal chemical nomenclature is used in naming particular compounds.

Thus, the 1-position of an above-discussed $SO_2$-linked cyclohydrocarbyl, heterocyclo, aryl or heteroaryl radical is the position at which the $SO_2$-group is bonded to the ring. The 4- and 3-positions of rings discussed here are numbered from the sites of substituent bonding from the $SO_2$-linkage as compared to formalized ring numbering positions used in heteroaryl nomenclature.

In particularly preferred practice, the alpha-cycloamino substituent is a 4-piperidinyl group, and a contemplated compound has a structure that corresponds to Formula II, below, wherein $R^2$ and $R^1$ are as before defined.

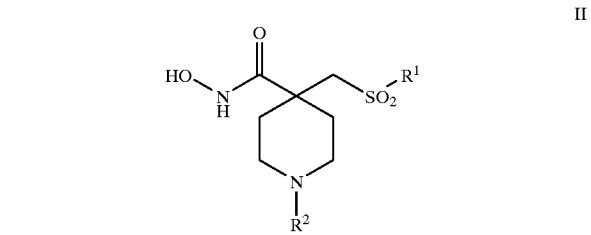

II

As noted before, it is also particularly preferred that $R^1$ contain a phenyl group (Ph) linked at its own 4-position to another substituent, $R^3$, so that $R^1$ is $PhR^3$. A most preferred compound has a structure that corresponds to Formula III, below, wherein $R^2$ and $R^3$ are as defined before.

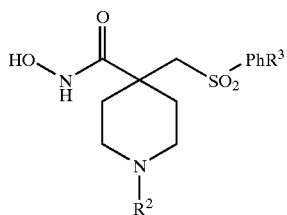

III

Yet another preferred compound corresponds in structure to a compound of Formula IV, below, wherein $R^2$ and $R^1$ are as defined before. Again, $R^1$ is $PhR^3$ in particularly preferred practice, wherein $PhR^3$ is as defined before.

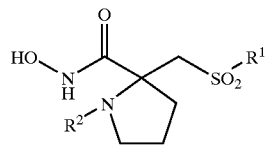

IV

The length of a $R^1$ substituent bonded to the $SO_2$ group is believed to play a role in the overall activity of a contemplated inhibitor compound against MMP enzymes generally. Thus, a compound having an $R^1$ substituent that is shorter in length than an octyl group, e.g., a 4-methoxyphenyl group, typically exhibits moderate to poor inhibitory activity against all of the MMP enzymes, whereas compounds whose $R^1$ substituents have a length of about an octyl chain or longer, e.g., a 4-phenoxyphenyl group that has a length of about a nine-carbon chain, typically exhibit good to excellent potencies against MMP-13 or MMP-2 and also selectivity against MMP-1. Exemplary data for some of those latter compounds are provided in Table 13 hereinafter.

The identity of the $R^1$ substituent group can also play a role in the activity of a compound as an inhibitor of particular MMP enzymes. For example, the compound of Example 1, N-hydroxy-4-[[[4-(benzoylamino)phenyl]sulfonyl]methyl]-4-piperidinecarboxamide, monohydrochloride, whose $SO_2$-bonded aryl group is a phenyl substituent bonded to a benzamido moiety is virtually unbound by MMP-1, while exhibiting excellent activity against MMP-2 and moderate activity against MMP-13. These comparative activities can be seen in Table 13 hereinafter.

The word "hydrocarbyl" is used herein as a short hand term to include straight and branched chain aliphatic as well as alicyclic groups or radicals that contain only carbon and hydrogen. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups or radicals, as discussed hereinafter. Where a specific aliphatic hydrocarbyl substituent group is intended, that group is recited; i.e., $C_1$–$C_4$ alkyl, methyl or dodecenyl. Exemplary hydrocarbyl groups contain a chain of 1 to about 12 carbon atoms, and preferably one to about 10 carbon atoms. A particularly preferred hydrocarbyl group is an alkyl group.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. On the other hand, a hydrocarbyl group containing a —C(O)O— functionality is referred to as a hydrocarboyl group inasmuch as there is no ambiguity in using that suffix. As a skilled worker will understand, a substituent that cannot exist such as a $C_1$ alkenyl group is not intended to be encompassed by the word "hydrocarbyl".

As stated before, a particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl, pentyl, iso-amyl, hexyl, octyl and the like. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like. Examples of alkynyl radicals include ethynyl, 2-propynyl, 3-propynyl, decynyl, 1-butynyl, 2-butynyl, 3-butynyl, and the like.

The term "carbonyl", alone or in combination, means a —C(=O)— group wherein the remaining two bonds (valences) are independently substituted. The term "thiol" or "sulfhydryl", alone or in combination, means a —SH group. The term "thio" or "thia", alone or in combination, means a thiaether group; i.e., an ether group wherein the ether oxygen is replaced by a sulfur atom.

The term "amino", alone or in combination, means an amine or —NH$_2$ group, whereas the term mono-substituted amino, alone or in combination, means a substituted amine —N(H) (substituent) group wherein one hydrogen atom is replaced with a substituent, and disubstituted amine means a —N(substituent)$_2$ wherein two hydrogen atoms of the amino group are replaced with independently selected substituent groups. Amines, amino groups and amides are classes that can be designated as primary (I°), secondary (II°) or tertiary (III°) or unsubstituted, mono-substituted or di-substituted depending on the degree of substitution of the amino nitrogen. Quaternary amine (IV°) means a nitrogen with four substituents (—N$^+$ (substituent)$_4$) that is positively charged and accompanied by a counter ion or N-oxide means one substituent is oxygen and the group is represented as (—N$^+$ (substituent)$_3$—O$^-$); i.e., the charges are internally compensated.

The term "cyano", alone or in combination, means a —C-triple bond-N (—CN)group. The term "azido", alone or in combination, means a —N-double bond-N-double bond-N (—N=N=N) group.

The term "hydroxyl", alone or in combination, means a —OH group. The term "nitro", alone or in combination, means a —NO$_2$ group.

The term "azo", alone or in combination, means a —N=N— group wherein the bonds at the terminal positions are independently substituted. The term "hydrazino", alone or in combination, means a —NH—NH— group wherein the remaining two bonds (valences) are independently substituted. The hydrogen atoms of the hydrazino group can be replaced, independently, with substituents and the nitrogen atoms can form acid addition salts or be quaternized.

The term "sulfonyl", alone or in combination, means a —S(=O)$_2$— group wherein the remaining two bonds (valences) can be independently substituted. The term "sulfoxido", alone or in combination, means a —S(=O)$_1$— group wherein the remaining two bonds (valences) can be independently substituted. The term "sulfonylamide", alone or in combination, means a —S(=O)$_2$—N= group wherein the remaining three bonds (valences) are independently substituted. The term "sulfinamido", alone or in combination, means a —S(=O)$_1$N= group wherein the remaining three bonds (valences) are independently substituted. The term "sulfenamide", alone or in combination, means a —S—N= group wherein the remaining three bonds (valences) are independently substituted.

The term "hydrocarbyloxy", alone or in combination, means a hydrocarbyl ether radical wherein the term hydrocarbyl is as defined above. Examples of suitable hydrocarbyl ether radicals include methoxy, ethoxy, n-propoxy, isopropoxy, allyloxy, n-butoxy, iso-butoxy, sec-butoxy, tert-butoxy and the like. The term "cyclohydrocarbyl", alone or in combination, means a hydrocarbyl radical that contains 3 to about 8 carbon atoms, preferably from about 3 to about 6 carbon atoms, and is cyclic. Examples of such cyclohydrocarbyl radicals include cyclopropyl, cyclobutyl, cyclopentenyl, cyclohexyl, cyclooctynyl and the like. The term "cyclohydrocarbylhydrocarbyl" means an hydrocarbyl radical as defined above which is substituted by a cyclohydrocarbyl as also defined above.

The term "aryl", alone or in combination, means a phenyl or naphthyl radical that optionally carries one or more substituents selected from hydrocarbyl, hydrocarbyloxy, halogen, hydroxy, amino, nitro and the like, such as phenyl, p-tolyl, 4-methoxyphenyl, 4-(tert-butoxy)phenyl, 4-fluorophenyl, 4-chlorophenyl, 4-hydroxyphenyl, and the like. The term "arylhydrocarbyl", alone or in combination, means an hydrocarbyl radical as defined above in which one hydrogen atom is replaced by an aryl radical as defined above, such as benzyl, 2-phenylethyl and the like. The term "arylhydrocarbyloxycarbonyl", alone or in combination, means a radical of the formula —C(O)—O— arylhydrocarbyl in which the term "arylhydrocarbyl" has the significance given above. An example of an arylhydrocarbyloxycarbonyl radical is benzyloxycarbonyl. The term "aryloxy" means a radical of the formula aryl-O— in which the term aryl has the significance given above. The term "aromatic ring" in combinations such as substituted-aromatic ring sulfonamide, substituted-aromatic ring sulfinamide or substituted-aromatic ring sulfenamide means aryl or heteroaryl as defined above.

The terms "hydrocarbyloyl" or "hydrocarbylcarbonyl", alone or in combination, mean an acyl radical derived from an hydrocarbylcarboxylic acid, examples of which include acetyl, propionyl, acryloyl, butyryl, valeryl, 4-methylvaleryl, and the like. The term "cyclohydrocarbylcarbonyl" means an acyl group derived from a monocyclic or bridged cyclohydrocarbylcarboxylic acid such as cyclopropanecarbonyl, cyclohexenecarbonyl, adamantanecarbonyl, and the like, or from a benz-fused monocyclic cyclohydrocarbylcarboxylic acid that is optionally substituted by, for example, a hydrocarbyloylamino group, such as 1,2,3,4-tetrahydro-2-naphthoyl, 2-acetamido-1,2,3,4-tetrahydro-2-naphthoyl. The terms "arylhydrocarbyloyl" or "arylhydrocarbylcarbonyl" mean an acyl radical derived from an aryl-substituted hydrocarbylcarboxylic acid such as phenylacetyl, 3-phenylpropenyl (cinnamoyl), 4-phenylbutyryl, (2-naphthyl)acetyl, 4-chlorohydrocinnamoyl, 4-aminocinnamoyl, 4-methoxycinnamoyl and the like.

The terms "aroyl" or "arylcarbonyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl) benzoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The heterocyclyl (heterocyclo) or heterocyclohydrocarbyl portion of a heterocyclylcarbonyl, heterocyclyloxycarbonyl, heterocyclylhydrocarbyloxycarbonyl, or heterocyclohydrocarbyl group or the like is a saturated or partially unsaturated monocyclic, bicyclic or tricyclic heterocycle that contains one to four hetero atoms selected from nitrogen, oxygen and sulphur, which is optionally substituted on one or more carbon atoms by a halogen, alkyl, alkoxy, oxo group, and the like, and/or on a secondary nitrogen atom (i.e., —NH—) by an hydrocarbyl, arylhydrocarbyloxycarbonyl, hydrocarbyloyl, aryl or arylhydrocarbyl or on a tertiary nitrogen atom (i.e. =N—) by oxido and that is attached via a carbon atom. The tertiary nitrogen atom with three substituents can also form a N-oxide [=N(O)—] group. Examples of such heterocyclyl groups are pyrrolidinyl, piperidinyl, piperazinyl, morpholinyl, thiamorpholinyl, and the like.

The heteroaryl portion of a heteroaroyl, heteroaryloxycarbonyl, or a heteroarylhydrocarbyloyl (heteroarylhydrocarbyl carbonyl) group or the like is an aromatic monocyclic, bicyclic, or tricyclic heterocycle that contains the hetero atoms and is optionally substituted as defined above with respect to the definition of heterocyclyl. A "heteroaryl" group is an aromatic heterocyclic ring substituent that can contain one, two, three or four atoms in the ring that are other than carbon. Those heteroatoms can be nitrogen, sulfur or oxygen. A heteroaryl group can contain a single five- or 6-membered ring or a fused ring system that contains two 6-membered rings or a five- and a 6-membered ring. Exemplary heteroaryl groups include 6-membered ring substituents such as pyridyl, pyrazyl, pyrimidinyl, and pyridazinyl; 5-membered ring substituents such as 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2, 5-, or 1,3,4-oxadiazolyl and isothiazolyl groups; six/five-membered fused ring substituents such as benzothiofuranyl, isobenzothiofuranyl, benzisoxazolyl, benzoxazolyl, purinyl and anthranilyl groups; and six/six-membered fused rings such as 1,2-, 1,4-, 2,3- and 2,1-benzopyronyl, quinolinyl, isoquinolinyl, cinnolinyl, quinazolinyl, and 1,4-enzoxazinyl groups.

The term "cyclohydrocarbylhydrocarbyloxycarbonyl" means an acyl group derived from a cyclohydrocarbylhydrocarbyloxycarboxylic acid of the formula cyclohydrocarbylhydrocarbyl-O—COOH wherein cyclohydrocarbylhydrocarbyl has the significance given above. The term "aryloxyhydrocarbyloyl" means an acyl radical of the formula aryl-O-hydrocarbyloyl wherein aryl and hydrocarbyloyl have the significance given above. The term "heterocyclyloxycarbonyl", means an acyl group derived from heterocyclyl-O—COOH wherein heterocyclyl is as defined above. The term "heterocyclylhydrocarbyloyl" is an acyl radical derived from a heterocyclyl-substituted hydrocarbylcarboxylic acid wherein heterocyclyl has the significance given above. The term "heterocyclylhydrocarbyloxycarbonyl" means an acyl radical derived from a heterocyclyl-substituted hydrocarbyl-O—COOH wherein heterocyclyl has the significance given above. The term "heteroaryloxycarbonyl" means an acyl radical derived from a carboxylic acid represented by heteroaryl-O—COOH wherein heteroaryl has the significance given above.

The term "aminocarbonyl" alone or in combination, means an amino-substituted carbonyl (carbamoyl) group derived from an amino-substituted carboxylic acid wherein the amino group can be a primary, secondary or tertiary amino group containing substituents selected from hydrogen, hydrocarbyl, aryl, aralkyl, cyclohydrocarbyl, cyclohydrocarbylhydrocarbyl radicals and the like. The term "aminohydrocarbyloyl" means an acyl group derived from an amino-substituted hydrocarbylcarboxylic acid wherein the amino group can be a primary, secondary or tertiary amino group containing substituents independently selected from hydrogen, alkyl, aryl, aralkyl, cyclohydrocarbyl, cyclohydrocarbylhydrocarbyl radicals and the like.

The term "halogen" means fluorine, chlorine, bromine or iodine. The term "halohydrocarbyl" means a hydrocarbyl radical having the significance as defined above wherein one or more hydrogens are replaced with a halogen. Examples of such halohydrocarbyl radicals include chloromethyl, 1-bromoethyl, fluoromethyl, difluoromethyl, trifluoromethyl, 1,1,1-trifluoroethyl and the like. The term perfluorohydrocarbyl means a hydrocarbyl group wherein each hydrogen has been replaced by a fluorine atom. Examples of such perfluorohydrocarbyl groups, in addition to trifluoromethyl above, are perfluorobutyl, perfluoroisopropyl, perfluorododecyl and perfluorodecyl.

Table 1 through Table 12, below, show several contemplated aromatic sulfonyl alpha-cycloamino hydroxamic acid compounds as structural formulas that illustrate substituent groups. Each group of compounds is illustrated by a generic formula, followed by a series of preferred moieties or groups that constitute various substituents that can be attached at the position clearly shown in the generic structure. The substituent symbols, e.g., $R^1$ and $R^2$, are as shown in each Table. One bond (straight line) is shown with those substituents to indicate the respective positions of attachment in the illustrated compound. This system is well known in the chemical communication arts and is widely used in scientific papers and presentations.

TABLE 1

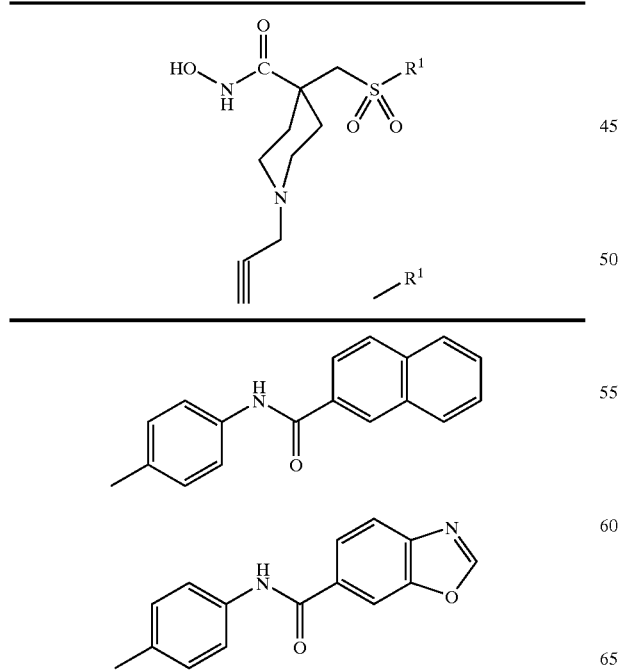

TABLE 1-continued

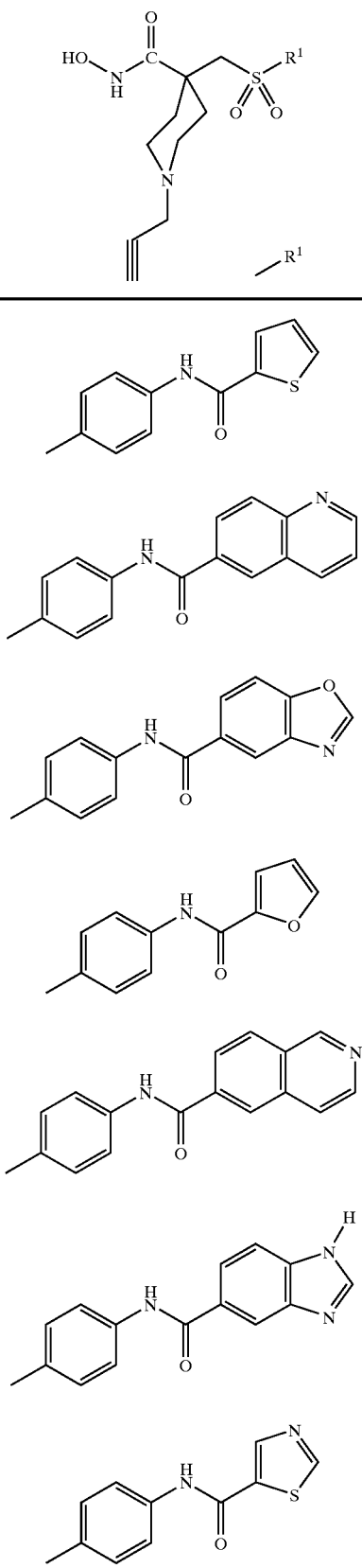

TABLE 1-continued
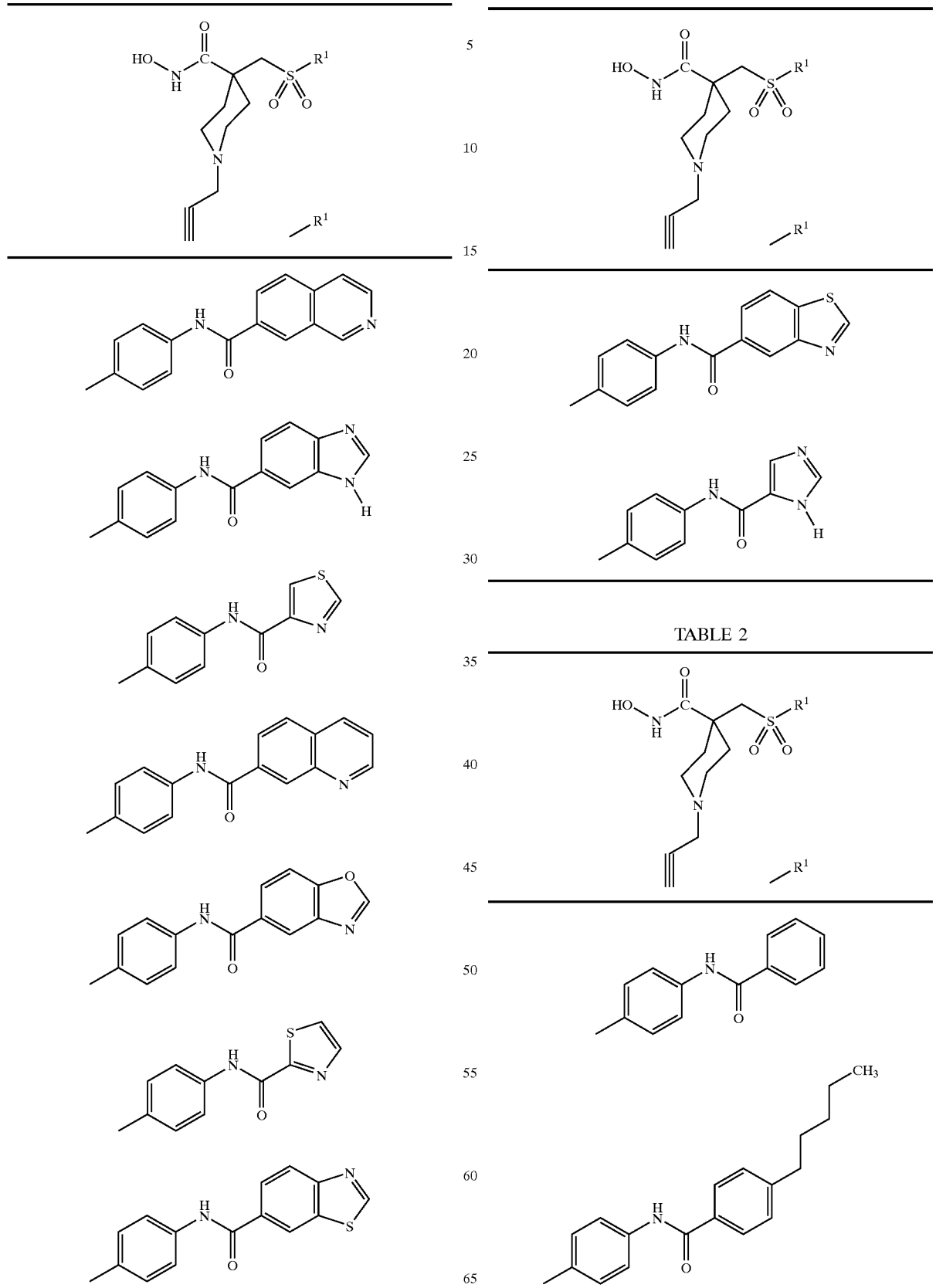
TABLE 2
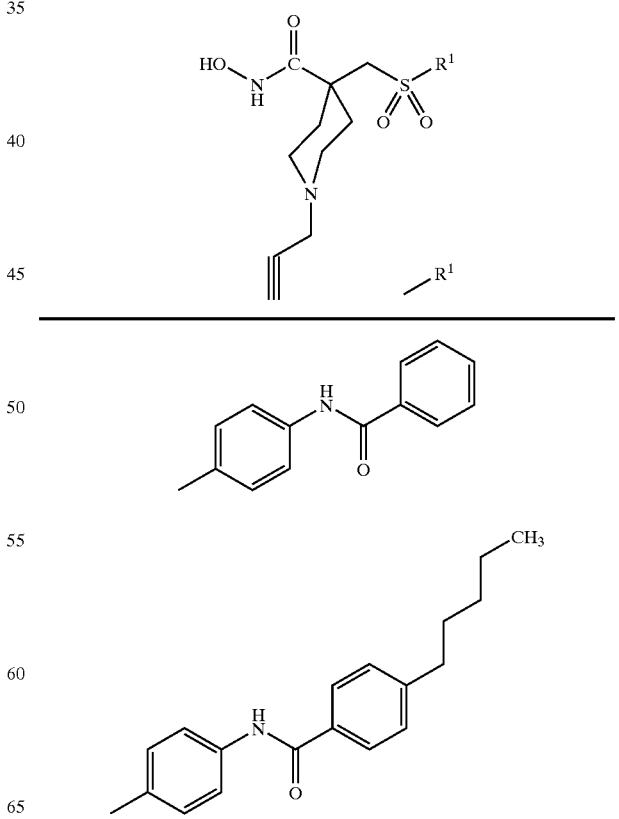

TABLE 2-continued
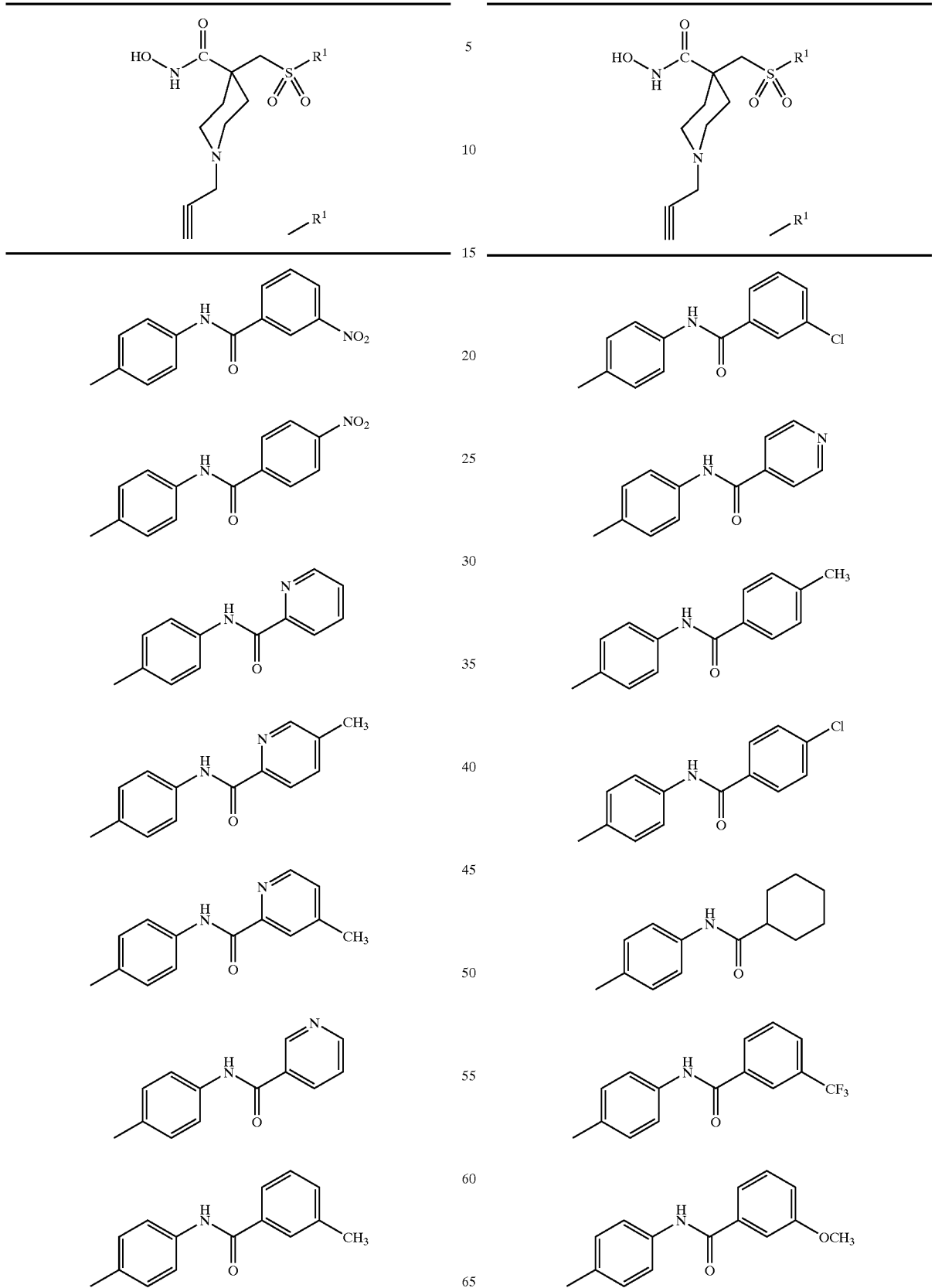

TABLE 2-continued
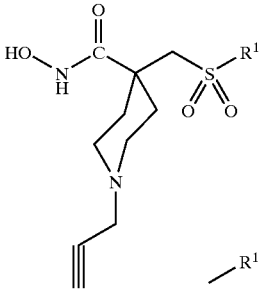
| | —R¹ |
|---|---|
| 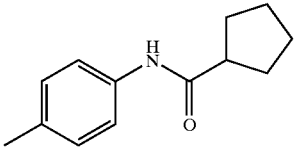 | |
| 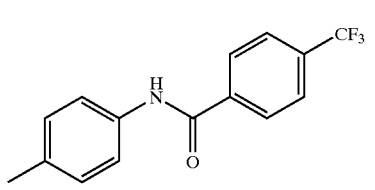 | |
| 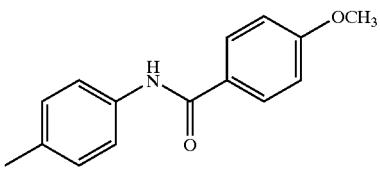 | |
| 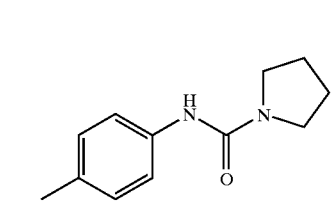 | |
| 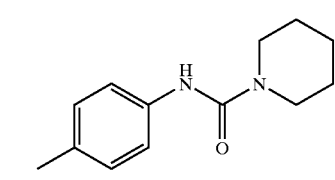 | |
| 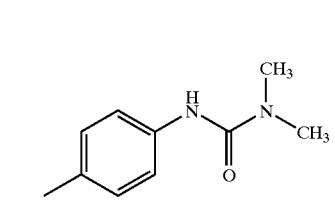 | |
TABLE 3
| | —R¹ |
|---|---|
| 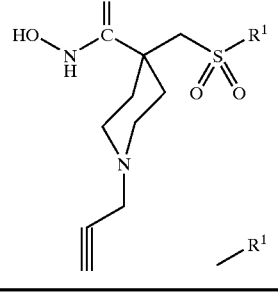 | |
| 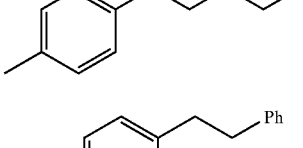 | |
| 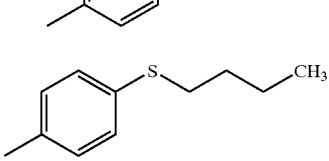 | |
| 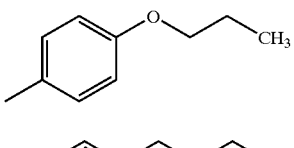 | |
| 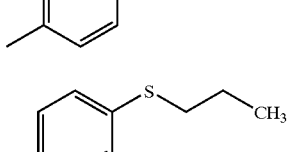 | |
| 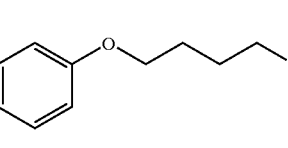 | |
| 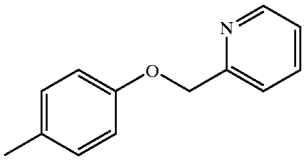 | |
| 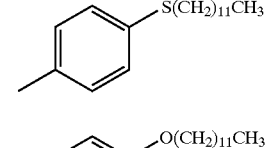 | |
| 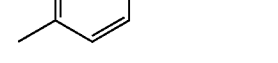 | |
|  | |

TABLE 3-continued
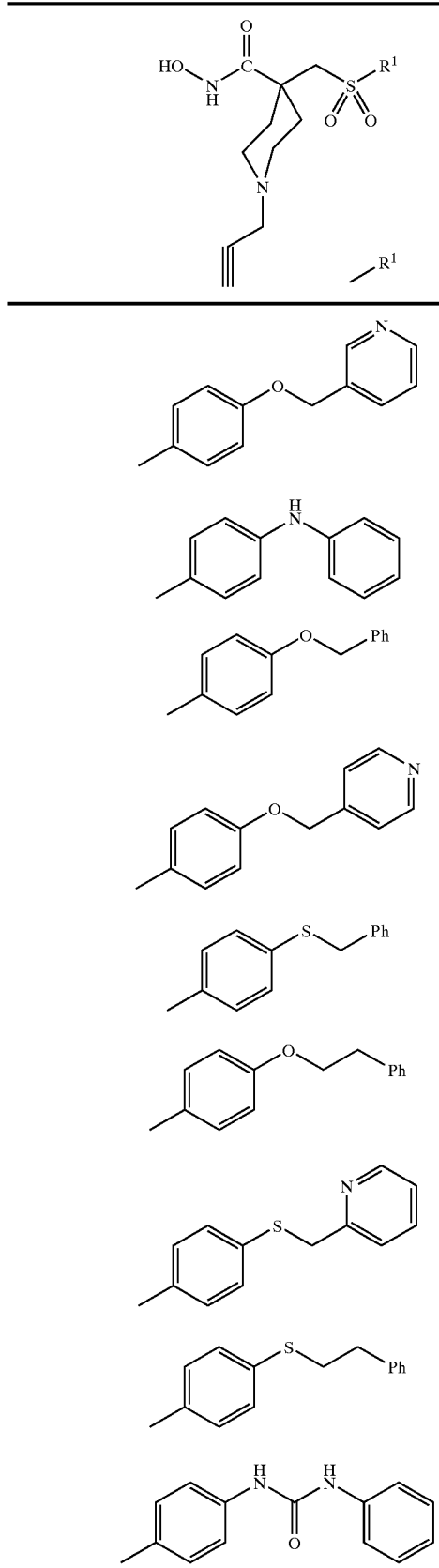
TABLE 3-continued
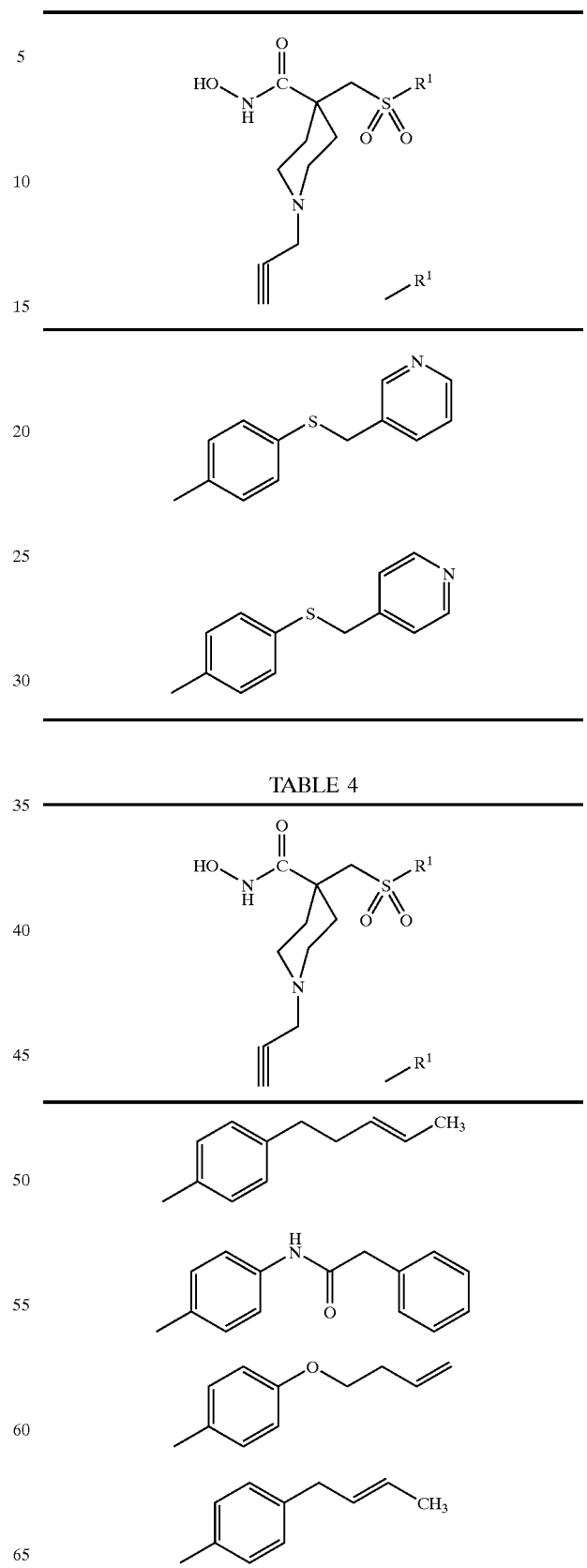

TABLE 4-continued
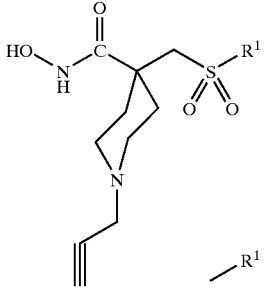
| R¹ |
|---|
| 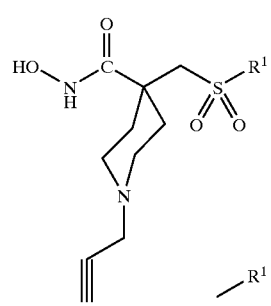 |
| 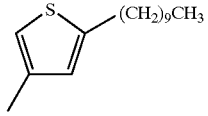 |
| 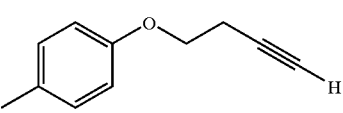 |
| 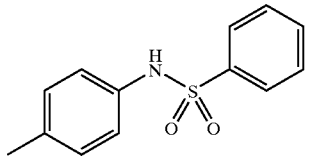 |
| 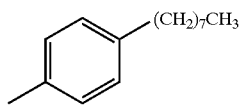 |
| 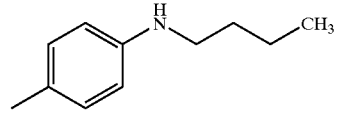 |
| 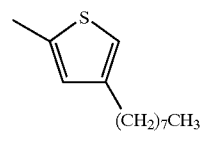 |
| 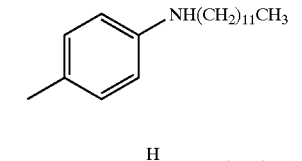 |
| 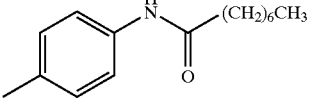 |
| 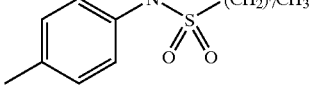 |
TABLE 4-continued
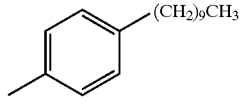
| R¹ |
|---|
| 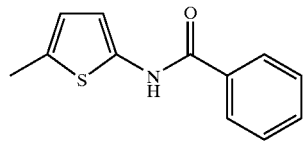 |
| 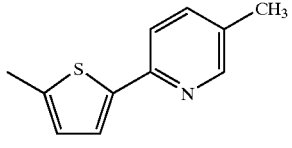 |
| 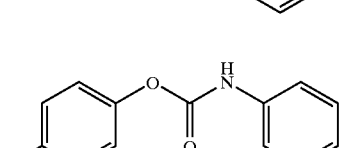 |
| 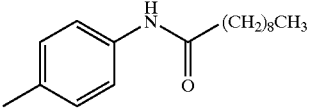 |
| 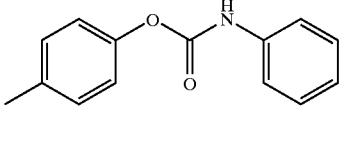 |
| 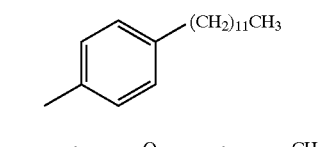 |
| 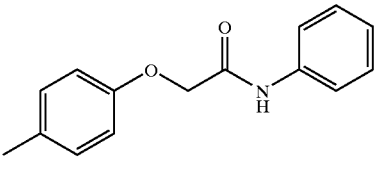 |
|  |
| 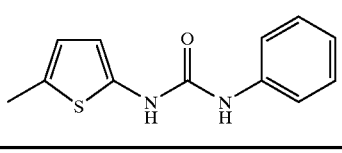 |

TABLE 5
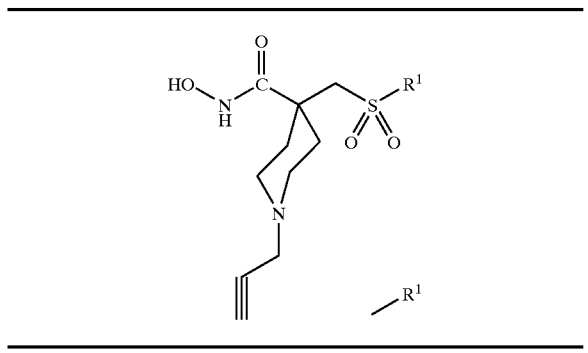
| | |
|---|---|
| | —R¹ |
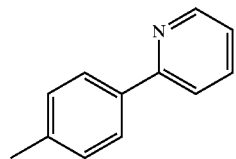
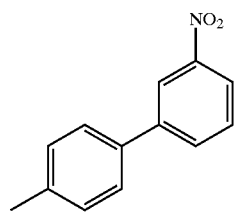
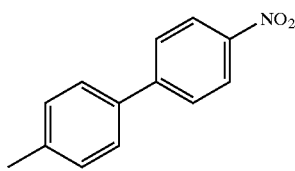
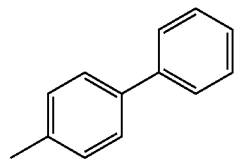
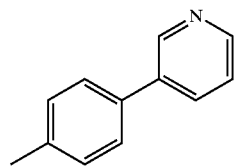
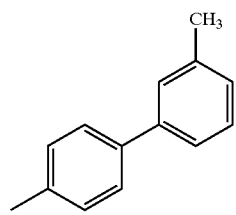
TABLE 5-continued
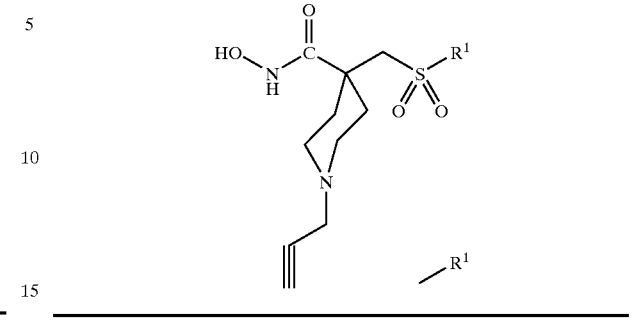
| | |
|---|---|
| | —R¹ |
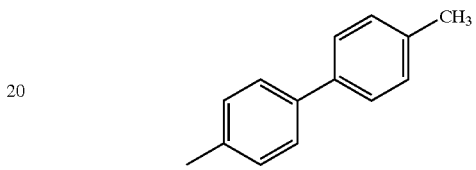
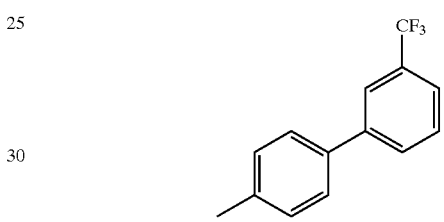
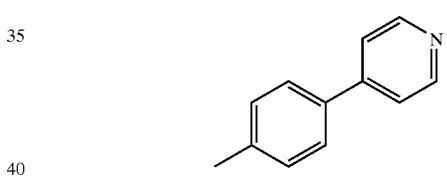
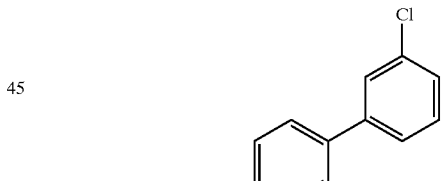
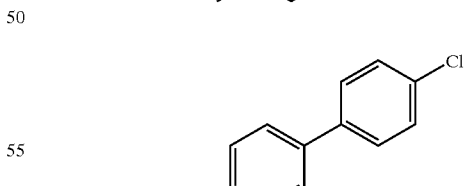
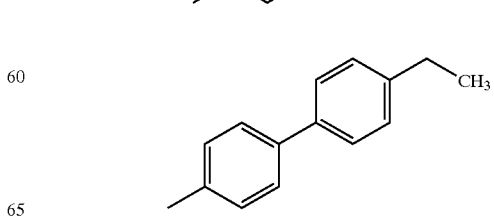

TABLE 5-continued
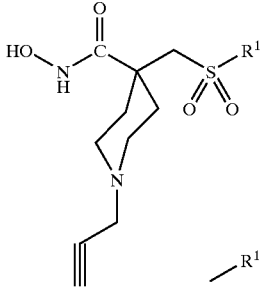
TABLE 5-continued
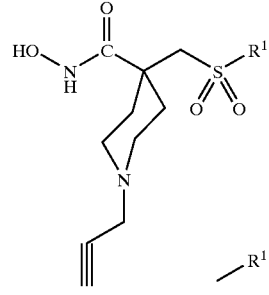
TABLE 6
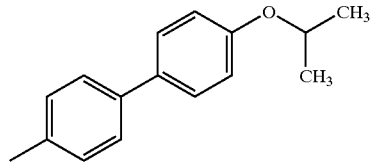

TABLE 6-continued
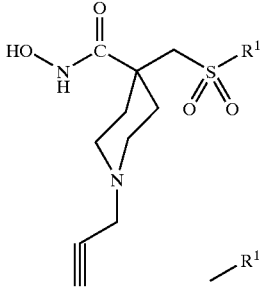
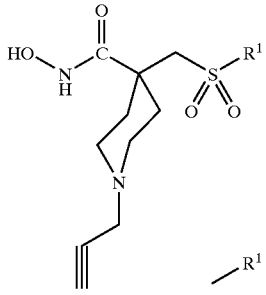
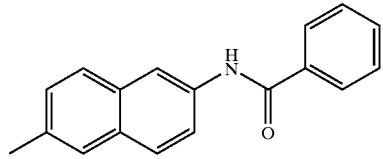
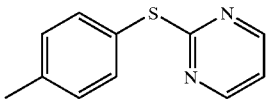
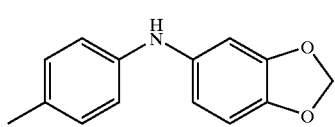
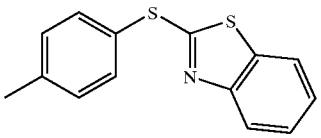
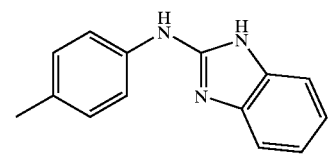
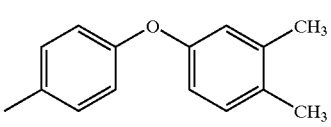
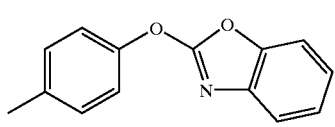
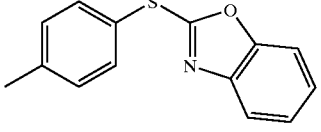
TABLE 6-continued
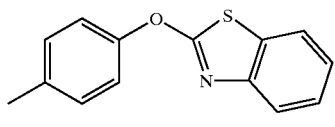
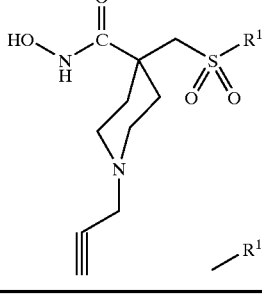
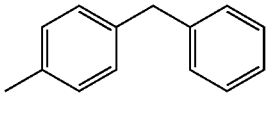
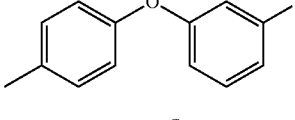
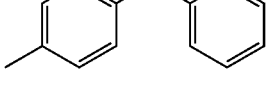
TABLE 7

TABLE 7-continued
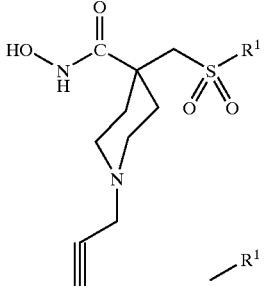

TABLE 7-continued
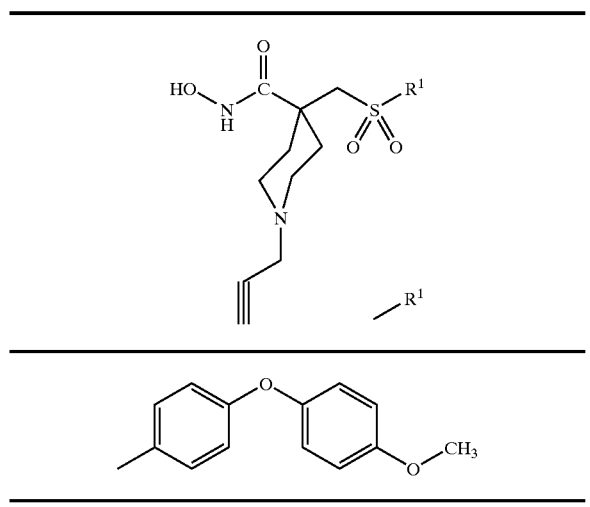
TABLE 8
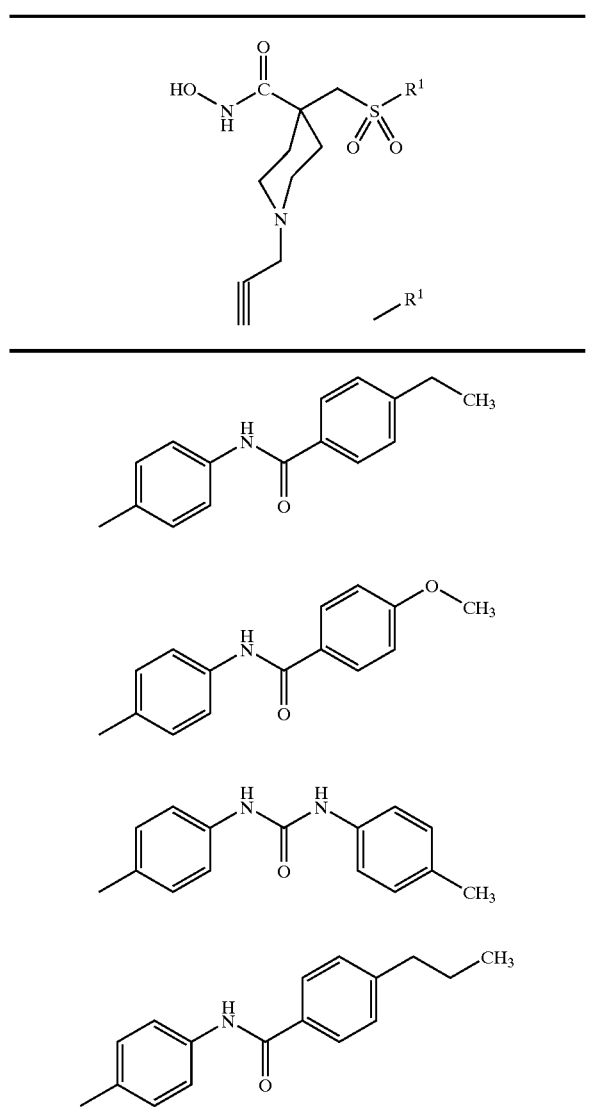
TABLE 8-continued
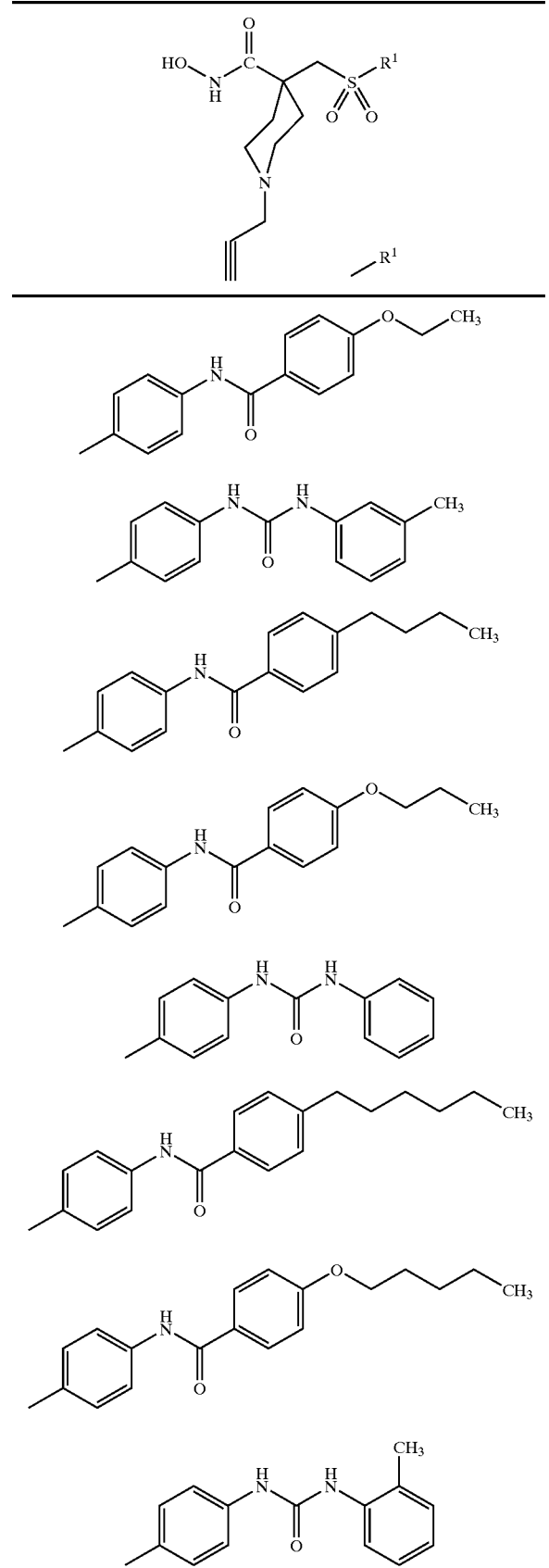

TABLE 8-continued
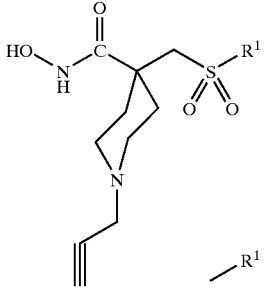
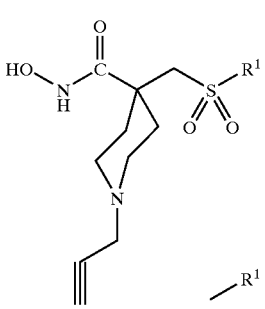
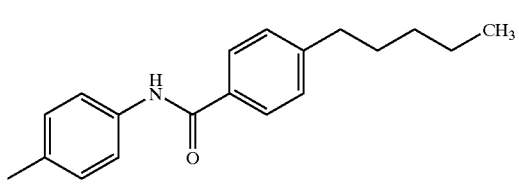
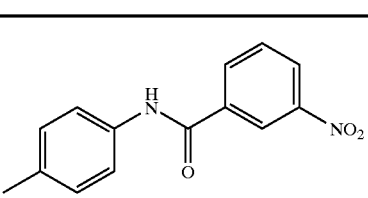
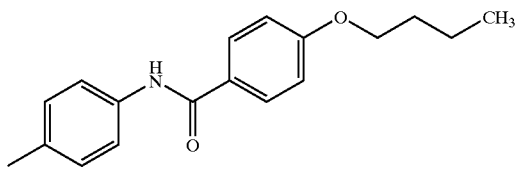
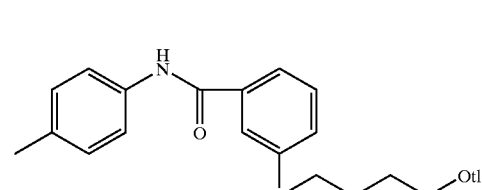
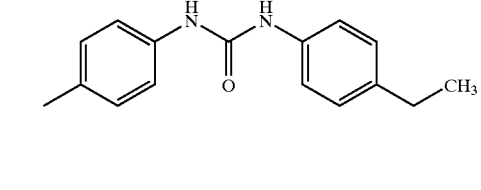
TABLE 8-continued
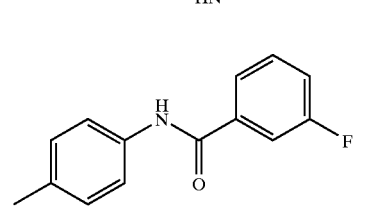
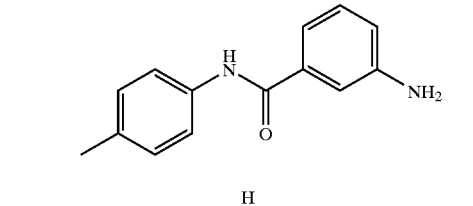
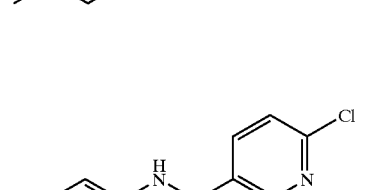
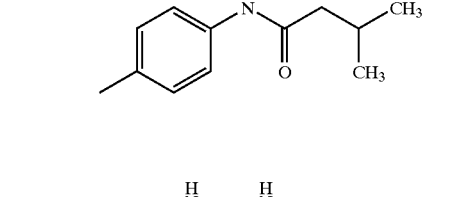
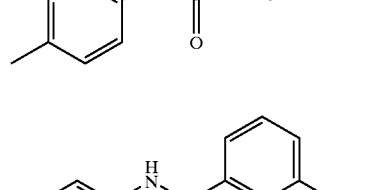
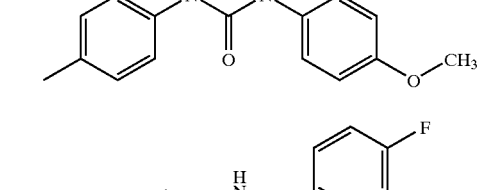

TABLE 9
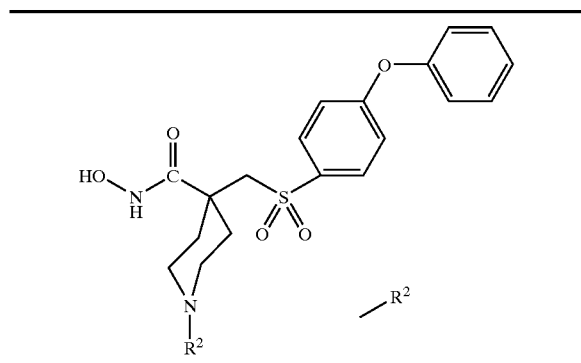
R²
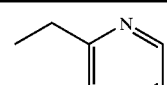
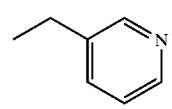
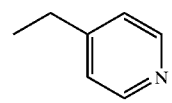
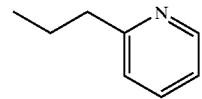
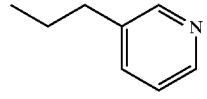
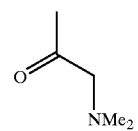
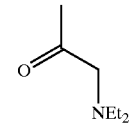
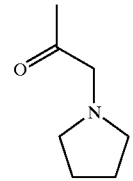
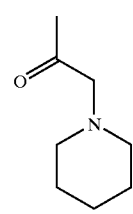
TABLE 9-continued
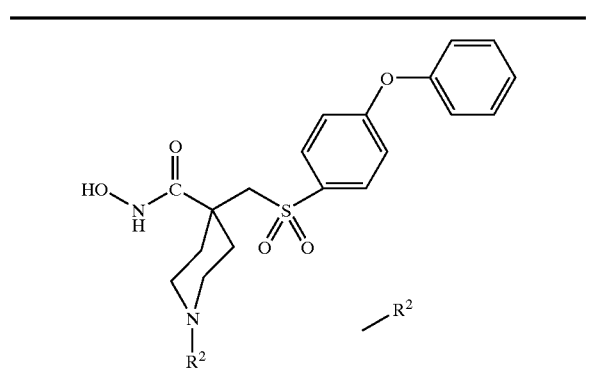
R²
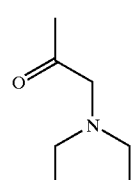
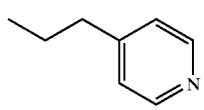
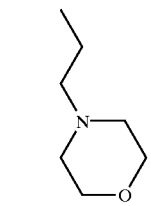
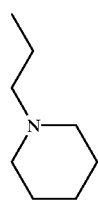
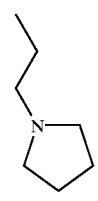
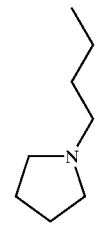

TABLE 9-continued
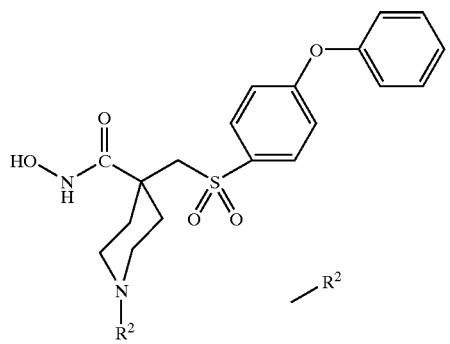
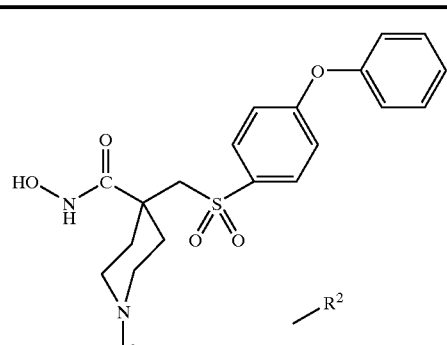
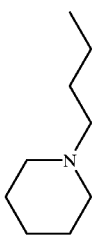
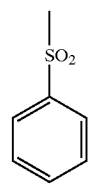
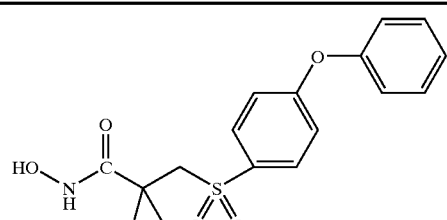
TABLE 9-continued
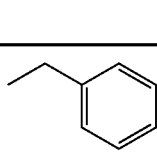
TABLE 10
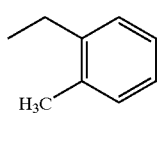
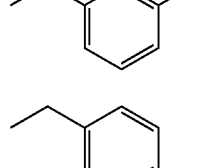

TABLE 10-continued
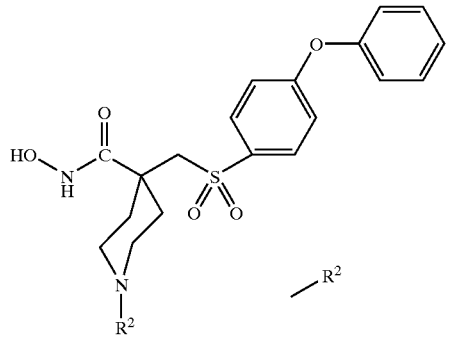
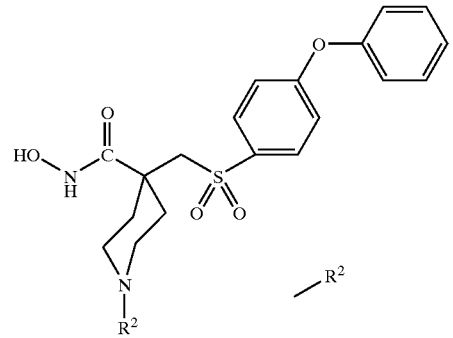
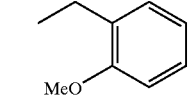
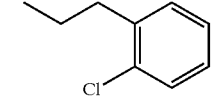
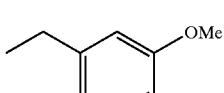
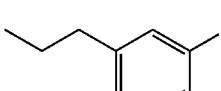
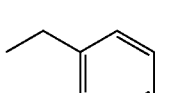
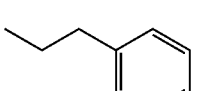
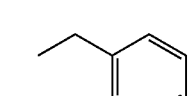
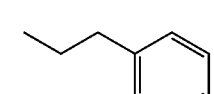
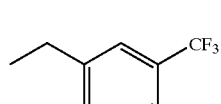
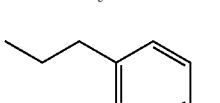
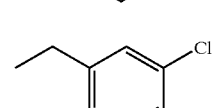
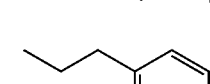
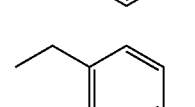
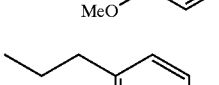
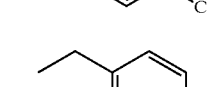
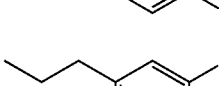
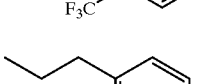
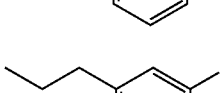
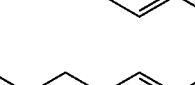
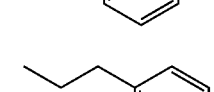

TABLE 10-continued
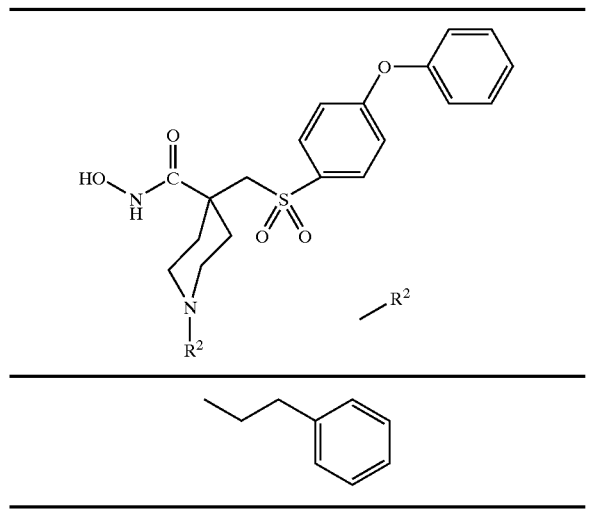
TABLE 11
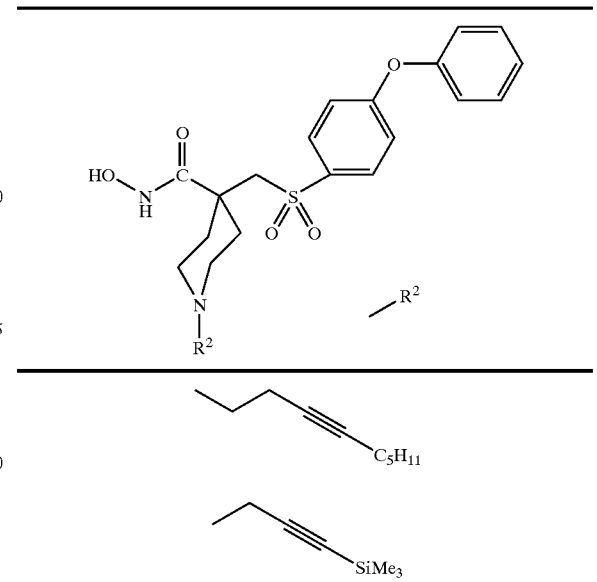
TABLE 11-continued
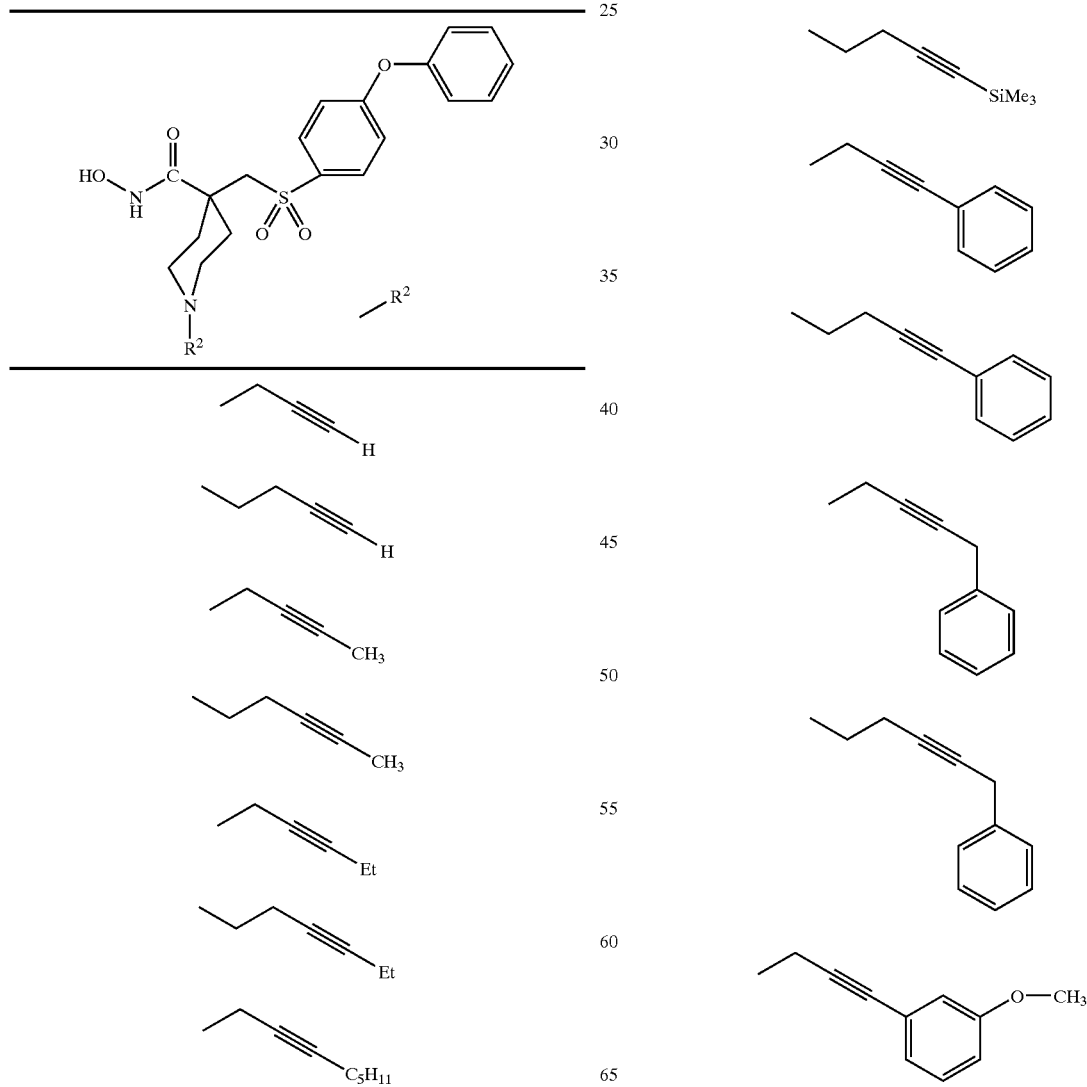

TABLE 11-continued
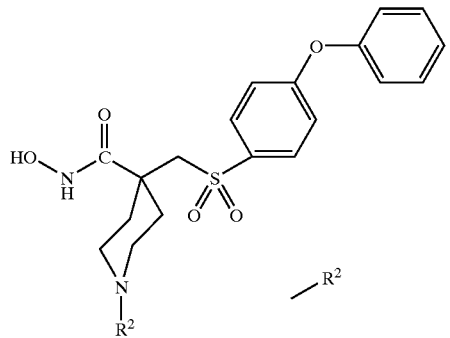
| | R² |
|---|---|
| 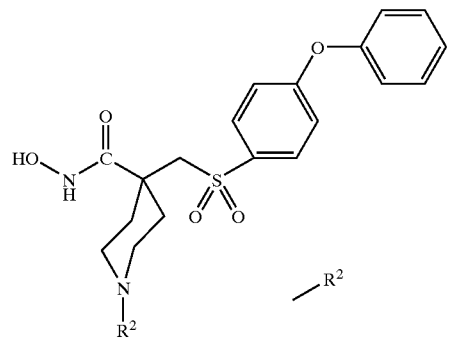 | |
| 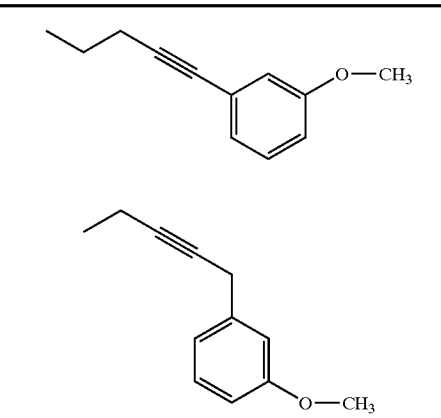 | |
| 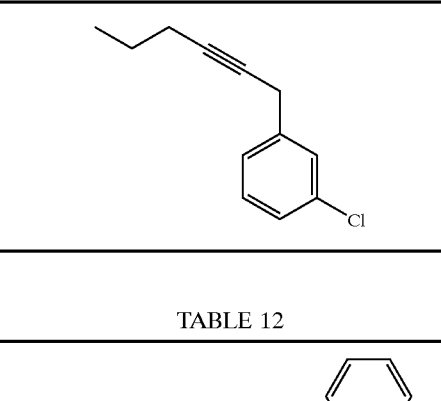 | |
| 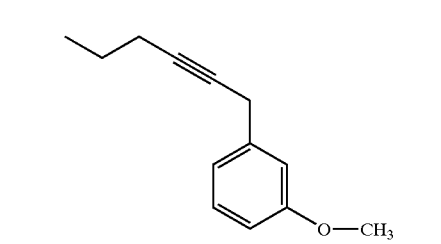 | |
| 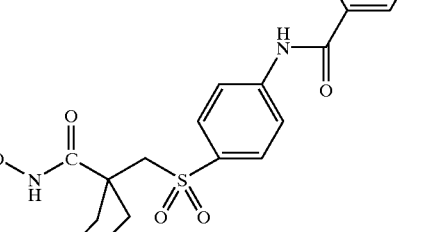 | |
| 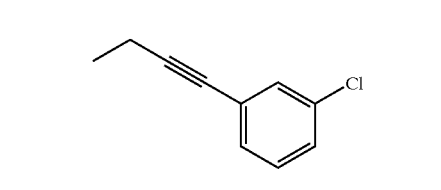 | |
TABLE 11-continued
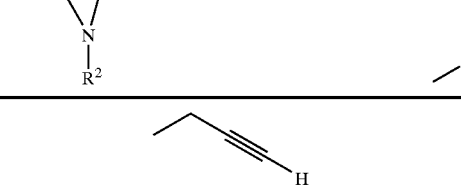
| | R² |
|---|---|
| 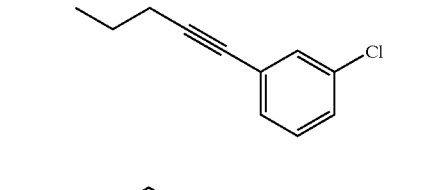 | |
TABLE 12
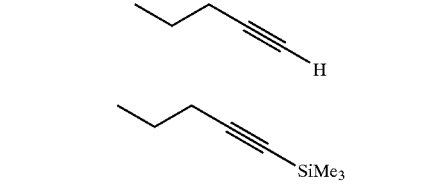
| | R² |
|---|---|
| 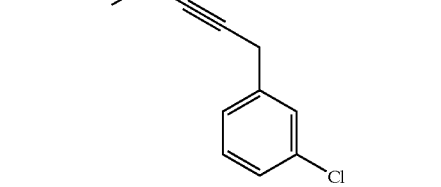 | H |
| 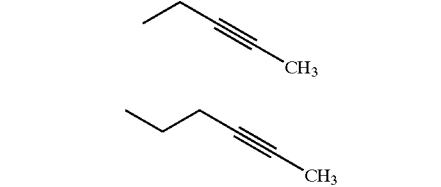 | H |
| | SiMe₃ |
| | CH₃ |
| | CH₃ |

TABLE 12-continued
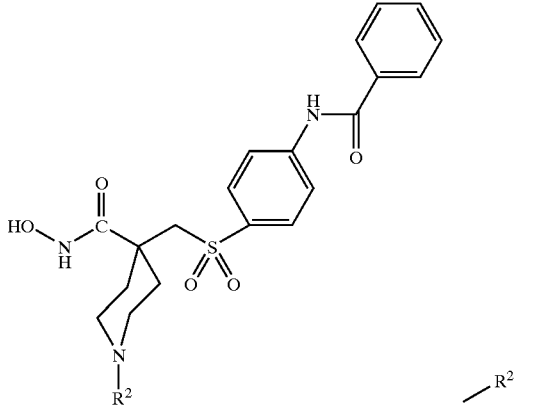
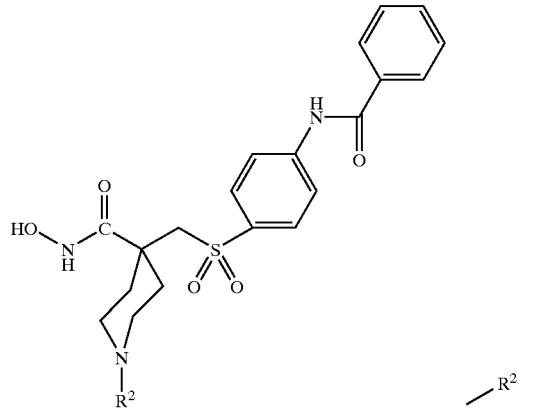

TABLE 12-continued

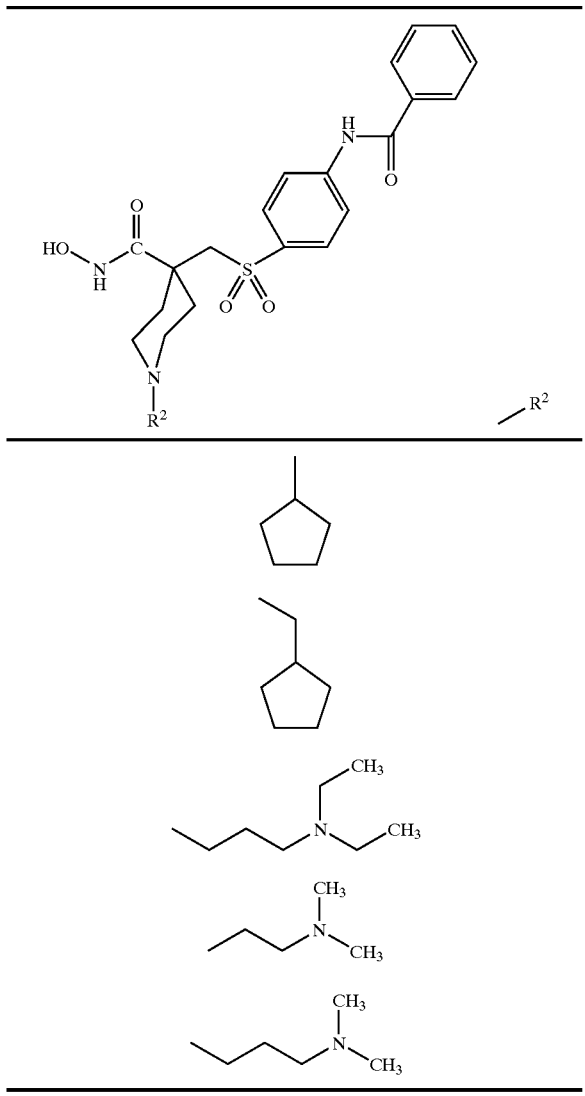

Treatment Process

A process for treating a host mammal having a condition associated with pathological matrix metalloprotease activity is also contemplated. That process comprises administering a compound described hereinbefore in an MMP enzyme-inhibiting effective mount to a mammalian host having such a condition. The use of administration repeated a plurality of times is particularly contemplated.

A contemplated compound is used for treating a host mammal such as a mouse, rat, rabbit, dog, horse, primate such as a monkey, chimpanzee or human that has a condition associated with pathological matrix metalloprotease activity.

Also contemplated is the similar use of a contemplated compound in the treatment of a disease state that can be affected by the activity of metalloproteases such as TNF-α convertase. Exemplary of such disease states are the acute phase responses of shock and sepsis, coagulation responses, hemorrhage and cardiovascular effects, fever and inflammation, anorexia and cachexia.

In treating a disease condition associated with pathological matrix metalloproteinase activity, a contemplated MMP inhibitor compound can be used, where appropriate, in the form of an amine salt derived from an inorganic or organic acid. Exemplary acid salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

Also, a basic nitrogen-containing group can be quaternized with such agents as lower alkyl ($C_1$–$C_6$) halides, such as methyl, ethyl, propyl, and butyl chloride, bromides, and iodides; dialkyl sulfates like dimethyl, diethyl, dibuytl, and diamyl sulfates, long chain ($C_8$–$C_{20}$) halides such as decyl, lauryl, myristyl and dodecyl chlorides, bromides and iodides, aralkyl halides like benzyl and phenethyl bromides, and others to provide enhanced water-solubility. Water or oil-soluble or dispersible products are thereby obtained as desired. The salts are formed by combining the basic compounds with the desired acid. Other compounds useful in this invention that are acids can also form salts. Examples include salts with alkali metals or alkaline earth metals, such as sodium, potassium, calcium or magnesium or with organic bases or basic quaternary ammonium salts.

In some cases, the salts can also be used as an aid in the isolation, purification or resolution of the compounds of this invention.

Total daily dose administered to a host mammal in single or divided doses of an MMP enzyme-inhibiting effective amount can be in amounts, for example, of about 0.001 to about 100 mg/kg body weight daily, preferably 0.001 to about 30 mg/kg body weight daily and more usually about 0.01 to about 10 mg. Dosage unit compositions can contain such amounts or submultiples thereof to make up the daily dose. A suitable dose can be administered, in multiple sub-doses per day. Multiple doses per day can also increase the total daily dose, should such dosing be desired by the person prescribing the drug.

The dosage regimen for treating a disease condition with a compound and/or composition of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed can vary widely and therefore can deviate from the preferred dosage regimen set forth above.

A compound useful in the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co. (Easton, Pa.: 1975) and Liberman, H. A. and Lachman, L., eds., *Pharmaceutical Dosage Forms*, Marcel Decker (New York, N.Y.: 1980).

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and nonionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono- di- or triglycerides, fatty acids and polyethylene glycols that are sold at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian host treated and the particular mode of administration.

Preparation of Useful Compounds

Schemes A and 1A through 2C hereinbelow illustrate chemical processes and transformations that can be useful for the preparation of compounds useful in this invention; i.e., compounds of Formulas I–IV, with particular emphasis on compounds of Formulas II and III, and similar compounds.

Scheme A

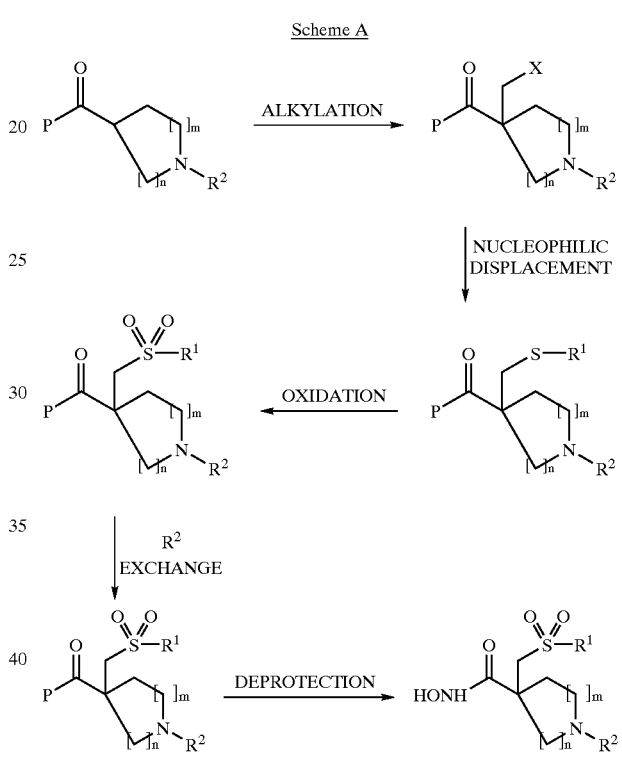

The generic Scheme A shows the conversion of an amino acid, which can be protected or unprotected, into a compound of this invention. The carboxylic acid can be protected with a group P such as an alkyl ester such as methyl, ethyl, tert-butyl, tetrahydropyranyl and the like or an arylalkyl ester such as benzyl or it can remain as a carboxylic acid; i.e., where P is —OH.

A protected amino acid such as an ethyl ester is preferred. The groups $R^2$ and $R^1$ are as defined before including hydrogen, tert-butoxycarbonyl (BOC or tBOC), benzyloxycarbonyl (Z) and iso-butyloxycarbonyl. The amine can be considered as being a protected intermediate as well as being a contemplated compound when $R^2$ is other than hydrogen. The parameters m and n are also as defined before. The leaving group, X, can be a halogen such as chlorine, bromine or iodine or an active ester such as a sulfonate ester, e.g., toluenesulfonate (tosylate), triflate, mesylate and the like.

The cyclic amino acids used to prepare the compounds of this invention can be prepared in ways known to those skilled in the art. Reduction of heteroaryl or unsaturated or partially unsaturated heterocycles can be carried out. For example, the six membered ring compounds can be synthesized by reduction of the corresponding 2-, 3- or 4-pyridine carboxylic acids, 2-, or 3-pyrazole carboxylic acids or derivatives thereof. The reduction can by hydrogenation in the presence of a catalyst or hydride reduction using a hydride transfer agent such as lithium aluminum hydride.

Exemplary starting amino acids or their derivatives, include ethyl isonipecotate, ethyl nipecotate, pipecolinic acid, proline or its isomers, pyroglutamate or its isomers. The R, S and RS isomers of the amino acids can be used. Some starting material can be obtained from commercial sources. A preferred starting material is ethyl isonipecotate that is used illustratively hereinafter.

Alkylation of the aminoacid at the carbon alpha to the carbonyl group to form contemplated compound precursors can be carried out by first forming an anion using a base. Bases are discussed below. The preferred bases are strong bases that are either hindered and/or non-nucleophilic such as lithium amides, metal hydrides or lithium alkyls. A preferred base is lithium diisopropylamide (LDA) in a dipolar aprotic solvent or THF.

Following or during formation of the anion, an alkylating agent (an electrophile) is added which undergoes a nucleophilic substitution reaction. Non-limiting examples of such alkylating agents are 1,1-, 1,2-dihaloalkanes or haloalkanes also substituted by an activated ester group. Activated ester groups are well known in the art and can include, for example, an ester of a 1,2-halo-alcohol such as a bromo-, iodo- or chloro-ethane para-toluene sulfonate, triflate or mesylate. Preferred alkylating agents are diiodomethane or 1-bromo-2-chloroethane.

Room temperature or less or moderate warming (−10° C. to 60° C.) are the preferred temperatures for carrying out the alkylation reaction. If desired, the reaction temperature might be about −68° C. to the reflux point of the reaction solvent or solvents. The preferred solvent for an alkylation reaction is tetrahydrofuran (THF).

Acids are used in many reactions during various synthesis. The Schemes as well as this discussion preparative methods illustrate acid use for the removal of the THP protecting group to produce a hydroxamic acid, removal of a tert-butoxy carbonyl group, hydroxylamine/ester exchange and the like. These methods, as is well known in the art, can use acid or acid catalysts. The acid can be mono-, di- or tri-protic organic or inorganic acids. Examples of acids include hydrochloric acid, phosphoric acid, sulfuric acid, acetic acid, formic acid, citric acid, succinic acid, hydrobromic acid, hydrofluoric acid, carbonic acid, phosphorous acid, p-toluene sulfonic acid, trifluoromethane sulfonic acid, trifluoroacetic acid, difluoroacetic acid, benzoic acid, methane sulfonic acid, benzene sulfonic acid, 2,6-dimethylbenzene sulfonic acid, trichloroacetic acid, nitrobenzoic acid, dinitrobenzoic acid, trinitrobenzoic acid, and the like. They can also be Lewis acids such as aluminum chloride, borontrifluoride, antimony pentafluoride and the like.

The nitrogen substituent $R^2$ on the amino acid portion of the contemplated compounds can be varied. In addition, that variation can be accomplished at different stages in the synthetic sequence based on the needs and objectives of the skilled person preparing the compounds of this invention.

The N-side chain variations can include replacing the hydrogen substituent with an alkyl, arylalkyl, alkene or alkyne group. That alkylation can be accomplished by methods well known in the art such as alkylation of the amine with an electrophile such as halo- or sulfate ester (activated ester) derivative of the desired side chain, and is generally carried out in the presence of a base such as those discussed above, using a pure or mixed solvent as discussed above. A preferred base is postassium carbonate and a preferred solvent is DMF.

The resulting alkenes and alkynes can be reduced, if desired, by hydrogenation with a metal catalyst and hydrogen, to an alkyl or arylalkyl compound. The alkyne or arylalkyne compound can be similarly reduced to a alkene or alkane under catalytic hydrogenation conditions as discussed above or with an deactivated metal catalyst. Catalysts can include, for example, Pd, Pd on Carbon, Pt, $PtO_2$ and the like. Less robust catalysts include such thing as Pd on $BaCO_3$ or Pd with quinoline or/and sulfur.

An alternative method for alkylation of the amine nitrogen is reductive alkylation. This process, well known in the art, allows treatment of the secondary amine with an aldehyde or ketone in the presence of a reducing agent such as borane, borane:THF, borane:pyridine, lithium aluminum hydride. Alternatively, reductive alkylation can be carried out hydrogenation conditions in the presence of a metal catalyst. Catalysts, hydrogen pressures and temperatures are discussed above and are well known in the art. A preferred reductive alkylation catalyst is borane:pyridine complex.

A contemplated compound includes those wherein $R^2$ as listed above provides amino acid carbamates. Non-limiting examples of these carbamates are the carbobenzoxycarbonyl (Z, CBZ, benzyloxycarbonyl), isobytoxycarbonyl and tert-butoxycarbonyl (BOC, t-BOC) compounds. The materials can be made, as discussed above, at various stages in the synthesis based on the needs and decisions made by a person skilled in the art using methods well known in the art. Useful synthetic techniques and reagents include those used in protein, peptide and amino acid synthesis, coupling and transformation chemistry. The use of the tert-butoxycarbonyl (BOC) and benzyloxycarbonyl (Z) as well as their synthesis and removal are examples of such protection or synthesis schemes.

Transformations of amino acids, amino esters, amino acid hydroxamates, amino acid hydroxamate derivatives and amino acid amides to contemplated compounds is shown in the schemes. Exemplary transformations include, for example, active ester or mixed anhydride couplings wherein preferred bases, if required, are tertiary amines such as N-methylmorpholine. Reagents for protection of the amine group of the protected amino acids include carbobenzoxy chloride, iso-butylchloroformate, tert-butoxycarbonyl chloride, di-tert-butyl dicarbonate and the like that are reacted with the amine in non-protic or dipolar aprotic solvents such as DMF or THF or mixtures of solvents. A preferred reagent is di-tert-butyl dicarbonate and a preferred solvent is THF.

Removal of protecting groups such as carbamates, silyl groups and benzyl, p-methoxybenzyl, or other substituted benzyl groups or diphenylmethyl (benzhydryl) or triphenylmethyl (trityl) can be carried out at different stages in the synthesis of the compounds of this invention as required by methods selected by one skilled in the art. These methods are well known in the art including the amino acid, amino acid coupling, peptide synthesis, peptide mimetic synthesis art.

Exemplary removal methods include catalytic hydrogenation, base hydrolysis, carbonyl addition reactions, acid hydrolysis and the like. Both the preparation and removal of protecting groups, for example, carbamates, benzyl groups and/or substitued arylalkyl groups is discussed in Green, T. et al., *Protecting Groups in Organic Chemistry*, second Ed., John Wiley & Sons, Inc., New York (1991). A preferred method of removal of a BOC group is use of HCl gas in methylene chloride which, following normal work-up, provides directly an HCl salt of an useful amino acid precursor.

In the case where P is hydrogen; i.e., where the intermediate is a carboxylic acid, standard coupling reactions can be used to form the compounds of this invention including protected intermediates. For example, the acid can be converted into an acid chloride, mixed anhydride or activated ester and reacted with an alcohol, hydroxylamine or a protected hydroxylamine in the presence of base to form the nitrogen acylated compound. This is the same product as discussed above. Bases are discussed above and include N-methyl-morpholine, triethyl amine and the like. Coupling reactions of this nature are well known in the art and especially the art related to peptide and amino acid chemistry. Removal of the P group can be accomplished, if desired, using standard hydrolysis conditions such as base hydrolysis or exchange or acid exchange or hydrolysis.

Schemes 1A through 2C, hereinafter, also illustrate conversion of a carboxylic acid protected as an ester or amide into a hydroxamic acid derivative such as a O-arylalkylether or O-cycloalkoxyalkylether group such as the THP group. Methods of reacting an acid or acid derivative with hydroxylamine or a hydroxylamine derivative are discussed above.

For example, hydroxylamine can be used in an exchange reaction by treatment of a precursor compound, where P is an ester or amide, with one or more equivalents of hydroxylamine hydrochloride or hydroxylamine at room temperature or above. This reaction can provide a hydroxamic acid directly. The solvent or solvents are usually protic or protic solvent mixtures such as those listed above. This exchange process can be further catalyzed by the addition of additional acid.

Alternatively, a base such as a salt of an alcohol used as a solvent, for example, sodium methoxide in methanol, can be used to form hydroxylamine from hydroxylamine hydrochloride in situ that can exchange with an ester or amide. As mentioned above, exchange can be carried out with a protected hydroxyl amine such as tetrahydropyranylhydroxyamine (THPONH$_2$), benzylhydroxylamine (BnONH$_2$) and the like in which case the compounds formed are tetrahydropyranyl (THP) or benzyl (Bn) hydroxamic acid derivatives.

Removal of the protecting groups when desired, for example, following further transformations in another part of the molecule or following storage, can be accomplished by standard methods well known in the art such as acid hydrolysis of the THP group as discussed above or reductive removal of the benzyl group with hydrogen and a metal catalyst such as palladium, platinum, palladium on carbon or nickel. Preferred is reaction of the hydroxybenzotriazole (HOBT) ester of an acid with hydroxylamine in water or a water/organic solvent mixture.

Sulfone compounds such as those where $R^1$ is nitrobenzene can be prepared as compounds of this invention by synthesis of a thiol, displacement of an electrophile (X) by the nucleophilic thiol or thiolate and oxidation of the product thiol ether to the sulfone. For example, displacement of the electrophilic group X with a nitro-benzene-thiol can yield a compound where $R^1$ is nitrobenzene that can be reduced to provide a useful amino compound wherein R is an aniline. It should be noted that nitrobenzenethiol is an example and not to be considered as limiting or required. Oxidation of the thioether product can be carried out as discussed below when desired.

The reduction of nitro groups to amines is well known in the art with a preferred method being hydrogenation. There is usually a metal catalyst such as Rh, Pd, Pt, Ni or the like with or without an additional support such as carbon, barium carbonate and the like. Solvents can be protic or non-protic pure solvents or mixed solvents as required. The reductions can be carried out at atmospheric pressure to a pressure of multiple atmospheres with atmospheric pressure to about 40 pounds per square inch (psi) preferred.

The resulting amino group can be alkylated if desired. It can also be acylated with, for example, an aroyl chloride, heteroaryl chloride or other amine carbonyl-forming agent to form an $R^1$ amide of this innvention. The amino sulfone or thioether can also be reacted with a carbonic acid ester chloride, a sulfonyl chloride, a carbamoyl chloride or an isocyanate to produce the corresponding carbamate, sulfonamides, or ureas of this invention.

Acylation of amines of this type are well known in the art and the reagents are also well known. Usually these reactions are carried out in aprotic solvents under an inert or/and dry atmosphere at about 45° C. to about −10° C. An equivalent of a non-competitive base is usually used with sulfonyl chloride, acid chloride or carbonyl chloride reagents. Following or before this acylation step, synthesis of the hydroxamic acid products of this invention can proceed as discussed.

Other thiol reagents can also be used in the preparation of compounds of this invention. Examples are fluoroaryl, fluoroheteroaryl, azidoaryl or azidoheteroaryl or heteroaryl thiol reagents. These thiols can be used a nucleophiles to as discused above. Oxidation to the corresponding sulfone can then be carried out after the nucleophjilic reaction is completed.

The fluoro-substituted sulfone resulting from such an oxidation can be treated with a nucleophile such as ammonia, a primary amine, a quaternary ammonium or metal azide salt, under pressure if desired, to provide an azido, amino or substituted amino group that can then be reacted an activated benzoic or substituted benzoic acid derivative to form a benzamide. Azides can be reduced to an amino group using, for example, hydrogen with a metal catalyst or metal chelate catalyst or by an activated hydride transfer reagent. The amines can be acylated as discussed above. Preferred methods of preparing aminethiol intermediates of this invention include protection of an aromatic or heteroaromatic thiol with trityl chloride to form the trityl thiol derivative, treatment of the amine with as reagent such as an aromatic or heteraromatic acid chloride to form the amide, removal to the trityl group, with acid to form the thiol. Preferred acylating agents include benzoyl chloride and preferred trityl remoing reagents include triflouroacetic acid and trisiopropylsilane.

The fluorine on the fluorosulfone precursors can also be displaced with other aryl or heteroaryl nucleophiles for form compounds of this invention. Examples of such nucleophiles include salts of phenols, thiophenols, —OH group-containing aromatic heterocyclic compounds or —SH containing heteroaryl compounds. Tautomers of such groups azo, hydrazo, —OH or —SH are specifically included as useful isomers.

A preferred method of preparing intermediates in the synthesis of the substituted sulfones is by oxidation of an appropriate acetophenone, prepared from a flouroacetophenone, with for example, peroxymonosulfate, to form the corresponding phenol-ether. This is converted into its dimethylthiocarbamoyl derivative using dimethylthiocarbamoyl chloride, rearranging the dimethylthiocarbamoyl derivative with heat to provide the thiol required for preparation of the thioether intermediate discussed above and shown in the schemes.

The compounds of this invention including protected compounds or intermediates can be oxidized to the sulfones as shown in the schemes and discussed above. The selection of the stage of the alternative synthesis to implement this conversion of sulfides into the sulfones or sulfoxides can be carried out by one skilled in the art. Reagents for this oxidation process, in a non-limiting example, include peroxymonosulfate (OXONE®), hydrogen peroxide, metachloroperbenzoic acid, perbenzoic acid, peracetic acid, perlactic acid, tert-butyl peroxide, tert-butyl hydroperoxide, tert-butyl hypochlorite, sodium hypochlorite, hypochlorous acid, sodium meta-peroiodate, periodic acid, ozone and the like. Protic, non-protic, dipolar aprotic solvents, either pure or mixed, can be chosen, for example, methanol/water.

The oxidation can be carried out at temperature of about −68° C. to about 50° degrees centigrade and normally selected from a range −10° C. to about 40° C. Preparation of the sulfones can also be carried out in two steps by the oxidation of a sulfide to a sulfoxide followed by oxidation of the sulfoxide to the sulfone. This can occur in one pot or by isolation of the sulfoxide. This latter oxidation can be carried out in a manner similar to the oxidation directly to the sulfone except that about one equivalent of oxidizing agent can be used, preferably at a lower temperature such as about zero degrees Celsius. Preferred oxidizing agents include peroxymonosulfate and meta-chloroperbenzoic acid.

The before-discussed reactions can be carried out under a dry inert atmosphere such a nitrogen or argon if desired.

Selected reactions known to those skilled in the art can be carried out under a dry atmosphere such as dry air whereas other synthetic steps, for example, aqueous acid or base ester or amide hydrolysis, can be carried out under laboratory air. In addition, some processes of these syntheses can be carried out in a pressure apparatus at pressures above, equal to or below atmospheric pressure. The use of such an apparatus aids in the control of gaseous reagents such as hydrogen, ammonia, trimethylamine, methylamine, oxygen and the like, and can also help prevent the leakage of air or humidity into a reaction in progress. This discussion is not intended to be exhaustive as it is readily noted that additional or alternative methods, conditions, reactions or systems can be identified and used by a chemist of ordinary skill.

Schemes 1 and 2 that are provided hereinafter illustrate specific reactions useful in preparing a contemplated compound. Further specifics for those reactions can be found in the Examples that follow.

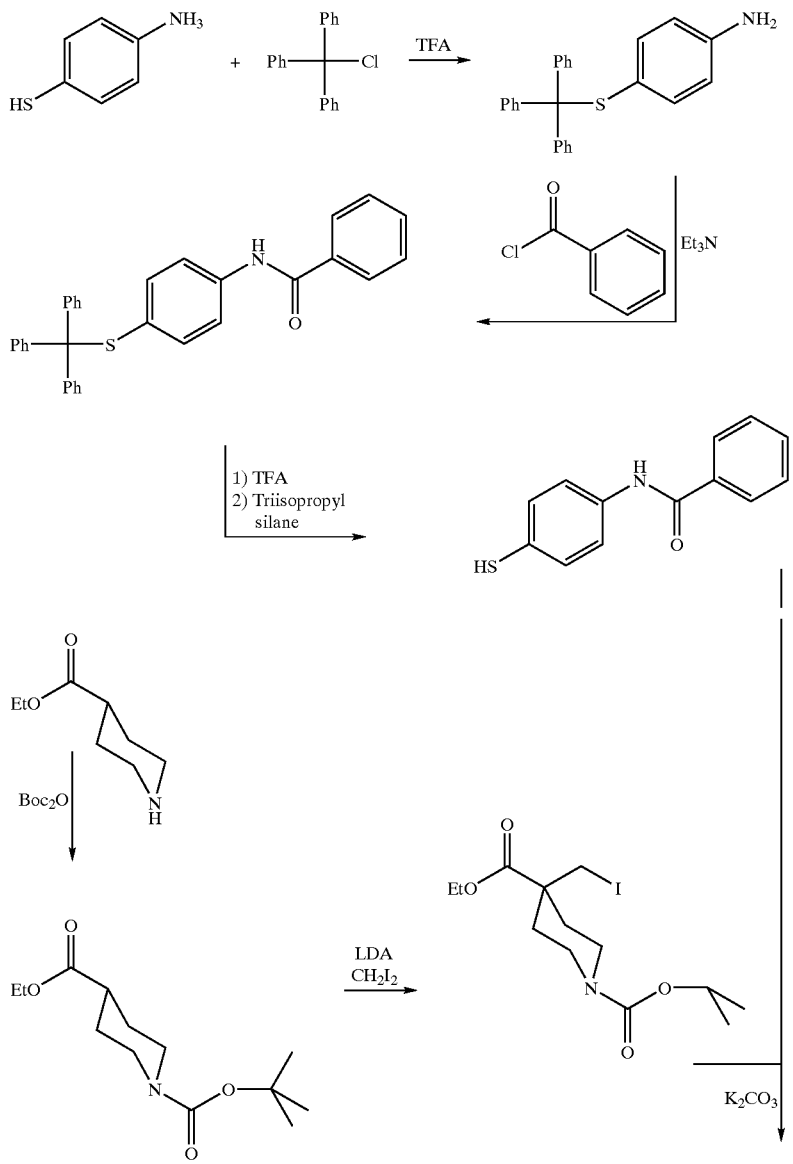

Scheme 1A: Example 1

Scheme 1B: Example 1
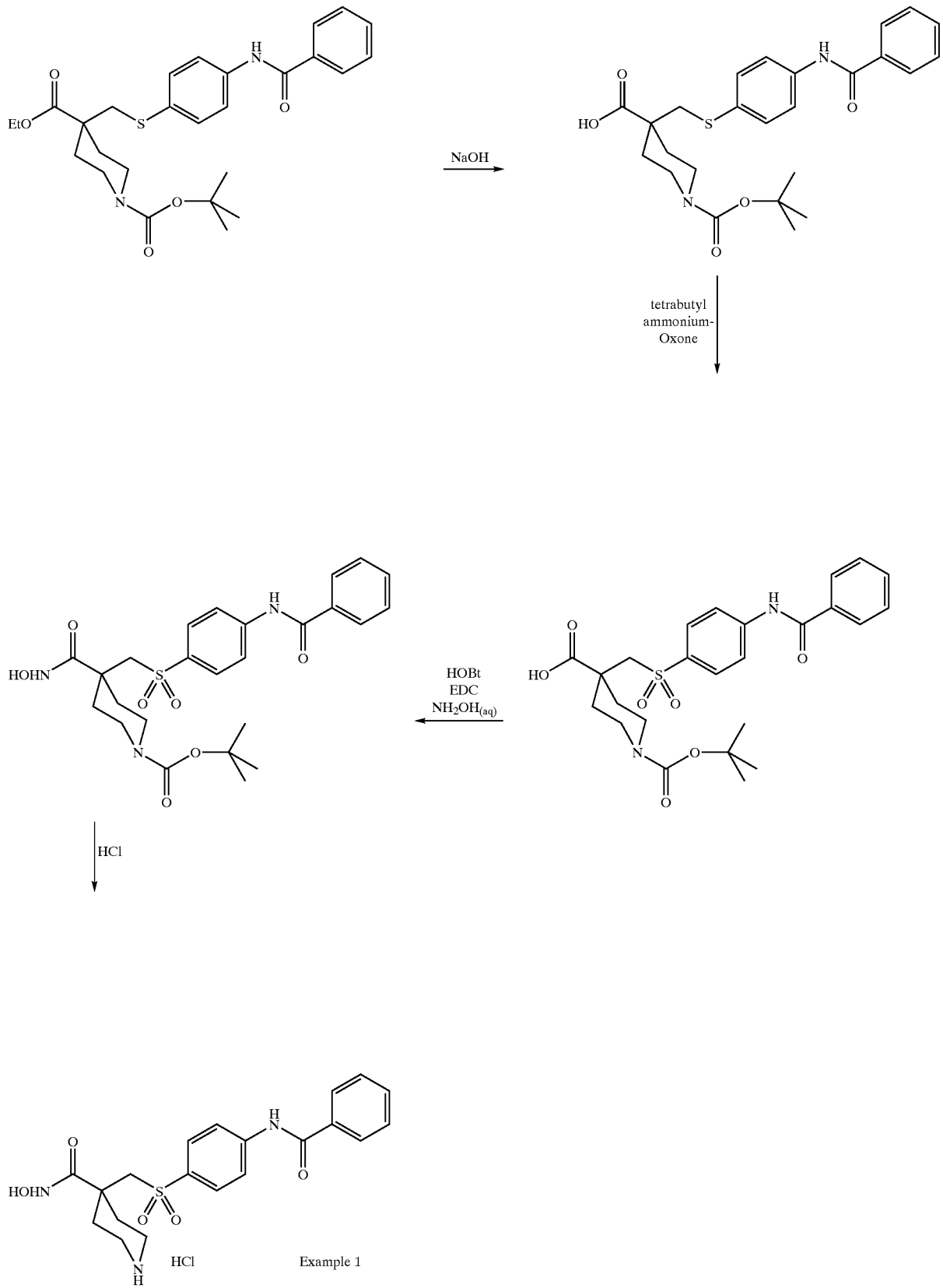

Scheme 2A: Examples 2, 3, 4–7
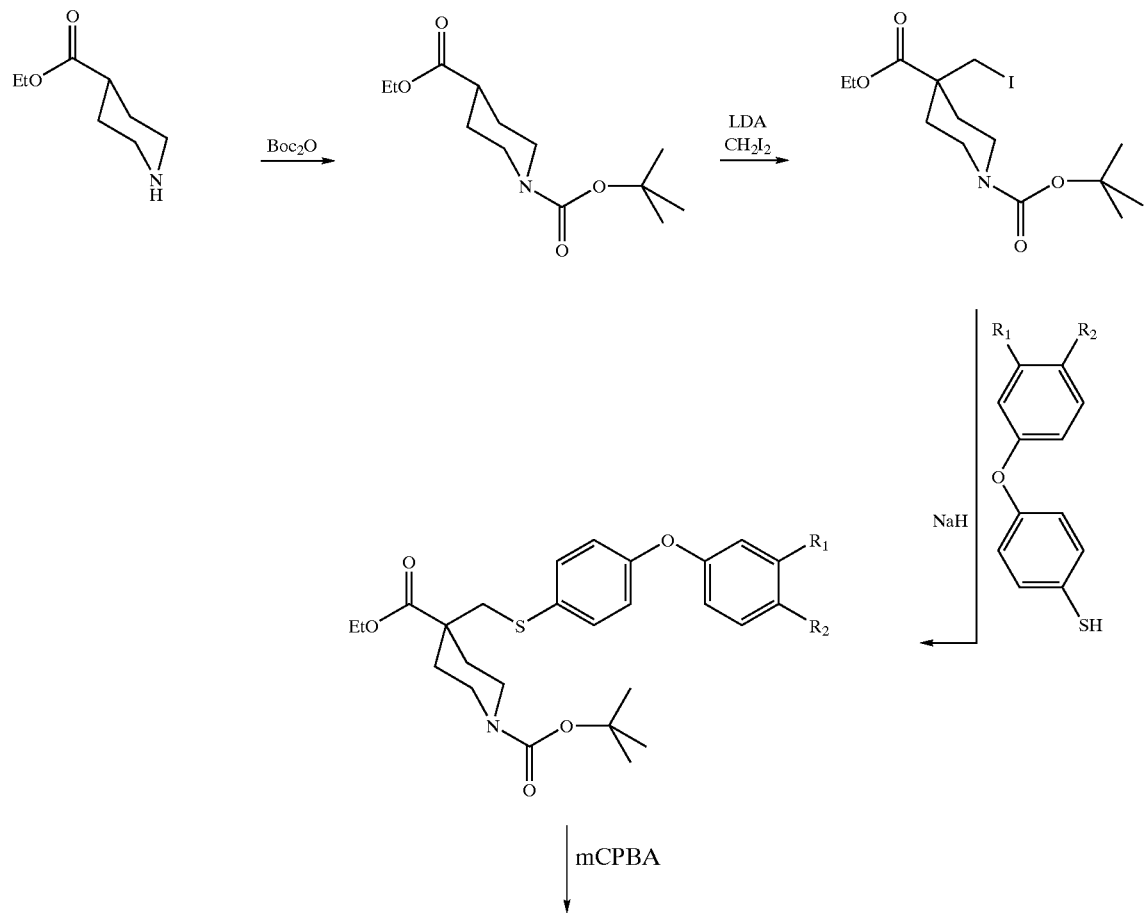
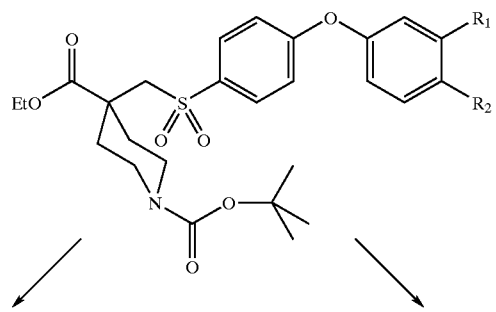
Scheme 2C                    Scheme 2B Scheme 2B

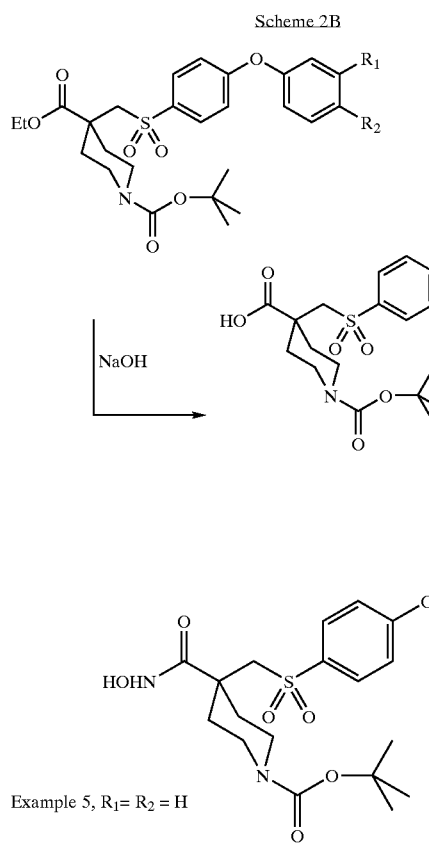

Example 5, R₁ = R₂ = H

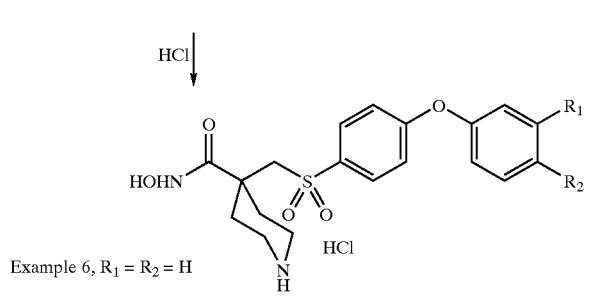

Example 6, R₁ = R₂ = H

Scheme 2C

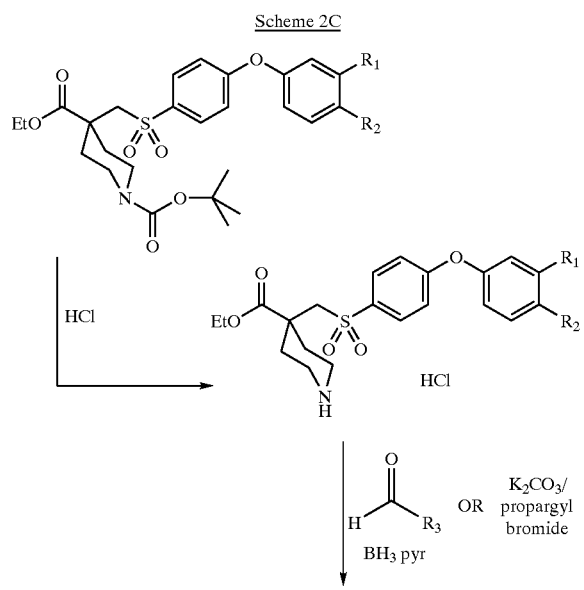

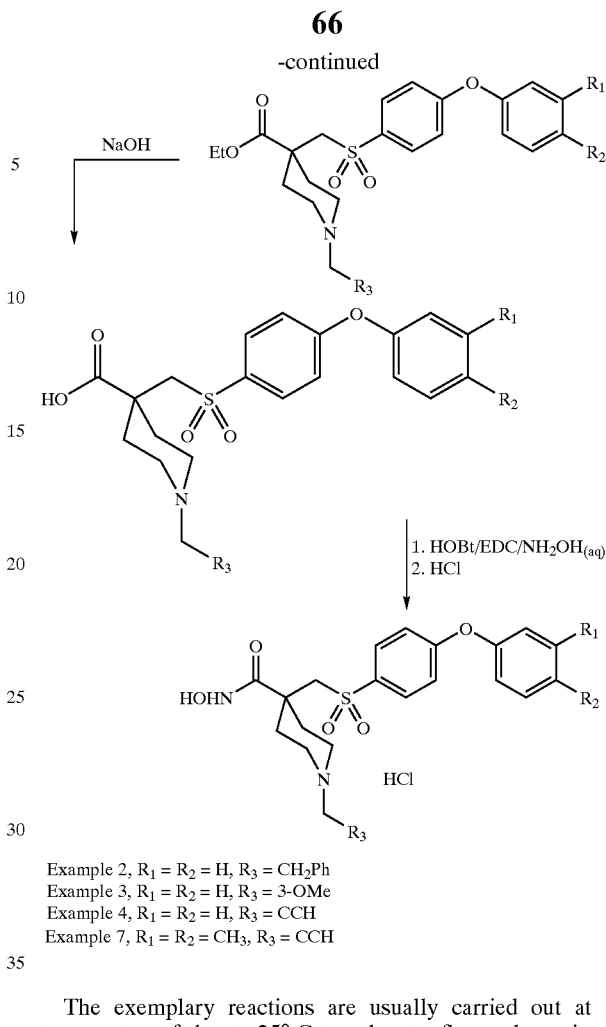

Example 2, R₁ = R₂ = H, R₃ = CH₂Ph
Example 3, R₁ = R₂ = H, R₃ = 3-OMe
Example 4, R₁ = R₂ = H, R₃ = CCH
Example 7, R₁ = R₂ = CH₃, R₃ = CCH The exemplary reactions are usually carried out at a temperature of about −25° C. to solvent reflux under an inert atmosphere such as nitrogen or argon. The solvent or solvent mixture can vary widely depending upon reagents and other conditions and can include polar or dipolar aprotic solvents as listed or mixtures of these solvents.

In some cases, amines such as triethyl amine, pyridine or other non-reactive bases can serve as reagents and/or solvents and/or co-solvents. In some instances, in these reactions and other reactions in these Schemes, protecting groups can be used to maintain or retain groups in other parts of a molecule(s) at locations that is(are) not desired reactive centers. Examples of such groups that the skilled person might want to maintain or retain include, amines, other hydroxyls, thiols, acids and the like. Such protecting groups can include acyl groups, arylalkyl groups, carbamoyl groups, ethers, alkoxyalkyl ethers, cycloalkyloxy ethers, arylalkyl groups, silyl groups including trisubstituted silyl groups, ester groups and the like. Examples of such protecting groups include acetyl, trifluoroacetyl, tetrahydropyran (THP), benzyl, tert-butoxy carbonyl (BOC or TBOC), benzyloxycarbonyl (Z or CBZ), tert-butyldimethylsilyl (TBDMS) or methoxyethoxymethylene (MEM) groups. The preparation of such protected compounds as well as their removal is well known in the art.

Many reactions or processes involve bases that can act as reactants, reagents, deprotonating agents, acid scavengers, salt forming reagents, solvents, co-solvents and the like. Bases that can be used include, for example, metal hydroxides such as sodium, potassium, lithium, cesium or magnesium hydroxide, oxides such as those of sodium, potassium, lithium, calcium or magnesium, metal carbonates such as those of sodium, potassium, lithium, cesium, calcium or magnesium, metal bicarbonates such as sodium bicarbonate or potassium bicarbonate, primary (I°), secondary (II°) or tertiary (III°) organic amines such as alkyl amines, arylalkyl amines, alkylarylalkyl amines, heterocyclic amines or heteroaryl amines, ammonium hydroxides or quaternary ammonium hydroxides. As non-limiting examples, such amines can include triethylamine, trimethylamine, diisopropylamine, methyldiisopropylamine, diazabicyclononane, tribenzylamine, dimethylbenzylamine, morpholine, N-methylmorpholine, N,N'-dimethylpiperazine, N-ethylpiperidine, 1,1,5,5-tetramethylpiperidine, dimethylaminopyridine, pyridine, quinoline, tetramethylethylenediamine, diazabicyclononane and the like. Non-limiting examples of ammonium hydroxides, usually made from amines and water, can include ammonium hydroxide, triethyl ammonium hydroxide, trimethyl ammonium hydroxide, methyldiisopropyl ammonium hydroxide, tribenzyl ammonium hydroxide, dimethylbenzyl ammonium hydroxide, morpholinium hydroxide, N-methylmorpholinium hydroxide, N,N'-dimethylpiperazinium hydroxide, N-ethylpiperidinium hydroxide, and the like. As non-limiting examples, quaternary ammonium hydroxides can include tetraethyl ammonium hydroxide, tetramethyl ammonium hydroxide, dimethyldiisopropyl ammonium hydroxide, benzymethyldiisopropyl ammonium hydroxide, methyldiazabicyclononyl ammonium hydroxide, methyltribenzyl ammonium hydroxide, N,N-dimethylmorpholinium hydroxide, N,N,N',N'-tetramethylpiperazenium hydroxide, and N-ethyl-N'-hexylpiperidinium hydroxide and the like.

Metal hydrides, amides or alcoholates such as calcium hydride, sodium hydride, potassium hydride, lithium hydride, aluminum hydride, diisobutylaluminum hydride (DIBAL) sodium methoxide, potassium tert-butoxide, calcium ethoxide, magnesium ethoxide, sodium amide, potassium diisopropyl amide and the like can also be suitable reagents. Organometallic deprotonating agents such as alkyl or aryl lithium reagents such as methyl lithium, phenyl lithium, tert-butyl lithium, lithium acetylide or butyl lithium, Grignard reagents such as methylmagnesium bromide or methymagnesium chloride, organocadmium reagents such as dimethylcadmium and the like can also serve as bases for causing salt formation or catalyzing the reaction. Quaternary ammonium hydroxides or mixed salts are also useful for aiding phase transfer couplings or serving as phase transfer reagents. Pharmaceutically acceptable bases and be reacted with acids to form pharmaceutically acceptable salts of this invention. It should also be noted that optically active bases can be used to make optically active salts which can be used for optical resolutions.

Generally, reaction media can comprise a single solvent, mixed solvents of the same or different classes or serve as a reagent in a single or mixed solvent system. The solvents can be protic, non-protic or dipolar aprotic. Non-limiting examples of protic solvents include water, methanol (MeOH), denatured or pure 95% or absolute ethanol, isopropanol and the like. Typical non-protic solvents include acetone, tetrahydrofurane (THF), dioxane, diethylether, tert-butylmethyl ether (TBME), aromatics such as xylene, toluene, or benzene, ethyl acetate, methyl acetate, butyl acetate, trichloroethane, methylene chloride, ethylenedichloride (EDC), hexane, heptane, isooctane, cyclohexane and the like. Dipolar aprotic solvents include compounds such as dimethylformamide (DMF), dimethylacetamide (DMAc), acetonitrile, DMSO, hexamethylphosphorus triamide (HMPA), nitromethane, tetramethylurea, N-methylpyrrolidone and the like. Non-limiting examples of reagents that can be used as solvents or as part of a mixed solvent system include organic or inorganic mono- or multiprotic acids or bases such as hydrochloric acid, phosphoric acid, sulfuric acid, acetic acid, formic acid, citric acid, succinic acid, triethylamine, morpholine, N-methylmorpholine, piperidine, pyrazine, piperazine, pyridine, potassium hydroxide, sodium hydroxide, alcohols or amines for making esters or amides or thiols for making the products of this invention and the like.

Salts of the compounds or intermediates of this invention are prepared in the normal manner wherein acidic compounds are reacted with bases such as those discussed above to produce metal or nitrogen containing cation salts. Basic compounds such as amines can be treated with an acid to for form the amine salt. A preferred amine salt is the hydrochloride salt formed by reaction of the free base with HCl or hydrochloric acid.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes well known in the art, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers.

Still another available method involves synthesis of covalent diastereomeric molecules, e.g., esters, amides, acetals, ketals, and the like, by reacting compounds of Formula I with an optically active acid in an activated form, a optically active diol or an optically active isocyanate. The synthesized diastereoisomers can be separated by conventional means such as chromatography, distillation, crystallization or sublimation, and then hydrolyzed to deliver the enantiomericaly pure compound. In some cases, hydrolysis to the parent optically active drug is not necessary prior to dosing the patient since the compound can behave as a prodrug. The optically active compounds of Formula I can likewise be obtained by utilizing optically active starting materials.

In additon to the optical isomers or potential optical isomers discussed above, other types of isomers are specifically intended to be included in this discussion and in this invention. Examples include cis isomers, trans isomers, E isomers, Z isomers, syn-isomers, anti-isomers, tautomers and the like. Aryl, heterocyclo or heteroaryl tautomers, heteroatom isomers and ortho, meta or para substitution isomers are also included as isomers. Solvates or solvent addition compounds such as hydrates or alcoholates are also specifically included both as chemicals of theis invention and in, for example, formulations or pharmaceutical compositions for delivery.

Contemplated equivalents of the general formulas set forth above for the MMP inhibitor compounds and derivatives as well as the intermediates are compounds otherwise corresponding thereto and having the same general properties such as tautomers thereof and compounds wherein one or more of the various R groups are simple variations of the substituents as defined therein, e.g., wherein R is a higher alkyl group than that indicated. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure. For example, two hydroxyl groups, two amino groups, two thiol groups or a mixture of two hydrogen-heteroatom groups on the same carbon are known not to be stable without protection or as a derivative.

The chemical reactions described above are generally disclosed in terms of their broadest application to the preparation of the compounds of this invention. Occasionally, the reactions can not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

The compounds of this invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibuytl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained as desired. The salts are formed by combining the basic compounds with the desired acid.

Other compounds of this invention that are acids can also form salts. Examples include salts with alkali metals or alkaline earth metals, such as sodium, potassium, calcium or magnesium or with organic bases or basic quaternary ammonium salt. In some cases, the salts can also be used as an aid in the isolation, purification or resolution of the compounds.

Best Mode for Carrying Out the Invention

Without further elaboration, it is believed that one skilled in the art can, using the preceding description, utilize the present invention to its fullest extent. The following preferred specific embodiments are, therefore, to be construed as merely illustrative, and not limiting of the remainder of the disclosure in any way whatsoever.

EXAMPLE 1

N-Hydroxy-4-[[[4-(benzoylamino)phenyl]-sulfonyl]methyl]-4-piperidinecarboxamide, Monohydrochloride

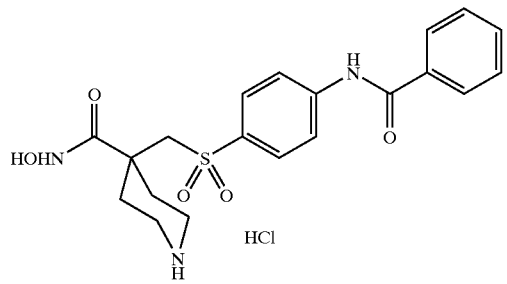

Part A: To a solution of trityl chloride (20.24 g, 72.62 mmol) and trifluoroacetic acid (8 mL) in dichloromethane (100 mL) was added 4-aminothiophenol (10.00 g, 79.88 mmol) in dichloromethane (150 mL) dropwise. After stirring at ambient temperature for 30 minutes, the solution was diluted with H$_2$O and neutralized with 2.5 N NaOH to pH=10. The organic layer was separated and washed with H$_2$O and dried over Na$_2$SO$_4$. The solution was concentrated in vacuo and trituration with ethyl ether afforded the trityl-protected aniline compound as a tan solid (trityl 4-aminobenzenethioether; 22.85 g, 86%). HPLC purity: 98%.

Part B: To a solution of the aniline compound of Part A (10.00 g, 27.21 mmol) and triethylamine (5.69 mL, 40.82 mmol) in dichloromethane (40 mL) was added benzoyl chloride (3.47 g, 29.93 mmol). After 1 hour of stirring at ambient temperature, the mixture was diluted with dichloromethane and washed with H$_2$O. The organic was concentrated and after washing with ethyl ether provided the acylated aniline compound as an off-white solid (trityl 4-[benzoylamino]benzenethioether; 13.00 g, quantitative yield). HPLC purity: 99%.

Part C: The trityl protecting group was removed from the thiol group of the acylated aniline of Part B as follows. To a solution of the acylated aniline of part B (6.00 g, 12.72 mmol) in dichloromethane (25 mL) was added triisopropyl silane (13.03 mL, 63.61 mmoL) followed by trifluoroacetic acid (25 mL). After 30 minutes at ambient temperature the mixture was concentrated in vacuo and trituration with hexane provided the acylated aminothiophenol as a white solid (4-[benzoylamino]benzenethiol; 3.02 g, quantitative yield).

Part D: To a solution of ethyl isonipecotate (ethyl 4-piperidinecarboxylate; 15.7 g, 0.1 mol) in tetrahydrofuran (100 mL) was added a solution of di-tert-butyl dicarbonate (di-t-BOC; 21.8 g, 0.1 mol) in THF (5 mL) dropwise over 20 minutes. The solution stirred overnight at ambient temperature and concentrated in vacuo to yield a light oil. The oil was filtered through silica gel (7:3 ethyl acetate/hexane) and concentrated in vacuo to give the BOC-piperidine compound (ethyl-4-[BOC-piperidine]carboxylate; 26.2 g, quantitative yield) as a clear, colorless oil.

Part E: To a solution of the BOC-piperidine compound of Part D (17.56 g, 0.068 mol) in tetrahydrofuran (100 mL) cooled to −42° C. was added lithium diisopropylamine, 1.8M in THF (37.8 mL, 0.068 mol) dropwise to not exceed −40° C. After 1 hour diiodomethane (5.5 mL, 0.068 mol) was added. The solution was warmed to ambient temperature after the addition and stirred for 5 hours. The solution was diluted with H₂O and extracted with ethyl ether. The organic layer was washed with H₂O, sat. NaCl, and dried over MgSO₄. Concentration provided the iodo compound (ethyl 4[iodomethyl]-4-[BOC-piperidine]carboxylate; 28.8 g, quantitative yield) as a clear brown oil.

Part F: To a solution of the iodo compound of Part E (2.00 g, 5.03 mmol) in DMF (10 mL), was added K₂CO₃ (1.39 g, 10.06 mmol) followed by the thiophenol of Part C (4-[benzoylamino]benzenethiol; 1.27 g, 5.54 mmol). After stirring for 90 hours at ambient temperature, the reaction was partitioned between ethyl acetate and H₂O. The organic layer was washed with H₂O and satd. NaCl and dried over Na₂SO₄. Chromatography (7:3 hexane/ethyl acetate) provided the thiophenol/piperidine compound as a pale yellow oil (ethyl 4-[[[4-(benzoylaminophenyl]thio]methyl]-4-(BOC-piperidine)carboxylate; 1.89 g, 75%). HPLC purity: 98%.

Part G: To a solution of the thiophenol/piperidine compound of Part F (1.89 g, 3.78 mmol) in ethanol (3 mL) and THF (3 mL) was added 50% aqueous NaOH (3 mL) at ambient temperature. After 18 hours the solution was acidified with 1N HCl to pH=2 and extracted twice with ethyl acetate. The organic layers were washed with satd. NaCl and dried over Na₂SO₄. Concentration in vacuo provided the carboxylic acid compound as an orange solid (4-[[[4-(benzoylamino)phenyl]-thio]-methyl]-4-(BOC-piperidine) carboxylic acid; 1.76 g, 99%). HPLC purity: 91%.

Part H: To a solution of the carboxylic acid compound of Part G (1.74 g, 3.69 mmol) in dichloromethane (20 mL) was added tetrabutylammonium-Oxone (13.10 g, 11.07 mmol). The mixture was stirred at ambient temperature for 18 hours. Additional tetrabutylammonium-Oxone (4.37 g, 3.69 mmol) was added to ensure complete conversion to the sulfone. After an additional 18 hours of stirring at ambient temperature the solvent was removed in vacuo and the residue was dissolved into ethyl acetate. The organic solution was washed with H₂O, 5% aqueous KHSO₄, satd. NaCl, and dried over Na₂SO₄. Concentration in vacuo provided the sulfone compound as a tan solid (4-[[[(benzoylamino) phenyl]sulfonyl]methyl]-4-4(BOC-piperidine)carboxylic acid; 1.88 g, quantitative yield). HPLC purity: 93%.

Part I: To a solution of the sulfone compound of Part H (0.900 g, 1.79 mmol) in DMF (5 mL) was added N-hydroxybenzotriazole.H₂O (0.282 g, 2.09 mmol) and 1-(3-dimethylaminopropyl)-3-ethylcarbodiimide hydrochloride (0.401 g, 2.09 mmol). After 3.5 hours of stirring at ambient temperature, 50% aqueous hydroxylamine (1.06 mL, 17.90 mmol) was added. After 2 hours the solvent was removed in vacuo and the residue was dissolved into ethyl acetate, washed with H₂O and satd. NaCl, and dried over Na₂SO₄. Purification via reverse phase HPLC (acetonitrile/H₂O) provided the hydroxamate compound as an off-white solid (N-hydroxy-4-[[[4-(benzoylamino)phenyl]sulfonyl] methyl]-4-(BOC-piperidine)carboxamide; 0.36 g, 39%). HPLC purity: 98%.

Part J: To a solution of the hydroxamate compound of Part I (0.350 g, 0.675 mmol) in methanol (1 mL)/dioxane (9 mL) was added 4N HCl in dioxane (10 mL) at ambient temperature. After 1 hour the solution was concentrated in vacuo to provide the title compound, N-hydroxy-4-[[[4-(benzoylamino)phenyl]-sulfonyl]methyl]-4-piperidinecarboxamide, monohydrochloride, as an off-white solid (0.330 g, quantitative yield). HPLC purity: 98%. HRMS calc'd for C₂₀H₂₄N₃O₅S: 418.1437, found 418.1449.

EXAMPLE 2

N-Hydroxy-4-[[(4-phenoxyphenyl)sulfonyl]-methyl]-1-(2-phenylethyl)-4-piperidinecarboxamide, Monohydrochloride

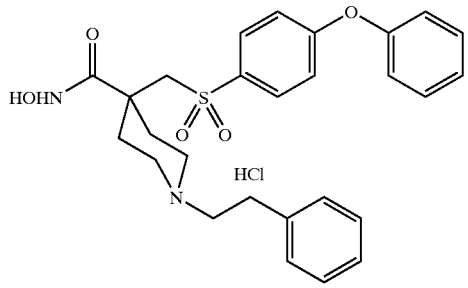

Part A: To a solution of ethyl isonipecotate (ethyl 4-piperidinecarboxylate; 15.7 g, 0.1 mol) in tetrahydrofuran (100 mL) was added a solution of di-tert-butyl dicarbonate (di-t-BOC; 21.8 g, 0.1 mol) in THF (5 mL) dropwise over 20 minutes. The solution stirred overnight at ambient temperature and concentrated in vacuo to yield a light oil. The oil was filtered through silica gel (7:3 ethyl acetate/hexane) and concentrated in vacuo to give the BOC-piperidine compound (ethyl 4-[BOC-piperidine]carboxylate; 26.2 g, quantitative yield) as a clear, colorless oil.

Part B: To a solution of the BOC-piperidine compound of Part A (17.56 g, 0.068 mol) in tetrahydrofuran (100 mL) cooled to −42° C. was added lithium diisopropylamine, 1.8M in THF (37.8 mL, 0.068 mol) dropwise to not exceed −40° C. After 1 hour diiodomethane (5.5 mL, 0.068 mol) was added. The solution was warmed to ambient temperature after the addition was complete and stirred for 5 hours. The solution was diluted with H₂O and extracted with ethyl ether. The organic layer was washed with H₂O, satd. NaCl, and dried over MgSO₄. Concentration provided the iodo compound (ethyl-4-[iodomethyl]-4-[BOC-piperidine] carboxylate; 28.8 g, quantitative yield) as a clear brown oil.

Part C: A suspension of NaH (152 mg of a 60% dispersion in mineral oil, 3.8 mmol) in DMF (3 mL) was cooled to zero degrees C. on an ice/H₂O bath and a solution of 4-(phenoxy) benzenethiol (769 mg, 3.8 mmol) in DMF (5 mL) was added dropwise and stirred until a homogenous solution resulted. To this solution was added the iodo compound of Part B (1.5 g, 3.8 mmol) dropwise at zero degrees C. The solution stirred at 25° C. for 2 hours. The solution was diluted with ethyl acetate and washed with H₂O, 1N H₂SO₄, H₂O, satd. NaCl and dried over MgSO₄. Flash chromatography (15% ethyl acetate/85% hexane) on silica gel provided the sulfide compound as a clear, colorless oil (ethyl 4-[[(4-phenoxyphenyl)thio]methyl]-4-(BOC-piperidine) carboxylate; 1.5 g, 84%). HRMS calcd. for C₂₆H₃₃NO₅S: 471.2063, found 471.2052.

Part D: To a solution of the sulfide compound of Part C (1.47 g, 3.0 mmol) in methylene chloride (60 mL) cooled to zero degrees C., was added meta-chloroperbenzoic acid (80%, 1.29 g, 6.0 mmol). The solution stirred for 1.5 hours at 0° C., and was then washed with H₂O, satd. NaHCO₃, 10% Na₂SO₄, satd. NaCl, and dried over MgSO₄. Chromatography (1:4 ethyl acetate/hexane) provided the sulfone compound as a white foam (ethyl 4-[[(4-phenoxyphenyl)-sulfonyl]methyl]-4-(BOC-piperidine)carboxylate; 920 mg, 61%).

Part E: Into a cooled solution (zero degrees C.) of the sulfone compound of Part D (2.03 g, 4.0 mmol) in ethyl acetate (50 mL) was bubbled HCl gas for 5 minutes and then stirred for 15 minutes. Concentration under a stream of $N_2$ provided the amine hydrochloride salt as a white solid (ethyl 4-[[(4-phenoxyphenyl)-sulfonyl]-methyl]-4-piperidinecarboxylate; 1.57 g, 89%).

Part F: To a suspension of the amine hydrochloride salt of part E (750 mg, 1.7 mmol) in ethanol (30 mL) was added phenyl acetaldehyde (0.134 mL, 1.72 mmol) followed by borane.pyridine (8M, 0.215 mL, 1.72 mmol). After 24 hours of stirring at ambient temperature, additional phenyl acetaldehyde (0.134 mL) and borane.pyridine (0.215 mL) were added. After an additional 24 hours the ethanol was removed in vacuo followed by dilution with $H_2O$. The solution was extracted with dichloromethane and the organic layer was washed with sat. NaCl and dried over $MgSO_4$. Chromatography (ethyl acetate/hexane) provided the benzyl compound as an oil (ethyl 4-[[(4-henoxyphenyl)-sulfonyl]-methyl]-1-(2-phenylethyl)-4-piperidinecarboxylate, monohydrochloride; 690 mg, 80%). HRMS calc'd for $C_{29}H_{33}NO_5S$: 508.2158, found 508.2161.

Part G: To a solution of the benzyl compound of part F (680 mg, 1.3 mmol) in THF (8 mL) and ethanol (8 mL) was added NaOH (520 mg, 13 mmol) in $H_2O$. The solution heated to 65° C. for 18 hours. The solution was concentrated in vacuo and the residue was dissolved in $H_2O$ followed by acidification to pH 2. Extraction with ethyl acetate followed by trituration with ethyl ether provided the carboxylic acid as a beige solid (4-[[(4-phenoxyphenyl)-sulfonyl]-methyl]-1-(2-phenylethyl)-4-piperidinecarboxylic acid, monohydrochloride; 642 mg, quantitative yield). HRMS calc'd for $C_{27}H_{24}NO_5S$: 480.1845, found 480.1854.

Part H: To a solution of the carboxylic acid of part C (850 mg, 1.6 mmol) in DMF was added N-hydroxybenzotriazole.$H_2O$ (267 mg, 1.98 mmol) followed by 1-(3-dimethylaminopropyl)-3-ethylcarbodiimide hydrochloride (429 mg, 2.24 mmol), 4-methylmorpholine (0.527 mL, 4.8 mmol) and 50% aqueous $NH_2OH$ (1.06 mL, 16.0 mmol). The solution stirred for 18 hours at ambient temperature. Additional N-hydroxybenzotriazole.$H_2O$ (267 mg), 1-(3-dimethylaminopropyl)-3-ethylcarbodiimide hydrochloride (429 mg), 4-methylmorpholine (0.527 mL) and 50% aqueous $NH_2OH$ (1.06 mL) was added and the solution stirred for 24 hours. The mixture was diluted with $H_2O$ and extracted with chloroform. The organic layer was washed with satd. NaCl and dried over $MgSO_4$. The hydrochloride salt was formed by the addition of the free base to cold acetyl chloride in ethanol. HPLC (acetonitrile/$H_2O$) provided N-hydroxy-4-[[(4-phenoxyphenyl)sulfonyl]-methyl]-1-(2-phenylethyl)-4-piperidinecarboxamide, monohydrochloride, as a white solid (460 mg, 55%). Anal. calc'd for $C_{27}H_{30}N_2O_5S.0.75H_2O$: C, 59.55; H, 6.02; N, 5.14. Found: C, 59.29; H, 6.04; N, 5.19.

EXAMPLE 3
N-Hydroxy-1-[(3-methoxyphenyl)methyl]-4-[[(4-phenoxyphenyl)sulfonyl]methyl]-4-piperidinecarboxamide, Monohydrochloride

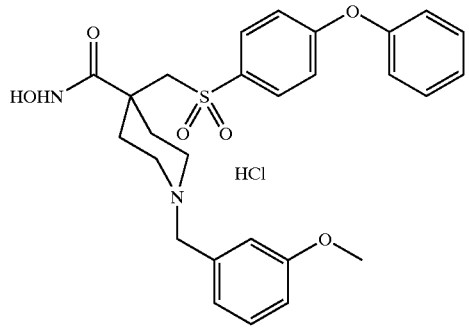

Part A: To a solution of ethyl isonipecotate (ethyl 4-piperidine carboxylate; 15.7 g, 0.1 mol) in tetrahydrofuran (100 mL) was added a solution of di-tert-butyl dicarbonate (di-t-BOC; 21.8 g, 0.1 mol) in THF (5 mL) dropwise over 20 minutes. The solution stirred overnight at ambient temperature and concentrated in vacuo to yield a light oil. The oil was filtered through silica gel (7:3 ethyl acetate/hexane) and concentrated in vacuo to give the BOC-piperidine compound (ethyl 4-[BOC-piperidine]carboxylate; 26.2 g, quantitative yield) as a clear, colorless oil.

Part B: To a solution of the BOC-piperidine compound of Part A (17.56 g, 0.068 mol) in tetrahydrofuran (100 mL) cooled to −42° C. was added lithium diisopropylamine, 1.8M in THF (37.8 mL, 0.068 mol) dropwise to not exceed −40° C. After 1 hour, diiodomethane (5.5 mL, 0.068 mol) was added. The solution was warmed to ambient temperature after the addition was complete and stirred for 5 hours. The solution was diluted with $H_2O$ and extracted with ethyl ether. The organic layer is washed with $H_2O$, satd. NaCl and dried over $MgSO_4$. Concentration provided the iodo compound (ethyl 4-[iodomethyl]-4-[BOC-piperidine] carboxylate; 28.8 g, quantitative yield) as a clear brown oil.

Part C: A suspension of NaH (152 mg of a 60% dispersion in mineral oil, 3.8 mmol) in DMF (3 mL) was cooled to zero degrees C. in an ice/$H_2O$ bath and a solution of 4-(phenoxy) benzenethiol (769 mg, 3.8 mmol) in DMF (5 mL) was added dropwise and stirred until a homogenous solution of sodium 4-(phenoxy)benzene-thiolate resulted. To this solution was added the iodo compound of Part B (1.5 g, 3.8 mmol) dropwise at zero degrees C. The solution stirred at 25° C. for 2 hours. The solution was diluted with ethyl acetate and washed with $H_2O$, 1N $H_2SO_4$, $H_2O$, satd. NaCl and dried over $MgSO_4$. Flash chromatography (15% ethyl acetate/85% hexane) on silica gel provided the sulfide compound as a clear, colorless oil (ethyl 4-[[(4-phenoxyphenyl)thio]-methyl]-4-(BOC-piperidine)carboxylate; 1.5 g, 84%).

Part D: To a solution of the sulfide of Part C (1.47 g, 3.0 mmol) in methylene chloride (60 mL) cooled to 0° C., was added meta-chloroperbenzoic acid (80%, 1.29 g, 6.0 mmol). The solution stirred for 1.5 hours at 0° C., and was then washed with $H_2O$, satd. $NaHCO_3$, 10% $Na_2SO_4$, satd. NaCl, and dried over $MgSO_4$. Chromatography (1:4 ethyl acetate/hexane) provided the sulfone compound as a white foam (ethyl 4-[[(4-phenoxyphenyl)sulfonyl]methyl]-4-(BOC-piperidine)carboxylate; 920 mg, 61%).

Part E: Into a cooled solution (zero degrees C.) of the sulfone of Part D (1.11 g, 2.20 mmol) in ethyl acetate (30 mL) was bubbled HCl gas for 4 minutes. Concentration in vacuo followed by trituration with ethyl ether provided the amine hydrochloride salt as a white solid (ethyl 4-[[(4-phenoxyphenyl)sulfonyl]-methyl]-4-piperidinecarboxylate, monohydrochloride; 774 mg, 80%). Anal. calc'd for $C_{21}H_{25}NO_5S.HCl$: C, 57.33; H, 5.96; N, 3.18; Cl, 8.06. Found: C, 57.29; H, 5.87; N, 3.17; Cl, 8.17.

Part F: To a solution of the amine hydrochloride salt of part E (748 mg, 1.70 mmol) in methanol (7 mL) was added m-anisaldehyde (0.217 mL, 1.78 mmol). After 30 minutes borane.pyridine (8M in pyridine, 0.16 mL, 0.85 mmol) was added. After stirring at ambient temperature for 18 hours additional m-anisaldehyde (0.100 mL, 0.82 mmol) and borane.pyridine (0.106 mL, 0.85 mmol) were added and the solution stirred for 24 hours. To the mixture was added sat. $NaHCO_3$ and the mixture was extracted with ethyl acetate. The organic layers were washed with $H_2O$, satd. NaCl, and dried over $Na_2SO_4$. Chromatography (ethyl acetate/hexane) provided the 3-methoxybenzyl compound as a colorless oil (ethyl 1-[3-(methoxyphenyl)methyl]-4-[[(4-phenoxyphenyl)-sulfonyl]-methyl-4-piperidinecarboxylate, monohydrochloride; 820 mg, 92%). MS(CI) $MH^+$ calc'd for $C_{29}H_{33}NO_6S$: 524, found 524. Anal. calc'd for $C_{29}H_{33}NO_6S \cdot 0.75H_2O$: C, 64.84; H, 6.47; N, 2.61. Found: C, 64.89; H, 6.72; N, 2.51.

Part G: To a solution of the ethyl ester of Part F (800 mg, 1.53 mmol) in ethanol (10 mL) and THF (15 mL) was added NaOH (612 mg, 15.3 mmol) in $H_2O$ (15 mL). The solution was heated to reflux for 16 hours followed by concentration in vacuo. Reverse phase HPLC [acetonitrile/$H_2O$(0.5% HCl)] provided the carboxylic acid as a yellow foam (1-[3-(methoxyphenyl)methyl]-4-[[(4-phenoxyphenyl)sulfonyl] methyl]-4-piperidinecarboxylic acid, monohydrochloride; 891 mg, quantitative yield). HRMS calc'd for $C_{27}H_{29}NO_6S$: 496.1798, found 496.1794. Anal. calc'd for $C_{27}H_{29}NO_6S \cdot HCl$: C, 60.95; H, 5.68; N, 2.63; Cl, 6.66. Found: C, 60.93; H, 6.02; N, 2.06; Cl, 5.84.

Part H: To a solution of the carboxylic acid compound of part G (841 mg, 1.62 mmol) in DMF (6.5 mL) was added N-hydroxybenzotriazole.$H_2O$ (263 mg, 1.94 mmol) and 4-methylmorpholine (0.712 mL, 6.5 mmol) and the solution was cooled to zero degrees C. To this solution was added 50% aqueous $NH_2OH$ (0.128 mL, 1.94 mmol) and 1-(3-dimethylaminopropyl)-3-ethylcarbodiimide hydrochloride (372 mg, 1.94 mmol). The solution stirred for 20 hours at ambient temperature. Additional N-hydroxybenzotriazole.$H_2O$ (263 mg), 4-methylmorpholine (0.712 mL), 1-(3-dimethylaminopropyl)-3-ethylcarbodiimide hydrochloride (372 mg) and 50% aqueous $NH_2OH$ (0.128 mL) were added and the solution stirred an additional 24 hours. After concentration under a stream of $N_2$ the residue was dissolved in ethyl acetate and washed with sat'd $NaHCO_3$. Insoluble material was removed by filtration and the aqueous layer was extracted three times with ethyl acetate. The combined organic layers were washed with $H_2O$ and sat'd NaCl and dried over $Na_2SO_4$. Following concentration in vacuo the residue was dissolved in ethyl acetate and HCl gas was bubbled into the solution for 15 seconds. The solution was concentrated under a stream of $N_2$. Reverse phase HPLC (acetonitrile/$H_2O$) provided N-hydroxy-1-[(3-methoxyphenyl)methyl]-4-[[(4-phenoxyphenyl)sulfonyl] methyl]-4-piperidine carboxamide, monohydrochloride as a white solid (102 mg, 11%). HPLC purity: 93.3%. MS(EI) $M^+$ calc'd for $C_{27}H_{30}N_2O_6S$: 511, found 511. HRMS calc'd for $C_{27}H_{30}N_2O_6S$: 511.1903, found 511.1907.

EXAMPLE 4

N-Hydroxy-4-[[(4-phenoxyphenyl)sulfonyl]-methyl]-1-(2-propynyl)-4-piperidinecarboxamide, Monohydrochloride

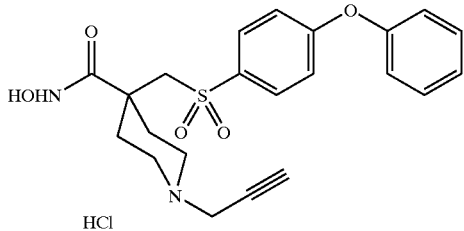

Part A: To a solution of ethyl isonipecotate (ethyl 4-piperidinecarboxylate; 15.7 g, 0.1 mol) in tetrahydrofuran (100 mL) was added a solution of di-tert-butyl dicarbonate (di-t-BOC; 21.8 g, 0.1 mol) in THF (5 mL) dropwise over 20 minutes. The solution stirred overnight at ambient temperature and concentrated in vacuo to yield a light oil. The oil was filtered through silica gel (7:3 ethyl acetate/hexane) and concentrated in vacuo to give the BOC-piperidine compound (ethyl 4-(BOC-piperidine)carboxylate; 26.2 g, quantitative yield) as a clear, colorless oil.

Part B: To a solution of the BOC-piperidine compound of Part A (17.56 g, 0.068 mol) in tetrahydrofuran (100 mL) cooled to −42° C. was added lithium diisopropylamine, 1.8M in THF (37.8 mL, 0.068 mol) dropwise to not exceed −40° C. After 1 hour diiodomethane (5.5 mL, 0.068 mol) was added. The solution was warmed to ambient temperature after the addition was completed and stirred for 5 hours. The solution was diluted with $H_2O$ and extracted with ethyl ether. The organic layer was washed with $H_2O$, sat'd NaCl and dried over $MgSO_4$. Concentration provided the iodo compound (ethyl-4-[iodomethyl]-4-(BOC-piperidine) carboxylate; 28.8 g, quantitative yield) as a clear brown oil.

Part C: A suspension of NaH (152 mg as a 60% dispersion in mineral oil, 3.8 mmol) in DMF (3 mL) was cooled to zero degrees C. on an ice/$H_2O$ bath and a solution of 4-(phenoxy) benzenethiol (769 mg, 3.8 mmol) in DMF (5 mL) was added dropwise and stirred until a homogenous solution of sodium thiolate resulted. To this solution was added the iodo compound of Part B (1.5 g, 3.8 mmol) dropwise at zero degrees C. The solution stirred at 25° C. for 2 hours. The solution is diluted with ethyl acetate and washed with $H_2O$, 1N $H_2SO_4$, $H_2O$, sat'd NaCl, and dried over $MgSO_4$. Flash chromatography (15% ethyl acetate/85% hexane) on silica gel provided the sulfide compound as a clear, colorless oil (ethyl 4-[[(4-phenoxyphenyl)thio]methyl]-4-(BOC-piperidine) carboxylate; 1.5 g, 84%). HRMS calcd. for $C_{26}H_{33}NO_5S$: 471.2063, found 471.2052.

Part D: To a solution of the sulfide of Part C (1.47 g, 3.0 mmol) in methylene chloride (60 mL) cooled to 0° C., was added meta-chloroperbenzoic acid (80%, 1.29 g, 6.0 mmol). The solution stirred for 1.5 hours at 0° C., and was then washed with $H_2O$, satd. $NaHCO_3$, 10% $Na_2SO_4$, satd. NaCl, and dried over $MgSO_4$. Chromatography (1:4 ethyl acetate/ hexane) provided the sulfone compound as a white foam (ethyl 4-[[(4-phenoxyphenyl)sulfonyl]methyl]-4-(BOC-piperidine)carboxylate; 920 mg, 61%).

Part E: Into a cooled solution (zero degrees C.) of the sulfone of Part D (2.03 g, 4.0 mmol) in ethyl acetate (50 mL) was bubbled HCl gas for 5 minutes and then stirred for 15 minutes. Concentration under a stream of $N_2$ provided the amine hydrochloride salt as a white solid (ethyl 4-[[(4-phenoxyphenyl)sulfonyl]methyl]-4-piperidinecarboxylate, monohydrochloride; 1.57 g, 89%).

Part F: To a solution of amine hydrochloride salt of Part E (750 mg, 1.7 mmol) in DMF (10 mL) was added potassium carbonate (469 mg, 3.4 mmol) followed by propargyl bromide (1-bromo-2-propyne; 80% in toluene, 253 mg, 1.7 mmol) and was stirred for 5 hours. The solution was diluted with ethyl acetate and washed with $H_2O$, satd. NaCl, and dried over $MgSO_4$. Purification via filtration through a silica pad (ethyl acetate) provided the propargyl amine as an oil (ethyl 4-[[(4-phenoxyphenyl)sulfonyl-methyl]-1-(2-propynyl)-4-piperidinecarboxylate, monohydrochloride; 620 mg, 82%).

Part G: To a solution of the propargyl amine of Part F (620 mg, 1.4 mmol) in ethanol (5 mL) and THF (5 mL) was added NaOH (560 mg, 1.4 mmol) in 10 mL $H_2O$. The mixture was submerged in an oil bath at 62° C. and stirred for 18 hours. The solution was diluted with $H_2O$ and extracted with ethyl acetate. The aqueous was acidified to pH=4 and the resulting beige solid was collected by vacuum filtration. Drying under high vacuum at 40° C. for 18 hours provided the carboxylic acid as a light beige solid (4-[[(4-phenoxyphenyl)-sulfonyl]-methyl]-1-(2-propynyl)-4-piperidinecarboxylic acid, monohydrochloride; 473 mg, 82%). MS(CI) MH+ calcd. for $C_{22}H_{23}NO_5S$: 414, found 414. HRMS calc'd for $C_{22}H_{23}NO_5S$: 414.1375, found 414.1382. Anal. calc'd for $C_{22}H_{23}NO_5S \cdot HCl \cdot 0.5H_2O$: C, 57.57; H, 5.49; N, 3.05; Cl, 7.72; S, 6.99. Found: C, 57.59; H, 4.91; N, 2.72; Cl, 7.93; S, 6.76.

Part H: To a solution of the carboxylic acid of Part G (460 mg, 1.1 mmol) in DMF (10 mL) was added N-hydroxbenzotriazole.$H_2O$ (180 mg, 1.33 mmol) and after 5 minutes of stirring was added 1-(3-dimethylaminopropyl)-3-ethylcarbodiimide hydrochloride (299 mg, 1.56 mmol). After 10 additional minutes 4-methylmorpholine (0.49 mL, 4.45 mmol) and 50% aqueous hydroxylamine (0.22 mL, 3.34 mmol) and the solution stirred for 24 hours. An additional aliquot of each reagent was added and the solution stirred for an additional 48 hours. The solution was diluted with $H_2O$, extracted with chloroform, washed with satd. NaCl and dried over $MgSO_4$. Reverse phase HPLC (acetonitrile/$H_2O$) provided the hydroxamate compound as a white solid (N-hydroxy-4-[[(4-phenoxyphenyl)-sulfonyl]-methyl]-1-(2-propynyl)-4-piperidinecarboxamide, monohydrochloride; 200 mg, 42%). HRMS calc'd for $C_{22}H_{24}N_2O_5S$: 429.1489, found 429.1480. Anal. calc'd for $C_{22}H_{24}N_2O_5S$: C, 61.66; H, 5.64; N, 6.54; S, 7.48. Found: C, 61.33; H, 5.68; N, 6.36; S, 7.35.

Part I: To a cooled (0° C.) solution of acetyl chloride (0.429 mL, 0.658 mmol) in methanol (2 mL) was added the hydroxamate of part H (141 mg, 0.324 mmol) in methanol (5 mL). The solution stirred for 20 minutes at zero degrees C. Concentration under a stream of $N_2$ followed by trituration with ethyl ether provided (N-hydroxy-4-[[(4-phenoxyphenyl)-sulfonyl]-methyl]-1-(2-propynyl)-4-piperidinecarboxamide, monohydrochloride as a white solid (154 mg, quantitative yield). HPLC purity: >99%. Anal. calcd. for $C_{22}H_{24}N_2O_5S \cdot 1.05HCl \cdot 0.45H_2O$: C, 55.64; H, 5.51; N, 5.90; Cl, 7.84. Found: C, 55.42; H, 5.63; N, 5.79; Cl, 8.02.

EXAMPLE 5

1,1-Dimethylethyl Ester 4-[(Hydroxyamino)-carbonyl]-4-[[(4-phenoxyphenyl]sulfonyl]methyl]-1-piperidinecarboxylic Acid

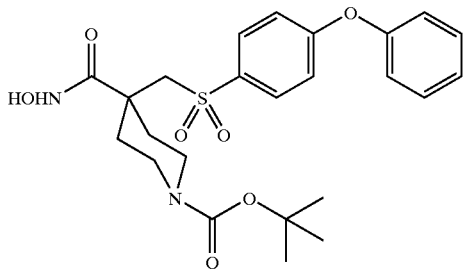

Part A: To a solution of ethyl isonipecotate (ethyl 4-piperidinecarboxylate; 15.7 g, 0.1 mol) in tetrahydrofuran (100 mL) was added a solution of di-tert-butyl dicarbonate (di-t-BOC; 21.8 g, 0.1 mol) in THF (5 mL) dropwise over 20 minutes. The solution stirred overnight at ambient temperature and concentrated in vacuo to yield a light oil. The oil was filtered through silica gel (7:3 ethyl acetate/hexane) and concentrated in vacuo to give the BOC-piperidine compound (ethyl 4-(BOC-piperidine)carboxylate; 26.2 g, quantitative yield) as a clear, colorless oil.

Part B: To a solution of the BOC-piperidine compound of Part A (17.56 g, 0.068 mol) in tetrahydrofuran (100 mL) cooled to −42° C. was added lithium diisopropylamine, 1.8M in THF (37.8 mL, 0.068 mol) dropwise to not exceed −40° C. After 1 hour diiodomethane (5.5 mL, 0.068 mol) was added. The solution was warmed to ambient temperature after the addition was complete and stirred for 5 hours. The solution was diluted with $H_2O$ and extracted with ethyl ether. The organic layer is washed with $H_2O$, satd. NaCl and dried over $MgSO_4$. Concentration provided the iodo compound (ethyl 4-[iodomethyl]-4-(BOC-piperidine)carboxylate; 28.8 g, quantitative yield) as a clear brown oil.

Part C: A suspension of NaH (152 mg as a 60% dispersion in mineral oil, 3.8 mmol) in DMF (3 mL) was cooled to zero degrees C. on an ice/$H_2O$ bath and a solution of 4-(phenoxy) benzenethiol (769 mg, 3.8 mmol) in DMF (5 mL) was added dropwise and stirred until a homogenous solution resulted. To this solution was added the iodo compound of Part B (1.5 g, 3.8 mmol) dropwise at zero degrees C. The solution stirred at 25° C. for 2 hours. The solution was diluted with ethyl acetate and washed with $H_2O$, 1N $H_2SO_4$, $H_2O$, satd. NaCl and dried over $MgSO_4$. Flash chromatography (15% ethyl acetate/85% hexane) on silica gel provided the sulfide compound as a clear, colorless oil (ethyl 4-[[(4-phenoxyphenyl)thio]methyl]-4-(BOC-piperidine)carboxylate; 1.5 g, 84%). HRMS calcd for $C_{26}H_{33}NO_5S$, 471.2079, found 471.2063.

Part D: To a solution of the sulfide compound of Part C (1.47 g, 3.0 mmol) in methylene chloride (60 mL) cooled to zero degrees C., was added meta-chloroperbenzoic acid (80%, 1.29 g, 6.0 mmol). The solution stirred for 1.5 hours at zero degrees C., and was then washed with $H_2O$, satd. $NaHCO_3$, 10% $Na_2SO_4$, satd. NaCl, and dried over $MgSO_4$. Chromatography (1:4 ethyl acetate/hexane) provided the sulfone compound as a white foam (ethyl 4-[[(4-phenoxyphenyl)sulfonyl]-methyl]1-piperidine)carboxylate 920 mg, 61%).

Part E: To a solution of the sulfone compound of Part D (920 mg, 1.8 mmol) in ethanol (5 mL)/THF (5 mL) was added sodium hydroxide (731 mg, 1.8 mmol) in $H_2O$ (7 mL). The solution was submerged in a oil bath at 62° C. and stirred for 24 hours. After an additional 24 hours at ambient temperature the solution was extracted with ethyl acetate. The aqueous layer was acidified and extracted with ethyl acetate, washed with satd. NaCl, and dried over $MgSO_4$. Concentration in vacuo provided the carboxylic acid as a white solid (4-[[(4-phenoxyphenyl)sulfonyl]methyl]1-piperidine)carboxylic acid; 770 mg, 89%).

Part F: To a solution of the carboxylic acid of Part E (850 mg, 1.8 mmol) in DMF (7 mL) was added N-hydroxybenzotriazole.$H_2O$ (290 mg, 2.1 mmol) followed, after 5 minutes, by 1-(3-dimethylaminopropyl)-3-ethylcarbodiimide hydrochloride (480 mg, 2.5 mmol). After stirring for 2.5 hours, 4-methylmorpholine (0.59 mL, 5.4 mmol) and 50% aqueous hydroxylamine (0.35 mL, 5.4 mmol) was added and the solution stirred overnight at ambient temperature. An additional aliquot of each of the reagents was added. After an additional 24 hours at ambient temperature the solution was diluted with $H_2O$ and extracted with ethyl acetate. The combined extracts were washed with sat'd NaCl and dried over $MgSO_4$. Reverse phase HPLC (acetonitrile/$H_2O$) provided 1,1-dimethylethyl ester 4-[hydroxyamino)-carbonyl]-4-[[(4-phenoxyphenyl)-sulfonyl]methyl]-1-piperidinecarboxylic acid as a white solid (480 mg, 55%). Anal. calc'd for $C_{24}H_{30}N_2O_7S$: C, 58.76; H, 6.16; N, 5.71; S, 6.54. Found: C, 58.64; H, 6.24; N, 5.66; S, 6.66.

EXAMPLE 6

N-Hydroxy-4-[[(4-phenoxyphenyl)sulfonyl]-methyl]-4-piperidinecarboxamide, Monohydrochloride

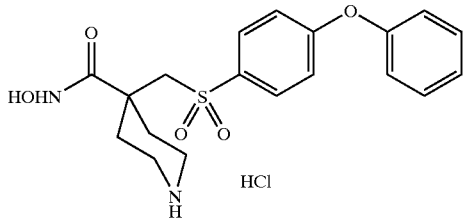

Part A: To a solution of ethyl isonipecotate (ethyl 4-piperidinecarboxylate; 15.7 g, 0.1 mol) in tetrahydrofuran (100 mL) was added a solution of di-tert-butyl dicarbonate (di-t-BOC; 21.8 g, 0.1 mol) in THF (5 mL) dropwise over 20 minutes. The solution stirred overnight at ambient temperature and concentrated in vacuo to yield a light oil. The oil was filtered through silica gel (7:3 ethyl acetate/hexane) and concentrated in vacuo to give the BOC-piperidine compound (ethyl 4-(BOC-piperidine)carboxylate; 26.2 g, quantitative yield) as a clear, colorless oil.

Part B: To a solution of the BOC-piperidine compound of Part A (17.56 g, 0.068 mol) in tetrahydrofuran (100 mL) cooled to −42° C. was added lithium diisopropylamine, 1.8M in THF (37.8 mL, 0.068 mol) dropwise to not exceed −40° C. After 1 hour diiodomethane (5.5 mL, 0.068 mol) was added. The solution was warmed to ambient temperature after the addition was complete and stirred for 5 hours. The solution was diluted with $H_2O$ and extracted with ethyl ether. The organic layer is washed with $H_2O$, satd. NaCl and dried over $MgSO_4$. Concentration provided the iodo compound (ethyl 4-[iodomethyl]-4-(BOC-piperidine)carboxylate; 28.8 g, quantitative yield) as a clear brown oil.

Part C: A suspension of NaH (152 mg of a 60% dispersion in mineral oil, 3.8 mmol) in DMF (3 mL) was cooled to zero degrees C. on an ice/$H_2O$ bath and a solution of 4-(phenoxy)benzenethiol (769 mg, 3.8 mmol) in DMF (5 mL) was added dropwise and stirred until a homogenous solution of sodium 4-(phenoxy)benzenethiolate resulted. To this solution was added the iodo compound of Part B (1.5 g, 3.8 mmol) dropwise at zero degrees C. The solution stirred at 25° C. for 2 hours. The solution was diluted with ethyl acetate and washed with $H_2O$, 1N $H_2SO_4$, $H_2O$, satd. NaCl and dried over $MgSO_4$. Flash chromatography (15% ethyl acetate/85% hexane) on silica gel provided the sulfide compound as a clear, colorless oil (ethyl 4-[[(4-phenoxyphenyl)thio]-methyl]-4-(BOC-piperidine)carboxylate; 1.5 g, 84%). HRMS calc'd for $C_{26}H_{33}NO_5S$, 471.2079, found 471.2063.

Part D: To a solution of the sulfide of Part C (1.47 g, 3.0 mmol) in methylene chloride (60 mL) cooled to zero degrees C., was added meta-chloroperbenzoic acid (80%, 1.29 g, 6.0 mmol). The solution stirred for 1.5 hours at zero degrees C., and was then washed with $H_2O$, satd. $NaHCO_3$, 10% $Na_2SO_4$, satd. NaCl, and dried over $MgSO_4$. Chromatography (1:4 ethyl acetate/hexane) provided the sulfone compound as a white foam (ethyl 4-[[(4-phenoxyphenyl)sulfonyl]-methyl]-4-(BOC-piperidine)carboxylate; 920 mg, 61%).

Part E: To a solution of the sulfone compound of Part D (920 mg, 1.8 mmol) in ethanol (5 mL)/THF (5 mL) was added sodium hydroxide (731 mg, 1.8 mmol) in $H_2O$ (7 mL). The solution was submerged in a oil bath at 62° C. and stirred for 24 hours. After an additional 24 hours at ambient temperature the solution was extracted with ethyl acetate. The aqueous layer was acidified and extracted with ethyl acetate, washed with sat'd NaCl, and dried over $MgSO_4$. Concentration in vacuo provided the carboxylic acid as a white solid (4-[[(4-phenoxyphenyl)sulfonyl]-methyl]-4-(BOC-piperidine)carboxylic acid; 770 mg, 89%).

Part F: To a solution of the carboxylic acid of Part E (850 mg, 1.8 mmol) in DMF (7 mL) was added N-hydroxybenzotriazole.$H_2O$ (290 mg, 2.1 mmol) followed, after 5 minutes, by 1-(3-dimethylaminopropyl)-3-ethylcarbodiimide hydrochloride (480 mg, 2.5 mmol). After stirring for 2.5 hours, 4-methylmorpholine (0.59 mL, 5.4 mmol) and 50% aqueous hydroxylamine (0.35 mL, 5.4 mmol) was added and the solution stirred overnight at ambient temperature. An additional aliquot of each of the reagents was added. After an additional 24 hours at ambient temperature the solution was diluted with $H_2O$ and extracted with ethyl acetate. The combined extracts were washed with sat. NaCl and dried over $MgSO_4$. Reverse phase HPLC ($CH_3CN/H_2O$) provided the hydroxamate as a white solid (N-hydroxy-4-[[(4-phenoxyphenyl)sulfonyl]-methyl]-4-(BOC-piperidine)-carboxamide; 480 mg, 55%). Anal. calc'd for $C_{24}H_{30}N_2O_7S$: C, 58.76; H, 6.16; N, 5.71; S, 6.54. Found: C, 58.64; H, 6.24; N, 5.66; S, 6.66.

Part G: HCl gas was bubbled into a solution of the hydroxamate of part F (499 mg, 1.02 mmol) in ethyl acetate (20 mL) cooled to zero degrees C., for 2 minutes, and was allowed to stir for 0.5 hour. Trituration with ethyl ether provided N-hydroxy-4-[[(4-phenoxyphenyl)-sulfonyl]-methyl]-4-piperidinecarboxamide, monohydrochloride, as a white solid (432 mg, quantitative yield). HRMS calc'd for $C_{19}H_{22}N_2O_5S$: 391.1328, found 391.1349. Anal. calc'd for $C_{19}H_{22}N_2O_5S.HCl.H_2O$: C, 51.29; H, 5.66; N, 6.30; Cl, 7.97; S, 7.21. Found: C, 50.87; H, 5.24; N, 6.22; Cl, 8.24; S, 7.07.

EXAMPLE 7

N-Hydroxy-4-[[[4-(3,4-dimethylphenoxy)phenyl]sulfonyl]-methyl]-1-(2-propynyl)-4-piperidinecarboxamide, Monohydrochloride

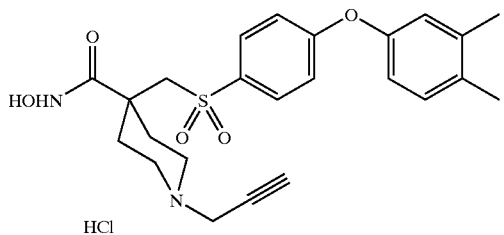

Part A: To a solution of ethyl isonipecotate (ethyl 4-piperidinecarboxylate; 15.7 g, 0.1 mol) in tetrahydrofuran (100 mL) was added a solution of di-tert-butyl dicarbonate (di-t-BOC; 21.8 g, 0.1 mol) in THF (5 mL) dropwise over 20 minutes. The solution stirred overnight at ambient temperature and concentrated in vacuo to yield a light oil. The oil was filtered through silica gel (7:3 ethyl acetate/hexane) and concentrated in vacuo to give the BOC-piperidine compound (ethyl 4-(BOC-piperidine)carboxylate; 26.2 g, quantitative yield) as a clear, colorless oil.

Part B: To a solution of the BOC-piperidine compound of Part A (17.56 g, 0.068 mol) in tetrahydrofuran (100 mL)

cooled to −42° C. was added lithium diisopropylamine, 1.8M in THF (37.8 mL, 0.068 mol) dropwise to not exceed −40° C. After 1 hour diiodomethane (5.5 mL, 0.068 mol) was added. The solution was warmed to ambient temperature after the addition was complete and stirred for 5 hours. The solution was diluted with $H_2O$ and extracted with ethyl ether. The organic layer was washed with $H_2O$, satd. NaCl and dried over $MgSO_4$. Concentration provided the iodo compound (ethyl 4-[iodomethyl]-4-(BOC-piperidine) carboxylate; 28.8 g, quantitative yield) as a clear brown oil.

Part C: To a solution of 4-fluoroacetophenone (4-fluorophenyl methyl ketone; 27.63 g, 0.20 mol) and 3,4-dimethylphenol (24.43 g, 0.20 mol) in dimethylacetamide (200 mL) was added $K_2CO_3$ (33.17 g, 0.24 mol) and the mixture heated to reflux for 8 hours. After concentration of solvent the residue was dissolved in ethyl acetate (400 mL) and $H_2O$ (200 mL), washed with 1N HCl (200 mL) and sat. NaCl (200 mL) and dried over $Na_2SO_4$. Recrystallization from hot ethyl acetate/hexanes provided the acetophenone compound as a solid (28.5 g, 59%). HPLC purity: 99%.

Part D: To a solution of the acetophenone compound of part C (26.04 g, 108.4 mmol) in methanol (590 mL) and $H_2O$ (65 mL) was added Oxone® (133 g, 216.7 mmol). The mixture was heated to reflux for 5.5 hours and after cooling to ambient temperature, the excess Oxone® was removed by filtration and was washed with methanol. After concentration of solvent the residue was dissolved in ethyl acetate (400 mL) and washed with $H_2O$ (300 mL) and dried over $Na_2SO_4$. Purification by chromatography (10% ethyl acetate/hexanes to 20% ethyl acetate/hexanes) provided the phenol compound as a solid (13.98 g, 60%). HPLC purity: >99%. MS(CI) MH⁺ calc'd for $C_{14}H_{14}O_2$: 215, found 215.

Part E: To a solution of KOH (8 g, 143 mmol) in $H_2O$ (85 mL), cooled to 0° C., was added the phenol compound of Part D (13.7 g, 64.0 mmol) followed by the dropwise addition of dimethylthiocarbamoyl chloride (10.6 g, 85.8 mmol) in THF (75 mL). The solution stirred for 4.5 hours at zero degrees C. followed by extraction with toluene (2×125 mL). The organic layers were combined and dried over $MgSO_4$. Purification by chromatography (95:5 hexane/ethyl acetate with 1% triethylamine) provided the thiocarbamate compound as a white solid (10.9 g, 56%). HPLC purity: >99%.

Part F: The thiocarbamate compound of Part E (10.9 g, 53.6 mmol) was heated to 290° C. for 15 minutes. The compound was cooled to ambient temperature and dissolved into an 8:1 mixture of ethylene glycol/$H_2O$. Added to this solution was KOH (9.0 g, 161 mmol) and the mixture stirred for 1.5 hours. The mixture was poured over ice (125 g) and conc. HCl (6 mL) was added. The mixture was extracted with chloroform (1×100 mL) and dichloromethane (2×60 mL) and the combined organic layers were dried over $MgSO_4$. Purification by chromatography (hexane) provided the thiophenol as a colorless liquid (4-(3,4-dimethylphenoxy)benzenethiol; 4.0 g, 32%).

Part G: A suspension of NaH (600 mg of a 60% dispersion in mineral oil, 15 mmol) in DMF (10 mL) was cooled to zero degrees C. and the thiophenol compound of part F (3.45 g, 15 mmol) in DMF (7 mL) was added dropwise to generate the sodium thiophenolate anion. After the solution was homogeneous, the iodo compound of part B (5.96 g, 15 mmol) in DMF (10 mL) was added. The solution stirred for 30 minutes at zero degrees C. and for 4 hours at ambient temperature. The reaction was quenched by the addition of $H_2O$ and was extracted with ethyl acetate. The combined organic layers were washed with satd. NaCl and dried over $MgSO_4$. Chromatography (ethyl acetate/hexane) provided the sulfide compound as a clear oil (ethyl 4-[[[4-(3,4-dimethylphenoxy)-phenyl]-thio]-methyl]-4-(BOC-piperidine)carboxylate; 6.45 g, 86%).

Part H: To a solution of the sulfide compound of part G (6.45 g, 13 mmol) in dichloromethane (100 mL) was added m-chloroperbenzoic acid (4.45 g, 26 mmol). The solution was stirred at zero degrees C. for 3 hours. The solution was diluted with dichloromethane and washed with $H_2O$ and sat'd NaCl, and dried over $MgSO_4$. Chromatography (ethyl acetate/hexane) provided the sulfone compound as a white solid (ethyl 4-[[[4-(3,4-dimethylphenoxy)-phenyl]-sulfonyl]-methyl]-4-(BOC-piperidine)carboxylate; 6.7 g, 98%). Anal. calc'd for $C_{28}H_{37}NO_7S\cdot H_2O$: C, 61.18; H, 7.15; N, 2.55; S, 5.83. Found: C, 61.32; H, 7.11; N, 2.44; S, 5.16.

Part I: Into a solution of the sulfone compound of part H (6.7 g, 13 mmol) cooled to zero degrees C. was bubbled HCl gas for 15 minutes. The solution was concentrated in vacuo and trituration with ethyl ether provided the amine hydrochloride salt as a white solid (ethyl 4-[[[4-(3,4-dimethylphenoxy)-phenyl]-sulfonyl]-methyl]-4-piperidinecarboxylate, monohydrochloride; 5.4 g, 89%). MS(CI) MH⁺ calc'd for $C_{23}H_{30}NO_5S$: 432, found 432.

Part J: To a solution of the amine hydrochloride salt of part I (5.4 g, 11 mmol) and $K_2CO_3$ (3.17 g, 23 mmol) in DMF (70 mL) was added propargyl bromide (1-bromo-2-propyne; 0.98 mL, 11 mmol) and the solution stirred for 4 hours. The solution was diluted with $H_2O$ and extracted with ethyl acetate. The organic layer was washed with satd. NaCl and dried over $MgSO_4$. Chromatography (ethyl acetate/hexane) provided the propargyl amine compound (ethyl 4-[[[4-(3,4-dimethylphenoxy)-phenyl]-sulfonyl]-methyl]-1-(2-propynyl)-4-piperidinecarboxylate, monohydrochloride; 4.28 g, 82%). HRMS calc'd for $C_{26}H_{31}NO_5S$: 469.1923, found 469.1908. Anal. calc'd for $C26H_{31}NO_5S\cdot 0.5CH_3CH_2COOCH_3$: C, 65.47; H, 6.87; N, 2.73; S, 6.24. Found: C, 65.50; H, 7.02; N, 2.66; S, 6.15.

Part K: To a solution of the propargyl amine compound of part J (4.13 g, 8.79 mmol) in THF (50 ml) and ethanol (50 mL) was added NaOH (3.52 g, 87.95 mmol) in $H_2O$ (30 mL) and the solution was heated at 65° C. for 18 hours. Additional NaOH (703 mg, 17.58 mmol) was added and the solution heated at 65° C. for 18 hours. The solvent was concentrated in vacuo and the aqueous residue was extracted with ethyl acetate. The aqueous layer was acidified to pH 2 and extracted with ethyl acetate. Following concentration in vacuo the white residue was triturated with ethyl ether to provide the carboxylic acid as a white solid (4-[[4-(3,4-dimethylphenoxy)-phenyl]-sulfonyl]-methyl]-1-(2-propynyl)-4-piperidinecarboxylic acid, monohydrochloride; 3.8 g, quantitative yield). HRMS calc'd for $C_{24}H_{27}NO_5S$: 441.1608, found 441.1651.

Part L: To a solution of the carboxylic acid of part K (1.0 g, 2.26 mmol) in dichloromethane (10 mL) was added triethylamine (0.945 mL, 6.78 mmol) and 50% aqueous hydroxylamine (1.5 mL, 2.26 mmol) followed by PyBroP® (1.16 g, 2.48 mmol) and the suspension stirred for 5 hours. The unreacted starting material was removed by filtration and the filtrate was diluted with dichloromethane and washed with satd. NaCl and dried over $MgSO_4$. Reverse phase chromatography provided the hydroxamate as a white solid (N-hydroxy-4-[[[4-(3,4-dimethylphenoxy)-phenyl]-sulfonyl]-methyl]-1-(2-propynyl)-4-piperidinecarboxamide, monohydrochloride; 215 mg, 21%). Anal. calcd. for $C_{24}H_{28}N_2O_5S$: C, 63.14; H, 6.18; N, 6.14; S, 7.02. Found: C, 62.78; H, 6.06; N, 6.17; S, 6.86.

Part M: To a solution of the propargyl amine compound of part L (205 mg, 0.449 mmol) in methanol (4 mL) cooled to zero degrees C. was added a cooled solution of acetyl chloride (0.035 mL, 0.494 mmol) in methanol (1 mL). The solution stirred for 30 minutes at ambient temperature. Concentration under a stream of $N_2$ followed by trituration with ethyl ether provided N-hydroxy-4-[[[4-(3,4-dimethylphenoxy)-phenyl]sulfonyl]-methyl]-1-(2-propynyl)-4-piperidinecarboxamide, monohydrochloride, as a white solid (191 mg, 86%). MS(CI) MH$^+$ calc'd for $C_{24}H_{28}N_2O_5S$: 457, found 457. Anal. calc'd for $C_{24}H_{28}N_2O_5S \cdot HCl \cdot H_2O$: C, 57.42; H, 6.02; N, 5.58; Cl, 7.06. Found: C, 57.36; H, 6.32; N, 5.68; S, 6.84.

EXAMPLE 8

N-Hydroxy-2-[[(4-phenoxyphenyl)sulfonyl]-methyl]-1-(2-propynyl)-2-pyrrolidine Carboxamide, Monohydrochloride

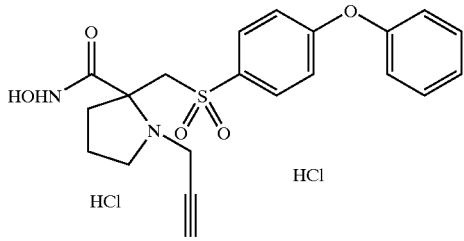

Part A: To a solution of CBZ-proline methyl ester (2.0 g, 7.6 mmol) in THF (10 mL) cooled to –76° C. was added lithium diisopropylamine, 1.8M in THF (4.5 mL, 8.1 mmol) and the solution was stirred for 1 hour. To this solution was added diiodomethane (0.67 mL, 8.3 mmol) and the solution was stirred for 20 hours at ambient temperature. The solution was concentrated and the residue was dissolved into ethyl acetate and washed with $H_2O$ and dried over $MgSO_4$. Chromatography (ethyl acetate/hexane) provided the iodo compound as a yellow oil (980 mg, 32%)

Part B: To a solution of 4-(phenoxy)benzenethiol (2.0 g, 9.9 mmol) in DMF (3 mL) was added NaH (60% suspension in mineral oil, 400 mg, 10 mmol) and the solution stirred at zero degrees C. for 30 minutes. This solution was added to a solution of the iodo compound of part A (4.0 g, 9.9 mmol) in DMF (4 mL) and the mixture was stirred for 18 hours at ambient temperature. The solution was concentrated in vacuo and the residue was dissolved into ethyl acetate and washed with $H_2O$ and dried over $MgSO_4$. Chromatography (ethyl acetate/hexane) provided the sulfide as a yellow oil (1.9 g, 40%).

Part C: To a solution of the sulfide of part B (1.9 g, 4.0 mmol) in methanol (300 mL) and $H_2O$ (30 mL) was added Oxone® and the mixture was stirred for 20 hours at ambient temperature. The excess solids were collected by filtration and the filtrate was concentrated in vacuo. The residue was dissolved in ethyl acetate and washed with $H_2O$ and dried over $MgSO_4$. Concentration in vacuo provided the sulfone as a yellow solid (2.0 g, 98%).

Part D: To a solution of 10% Pd on C (410 mg, 0.38 mmol) in methanol (40 mL) was added the sulfone of part C (2.0 g, 3.9 mmol) and the solution stirred under a $H_2$ atmosphere for 20 hours at ambient temperature. The mixture was filtered and the filtrate was concentrated. Chromatography (ethyl acetate/hexane) provided the amine as an oil (1.0 g, 69%).

Part E: To a solution of the amine of part D (1.0 g, 2.6 mmol) in DMF (10 mL) was added $K_2CO_3$ (1.1 g, 7.9 mmol) and propargyl bromide (0.40 mL, 5.3 mmol) and the solution stirred for 20 hours at ambient temperature. The solution was concentrated in vacuo and the residue was dissolved into 1M $KHSO_4$. The solution was extracted with ethyl ether and the aqueous was made basic with saturated $NaHCO_3$. The aqueous layer was extracted with ethyl acetate, and concentration in vacuo provided the propargyl amine as a solid (600 mg, 51%).

Part F: To a solution of the propargyl amine of part E (500 mg, 1.1 mmol) in methanol (5 mL) and THF (5 mL) was added NaOH (440 mg, 11 mmol) in $H_2O$ (10 mL) and the solution was heated to reflux for 20 hours. The solution was concentrated in vacuo and the residue was dissolved into $H_2O$. The solution was extracted with ethyl ether and the aqueous portion was acidified with concentrated HCl to pH=3. The resulting white precipitate was collected by filtration to provide the acid (400 mg, 76%).

Part G: To a solution of the acid of part F (320 mg, 0.80 mmol) in DMF (10 mL) was added 1-(3-dimethylaminopropyl)-3-ethylcarbodiimide hydrochloride (510 mg, 2.7 mmol) and N-hydroxybenzotriazole (370 mg, 2.7 mmol) followed by N-methylmorpholine (0.36 mL, 3.2 mmol) and 50% aqueous hydroxylamine (0.5 mL). The solution was stirred for 20 hours at ambient temperature. The solution was then concentrated in vacuo and the residue was dissolved into ethyl acetate. The ethyl acetate solution was washed with $H_2O$ and dried over $MgSO_4$. After concentration in vacuo, the residue was dissolved into acetonitrile and concentrated HCl was added to form the HCl salt. Reverse phase chromatography (acetonitrile/$H_2O$) provided the title compound as a white solid (130 mg, 36%). MS(CI) MH$^+$ calcd. for $C_{21}H_{22}N_2O_5S$: 415, found 415. Anal. calc. for $C_{21}H_{22}N_2O_5S \cdot HCL$: C, 55.93; H, 5.14; N, 6.21. Found: C, 55.76; H, 5.37; N, 5.72.

EXAMPLE 9

In vitro Metalloprotease Inhibition

The compounds prepared in the manner described in Examples 1 to 9 were assayed for activity by an in vitro assay. Following the procedures of Knight et al., *FEBS Lett.* 296(3):263 (1992). Briefly, 4-aminophenylmercuric acetate (APMA) or trypsin activated MMPs were incubated with various concentrations of the inhibitor compound at room temperature for 5 minutes.

More specifically, recombinant human MMP-13 and MMP-1 enzymes were prepared in laboratories of the assignee. MMP-13 was expressed in baculovirus as a proenzyme, and purified first over a heparin agarose column and then over a chelating zinc chloride column. The proenzyme was activated by APMA for use in the assay. MMP-1 expressed in transfected HT-1080 cells was provided by Dr. Howard Welgus of Washington University, St. Louis, Mo. The enzyme was also activated using APMA and was then purified over a hydroxamic acid column.

The enzyme substrate is a methoxycoumarin-containing polypeptide having the following sequence:

MCA-ProLeuGlyLeuDpaAlaArgNH$_2$, wherein MCA is methoxycoumarin and Dpa is 3-(2,4-dinitrophenyl)-L-2,3-diaminopropionyl alanine. This substrate is commercially available from Baychem as product M-1895.

The buffer used for assays contained 100 mM Tris-HCl, 100 mM NaCl, 10 mM $CaCl_2$ and 0.05 percent polyethyleneglycol (23) lauryl ether at a pH value of 7.5. Assays were carried out at room temperature, and dimethyl sulfoxide (DMSO) at a final concentration of 1 percent was used to dissolve inhibitor compound.

The assayed inhibitor compound in DMSO/buffer solution was compared to an equal amount of DMSO/buffer with no inhibitor as control using Microfluor™ White Plates (Dynatech). The inhibitor or control solution was maintained in the plate for 10 minutes and the substrate was added to provide a final concentration of 4 μM.

In the absence of inhibitor activity, a fluorogenic peptide was cleaved at the gly-leu peptide bond, separating the highly fluorogenic peptide from a 2,4-dinitrophenyl quencher, resulting in an increase of fluorescence intensity (excitation at 328 nm/emission at 415 nm). Inhibition was measured as a reduction in fluorescent intensity as a function of inhibitor concentration, using a Perkin Elmer L550 plate reader. The $IC_{50}$ values were calculated from those values. The results are set forth in the Inhibition Table (Table 13) below, reported in terms of $IC_{50}$ values in nanomolar (nm) amounts.

TABLE 13

| Example | MMP-13 | MMP-1 | MMP-2 | MMP-3 | MMP-8 | MMP-9 |
|---|---|---|---|---|---|---|
| 1 | 243 | >10,000 | 1.8 | >10,000 | 180 | 1700 |
| 2 | 1.1 | 700 | 0.3 | 42.5 | 3.0 | 9.0 |
| 3 | 0.4 | 330 | 0.2 | 18.1 | 0.4 | 1.1 |
| 4 | 0.6 | 485 | 0.3 | 35 | 0.6 | 4.5 |
| 5 | 0.2 | 475 | 0.2 | | | |
| 6 | 8 | 2400 | 2.8 | 158 | 2.4 | 30 |
| 7 | 0.85 | 7700 | 0.9 | | 0.7 | 7.0 |
| 8 | 1.3 | 400 | 0.2 | | | |

EXAMPLE 9

In vivo Angiogenesis Assay

The study of angiogenesis depends on a reliable and reproducible model for the stimulation and inhibition of a neovascular response. The corneal micropocket assay provides such a model of angiogenesis in the cornea of a mouse. See, *A Model of Angiogenesis in the Mouse Cornea*; Kenyon, B M, et al., *Investigative Ophthalmology & Visual Science*, July 1996, Vol. 37, No.8.

In this assay, uniformly sized Hydron™ pellets containing bFGF and sucralfate were prepared and surgically implanted into the stroma mouse cornea adjacent to the temporal limbus. The pellets were formed by making a suspension of 20 μL sterile saline containing 10 μg recombinant bFGF, 10 mg of sucralfate and 10 μL of 12 percent Hydron™ in ethanol. The slurry was then deposited on a 10×10 mm piece of sterile nylon mesh. After drying, the nylon fibers of the mesh were separated to release the pellets.

The corneal pocket was made by anesthetizing a 7 week old C57Bl/6 female mouse, then proptosing the eye with a jeweler's forceps. Using a dissecting microscope, a central, intrastromal linear keratotomy of approximately 0.6 mm in length was performed with a #15 surgical blade, parallel to the insertion of the lateral rectus muscle. Using a modified cataract knife, a lamellar micropocket was dissected toward the temporal limbus. The pocket was extended to within 1.0 mm of the temporal limbus. A single pellet was placed on the corneal surface at the base of the pocket with a jeweler's forceps. The pellet was then advanced to the temporal end of the pocket. Antibiotic ointment was then applied to the eye.

Mice were dosed on a daily basis for the duration of the assay. Dosing of the animals was based on bioavailability and overall potency of the compound. an exemplary dose is 50 mg/kg bid, po. Neovascularization of the corneal stroma begins at about day three and was permitted to continue under the influence of the assayed compound until day five. At day five, the degree of angiogenic inhibition was scored by viewing the neovascular progression with a slit lamp microscope.

The mice were anesthetized and the studied eye was once again proptosed. The maximum vessel length of neovascularization, extending from the limbal vascular plexus toward the pellet was measured. In addition, the contiguous circumferential zone of neovascularization was measured as clock hours, where 30 degrees of arc equals one clock hour. The area of angiogenesis was calculated as follows.

$$\text{area} = \frac{(0.4 \times \text{clock hours} \times 3.14 \times \text{vessel length (in mm)})}{2}$$

The studied mice were thereafter compared to control mice and the difference in the area of neovascularization was recorded. A contemplated compound typically exhibits about 25 to about 80 percent inhibition, whereas the vehicle control exhibits zero percent inhibition. The results of this assay for several inhibitor compounds are shown in Table 14, below.

TABLE 14

| Example 6 | 80.0% |
|---|---|

From the foregoing, it will be observed that numerous modifications and variations can be carried out without departing from the true spirit and scope of the novel concepts of the present invention. It is to be understood that no limitation with respect to the specific example presented is intended or should be inferred. The disclosure is intended to cover by the appended claims all such modifications as fall within the scope of the claims.

What is claimed is:

1. A compound or a salt thereof, wherein:
the compound corresponds in structure to Formula II:

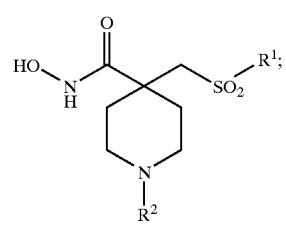

$R^2$ is straight or branched chain aliphatic $C_1$–$C_8$ hydrocarbyl, $C_1$–$C_6$ hydrocarbyloxycarbonyl $C_1$–$C_4$ hydrocarbyl, aryl $C_1$–$C_4$ hydrocarbyl, heteroaryl $C_1$–$C_4$ hydrocarbyl, wherein the heteroaryl is not pyridinyl; aryloxy $C_1$–$C_4$ hydrocarbyl, or heteroaryloxy $C_1$–$C_4$ hydrocarbyl; and $R^1$ is a substituent containing a 5- or 6-membered cyclohydrocarbyl, heterocyclo, aryl, or heteroaryl radical bonded directly to the depicted $SO_2$-group, wherein:
the cyclohydrocarbyl, heterocyclo, aryl, or heteroaryl is itself substituted at its own 4-position when a 6-membered ring or at its own 3- or 4-position when a 5-membered ring with a substituent selected from the group consisting of single-ringed cyclohydrocarbyl, single-ringed heterocyclo, single-ringed aryl, single-ringed heteroaryl, phenoxy, thiophenoxy, 4-thiopyridyl, phenylazo, phenylureido, nicotinamido, isonicotinamido, picolinamido, anilino, and benzamido.

2. The compound or salt according to claim 1, wherein $R^1$ is a single-ringed aryl or heteroaryl that is 5- or 6-membered, wherein:
the aryl or heteroaryl is itself substituted at its own 4-position when a 6-membered ring or at its own 3- or 4-position when a 5-membered ring with a substituent selected from the group consisting of single-ringed aryl, single-ringed heteroaryl, phenoxy, thiophenoxy, 4-thiopyridyl, phenylazo, phenylureido, and benzamido.

3. The compound or salt according to claim 1 wherein:
$R^1$ is phenyl substituted with $R^3$ at the 4-position, and
$R^3$ is phenyl, phenoxy, thiophenoxy, phenylazo, benzamido, nicotinamido, isonicotinamido, picolinamido, or phenylureido.

4. A compound or salt thereof, wherein:
the compound corresponds in structure to Formula II:

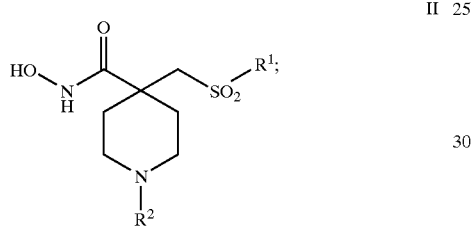

II $R^2$ is straight or branched chain aliphatic $C_1$–$C_8$ hydrocarbyl, $C_1$–$C_6$ hydrocarbyloxycarbonyl $C_1$–$C_4$ hydrocarbyl, aryl $C_1$–$C_4$ hydrocarbyl, heteroaryl $C_1$–$C_4$ hydrocarbyl, wherein the heteroaryl is not pyridinyl; aryloxy $C_1$–$C_4$ hydrocarbyl, or heteroaryloxy $C_1$–$C_4$ hydrocarbyl;
$R^1$ is phenyl substituted with $R^3$ at the 4-position; and
$R^3$ is phenyl, phenoxy, or thiophenoxy, wherein the phenyl, phenoxy, or thiophenoxy is optionally substituted:
at the meta- or para-position or both with a moiety that is selected from the group consisting of $C_1$–$C_9$ hydrocarbyloxy, $C_1$–$C_{10}$ hydrocarbyl, di-$C_1$–$C_9$ hydrocarbylamino, carboxyl $C_1$–$C_8$ hydrocarbyl, $C_1$–$C_4$ hydrocarbyloxy carbonyl $C_1$–$C_4$ hydrocarbyl, $C_1$–$C_4$ hydrocarbyloxycarbonyl $C_1$–$C_4$ hydrocarbyl, and carboxamido $C_1$–$C_8$ hydrocarbyl, or
at the meta- and para-positions by two methyl groups or by a methylenedioxy group.

5. A compound or salt thereof, wherein:
the compound corresponds in structure to Formula II:

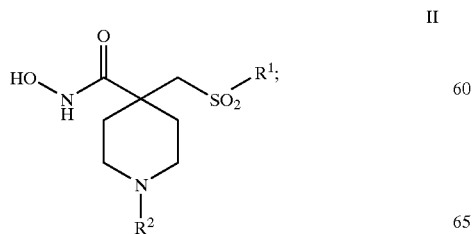

II $R^2$ is straight or branched chain aliphatic $C_1$–$C_8$ hydrocarbyl, $C_1$–$C_6$ hydrocarbyloxycarbonyl $C_1$–$C_4$ hydrocarbyl, aryl $C_1$–$C_4$ hydrocarbyl, heteroaryl $C_1$–$C_4$ hydrocarbyl, wherein the heteroaryl is not pyridinyl; aryloxy $C_1$–$C_4$ hydrocarbyl, or heteroaryloxy $C_1$–$C_4$ hydrocarbyl;
$R^1$ is phenyl substituted with $R^3$ at the 4-position; and
$R^3$ is benzamido, nicotinamido, anilino, isonicotinamido, picolinamido, or phenylureido, wherein:
the benzamido, nicotinamido, anilino, isonicotinamido, picolinamido, or phenylureido is optionally substituted at its own meta- or para-position or both with a moiety selected from the group consisting of nitro, $C_1$–$C_8$ hydrocarbyl, $C_1$–$C_7$ hydrocarbyloxy, amino, and amino-$C_2$–$C_4$ hydroxyalkyl.

6. A compound or salt thereof, wherein:
the compound or salt is characterizeable in that the compound or salt selectively inhibits in vitro human MMP-13, MMP-9, and/or MMP-2 activity over in vitro human MMP-1 activity;
the compound corresponds in structure to Formula II:

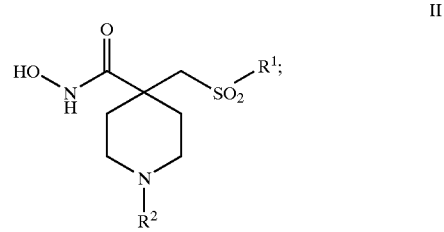

II $R^2$ is straight or branched chain aliphatic $C_3$–$C_6$ hydrocarbyl, t-butoxycarbonyl, phenethyl, 2-propynyl, or 3-methoxybenzyl; and
$R^1$ is a substituent containing a 5- or 6-membered cyclohydrocarbyl, heterocyclo, aryl, or heteroaryl radical bonded directly to the depicted $SO_2$-group, wherein:
the cyclohydrocarbyl, heterocyclo, aryl, or heteroaryl is itself substituted at its own 4-position when a 6-membered ring or at its own 3- or 4-position when a 5-membered ring with a substituent selected from the group consisting of single-ringed cyclohydrocarbyl, single-ringed heterocyclo, single-ringed aryl, single-ringed heteroaryl, phenoxy, thiophenoxy, 4-thiopyridyl, phenylazo, phenylureido, nicotinamido, isonicotinamido, picolinamido, anilino, and benzamido.

7. A compound or salt wherein the compound corresponds in structure to the following formula:

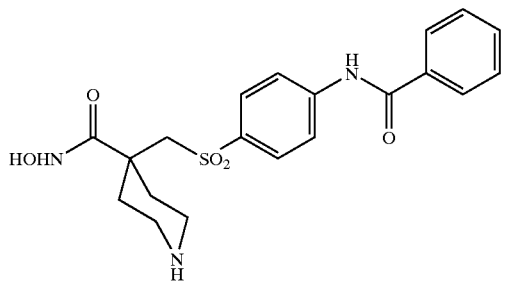

8. A compound or salt according to claim 1, wherein the compound corresponds in structure to the following formula:

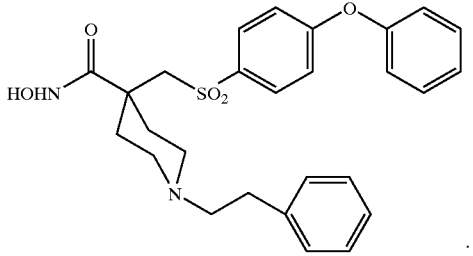

9. A compound or salt thereof according to claim 6, wherein the compound corresponds in structure to the following formula:

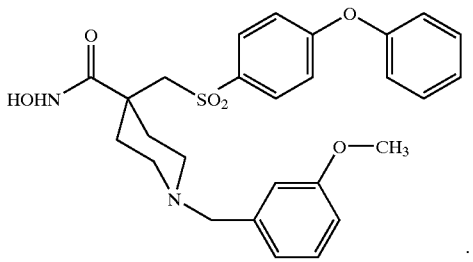

10. A compound or salt according to claim 1, wherein the compound corresponds in structure to the following formula:

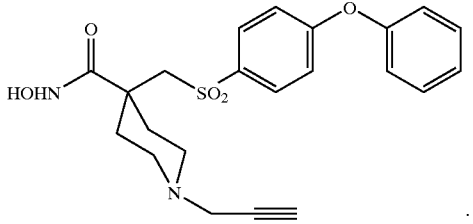

11. A compound or salt thereof according to claim 6, wherein the compound corresponds in structure to the following formula:

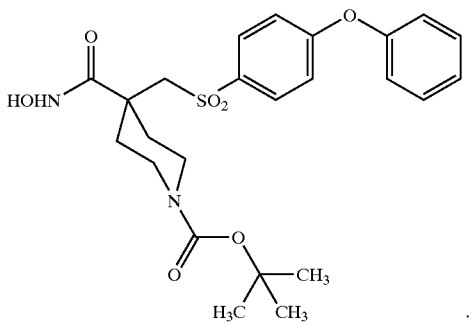

12. A compound or salt according to claim 4, wherein the compound corresponds in structure to the following formula:

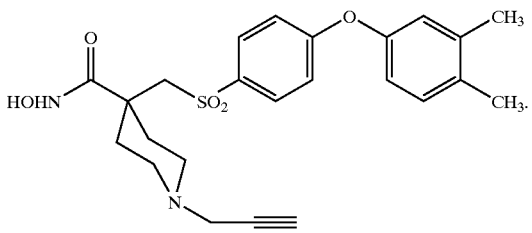

13. A process for treating a pathological condition in a mammal, wherein:
the pathological condition is treatable by inhibiting matrix metalloprotease activity;
the process comprises administering a matrix metalloprotease inhibitor compound or a pharmaceutically acceptable salt thereof in an effective amount to the mammal;
the compound corresponds in structure to Formula II:

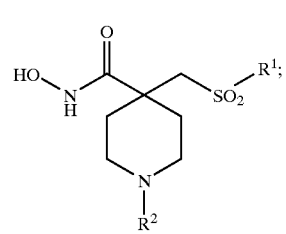

II $R^2$ is straight or branched chain aliphatic $C_1$–$C_8$ hydrocarbyl, $C_1$–$C_6$ hydrocarbyloxycarbonyl $C_1$–$C_4$ hydrocarbyl, aryl $C_1$–$C_4$ hydrocarbyl, heteroaryl $C_1$–$C_4$ hydrocarbyl, wherein the heteroaryl is not pyridinyl; aryloxy $C_1$–$C_4$ hydrocarbyl, or heteroaryloxy $C_1$–$C_4$ hydrocarbyl; and $R^1$ is a substituent containing a 5- or 6-membered cyclohydrocarbyl, heterocyclo, aryl, or heteroaryl radical bonded directly to the depicted $SO_2$-group, wherein:
the cyclohydrocarbyl, heterocyclo, aryl, or heteroaryl is itself substituted at its own 4-position when a 6-membered ring or at its own 3- or 4-position when a 5-membered ring with a substituent selected from the group consisting of single-ringed cyclohydrocarbyl, single-ringed heterocyclo, single-ringed aryl, single-ringed heteroaryl, phenoxy, thiophenoxy, 4-thiopyridyl, phenylazo, phenylureido, nicotinamido, isonicotinamido, picolinamido, anilino, and benzamido.

14. A process according to claim 13, wherein $R^1$ is a single-ringed aryl or heteroaryl that is 5- or 6-membered, wherein:
the aryl or heteroaryl is itself substituted at its own 4-position when a 6-membered ring or at its own 3- or 4-position when a 5-membered ring with a substituent selected from the group consisting of single-ringed aryl, single-ringed heteroaryl, phenoxy, thiophenoxy, 4-thiopyridyl, phenylazo, phenylureido, and benzamido.

15. A process for treating a pathological condition in a mammal, wherein:

the pathological condition is treatable by inhibiting matrix metalloprotease activity;

the process comprises administering a matrix metalloprotease inhibitor compound or a pharmaceutically acceptable salt thereof in an effective amount to the mammal;

the compound corresponds in structure to Formula II:

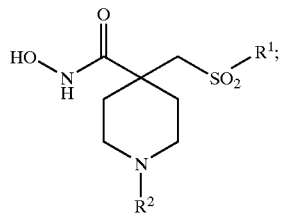

II $R^2$ is straight or branched chain aliphatic $C_1-C_8$ hydrocarbyl, $C_1-C_6$ hydrocarbyloxycarbonyl $C_1-C_4$ hydrocarbyl, aryl $C_1-C_4$ hydrocarbyl, heteroaryl $C_1-C_4$ hydrocarbyl, wherein the heteroaryl is not pyridinyl; aryloxy $C_1-C_4$ hydrocarbyl, or heteroaryloxy $C_1-C_4$ hydrocarbyl;

$R^1$ is phenyl substituted with $R^3$ at the 4-position; and $R^3$ is phenyl, phenoxy, or thiophenoxy, wherein the phenyl, phenoxy, or thiophenoxy is optionally substituted:

at the meta- or para-position or both with a moiety that is selected from the group consisting of $C_1-C_9$ hydrocarbyloxy, $C_1-C_{10}$ hydrocarbyl, di-$C_1-C_9$ hydrocarbylamino, carboxyl $C_1-C_8$ hydrocarbyl, $C_1-C_4$ hydrocarbyloxy carbonyl $C_1-C_4$ hydrocarbyl, $C_1-C_4$ hydrocarbyloxycarbonyl $C_1-C_4$ hydrocarbyl, and carboxamido $C_1-C_8$ hydrocarbyl, or at the meta- and para-positions by two methyl groups or by a methylenedioxy group.

16. A process for treating a pathological condition in a mammal, wherein:

the pathological condition is treatable by inhibiting matrix metalloprotease activity;

the process comprises administering a matrix metalloprotease inhibitor compound or a pharmaceutically acceptable salt thereof in an effective amount to the mammal;

the compound corresponds in structure to Formula II:

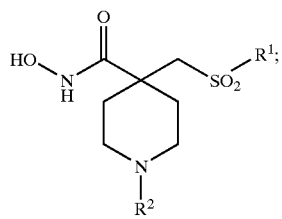

II $R^2$ is straight or branched chain aliphatic $C_1-C_8$ hydrocarbyl, $C_1-C_6$ hydrocarbyloxycarbonyl $C_1-C_4$ hydrocarbyl, aryl $C_1-C_4$ hydrocarbyl, heteroaryl $C_1-C_4$ hydrocarbyl, wherein the heteroaryl is not pyridinyl; aryloxy $C_1-C_4$ hydrocarbyl, or heteroaryloxy $C_1-C_4$ hydrocarbyl;

$R^1$ is phenyl substituted with $R^3$ at the 4-position; and $R^3$ is benzamido, nicotinamido, anilino, isonicotinamido, picolinamido, or phenylureido, wherein:

the benzamido, nicotinamido, anilino, isonicotinamido, picolinamido, or phenylureido is optionally substituted at its own meta- or para-position or both with a moiety selected from the group consisting of nitro, $C_1-C_8$ hydrocarbyl, $C_1-C_7$ hydrocarbyloxy, amino, and amino-$C_2-C_4$ hydroxyalkyl.

17. A process for treating a pathological condition in a mammal, wherein:

the pathological condition is treatable by inhibiting matrix metalloprotease activity;

the process comprises administering a matrix metalloprotease inhibitor compound or a pharmaceutically acceptable salt thereof in an effective amount to the mammal;

the compound or salt is characterizeable in that the compound or salt selectively inhibits in vitro human MMP-13, MMP-9, and/or MMP-2 activity over in vitro human MMP-1 activity;

the compound corresponds in structure to Formula II:

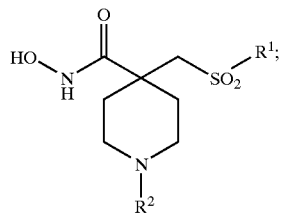

II $R^2$ is straight or branched chain aliphatic $C_3-C_6$ hydrocarbyl, t-butoxycarbonyl, phenethyl, 2-propynyl, or 3-methoxybenzyl; and $R^1$ is a substituent containing a 5- or 6-membered cyclohydrocarbyl, heterocyclo, aryl, or heteroaryl radical bonded directly to the depicted $SO_2$-group, wherein:

the cyclohydrocarbyl, heterocyclo, aryl, or heteroaryl is itself substituted at its own 4-position when a 6-membered ring or at its own 3- or 4-position when a 5-membered ring with a substituent selected from the group consisting of single-ringed cyclohydrocarbyl, single-ringed heterocyclo, single-ringed aryl, single-ringed heteroaryl, phenoxy, thiophenoxy, 4-thiopyridyl, phenylazo, phenylureido, nicotinamido, isonicotinamido, picolinamido, anilino, and benzamido.

18. A process according to claim 13, wherein:

$R^1$ is phenyl substituted with $R^3$ at the 4-position, and $R^3$ is phenyl, phenoxy, thiophenoxy, phenylazo, benzamido, nicotinamido, isonicotinamido, picolinamido, or phenylureido.

19. A process for treating a pathological condition in a mammal, wherein:

the pathological condition is treatable by inhibiting matrix metalloprotease activity;

the process comprises administering a matrix metalloprotease inhibitor compound or a pharmaceutically acceptable salt thereof in an effective amount to the mammal;

wherein the compound corresponds in structure to the following formula:

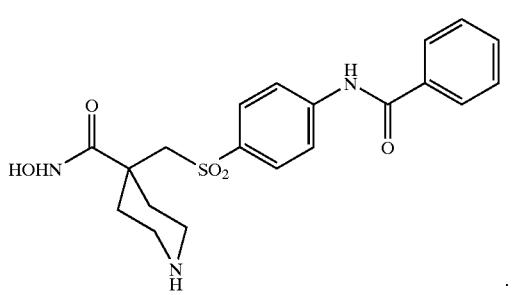

20. A process according to claim 13, wherein the compound corresponds in structure to the following formula:

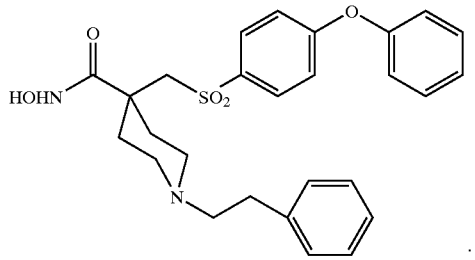

21. A process according to claim 13, wherein the compound corresponds in structure to the following formula:

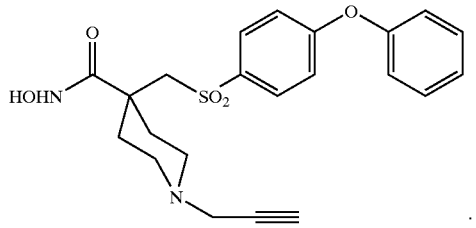

22. A process according to claim 15, wherein the compound corresponds in structure to the following formula:

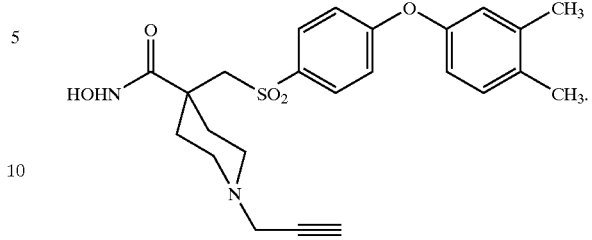

23. A process according to claim 17, wherein:
the compound corresponds in structure to the following formula:

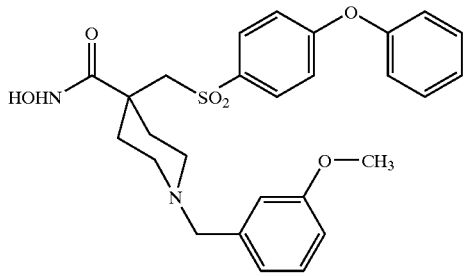

24. A process according to claim 17, wherein:
the compound corresponds in structure to the following formula:

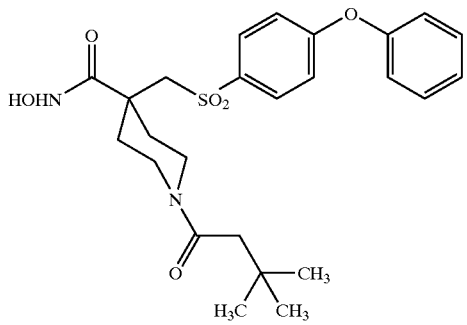

* * * * *